United States Patent [19]
Hackett, Jr. et al.

[11] Patent Number: 6,015,662
[45] Date of Patent: Jan. 18, 2000

[54] REAGENTS FOR USE AS CALIBRATORS AND CONTROLS

[75] Inventors: John R. Hackett, Jr., Gurnee; Jane A. Hoff, Naperville; David H. Ostrow, Lake Zurich; Alan M. Golden, Wilmette, all of Ill.

[73] Assignee: Abbott Laboratories, Abbott Park, Ill.

[21] Appl. No.: 08/589,939

[22] Filed: Jan. 23, 1996

[51] Int. Cl.[7] .................. G01N 33/569; G01N 33/577
[52] U.S. Cl. .......................... 435/5; 435/7.2; 435/7.22; 435/7.31; 435/7.32; 435/7.34; 436/548
[58] Field of Search .................. 435/5, 7.2, 7.22, 435/7.31, 7.32, 7.34; 436/548

[56] References Cited

U.S. PATENT DOCUMENTS

| | | | |
|---|---|---|---|
| 4,292,403 | 9/1981 | Duermeyer | 435/5 |
| 4,433,059 | 2/1984 | Chang et al. | 436/512 |
| 5,008,183 | 4/1991 | Osther | 435/5 |
| 5,183,735 | 2/1993 | Lopez et al. | 435/6 |
| 5,447,837 | 9/1995 | Urnovitz | 435/5 |
| 5,447,838 | 9/1995 | Meiklejohn et al. | 435/5 |
| 5,462,852 | 10/1995 | Arthur et al. | 435/5 |
| 5,478,753 | 12/1995 | Wong et al. | 436/513 |
| 5,491,218 | 2/1996 | Brust et al. | |

FOREIGN PATENT DOCUMENTS

| | | |
|---|---|---|
| 0062227 | 10/1982 | European Pat. Off. |
| 0216846 | 4/1987 | European Pat. Off. |
| 0429218 | 5/1991 | European Pat. Off. |
| 0537488 | 4/1993 | European Pat. Off. |
| 0636886 | 2/1995 | European Pat. Off. |
| 0646794 | 4/1995 | European Pat. Off. |
| 8601533 | 9/1985 | WIPO. |
| 8910980 | 11/1989 | WIPO. |
| 9119196 | 12/1991 | WIPO. |

OTHER PUBLICATIONS

Butler, J.E. and Hamilton, R.G., In *Immunochemistry of Solid–phase Immunoassay*, Butler, J.E. ed., CRC Press, Boca Raton, pp. 173–198 (1991).

Hamilton, R.G., Engineered human antibodies as immunologic quality control reagents, Ann. Biol. Clin. 48:473–477 (1990).

Decoster, et al., "Platelia–Toxo IgA, a new kit for early diagnosis of congenital toxoplasmosis by detection of anti–P30 immunoglobulin A antibodies", Journal of Clinical Microbiology, vol. 29, No. 10, 2291–2295, Oct. 1991.

Kuroki et al., "Reducing interference from heterophilic antibodies in a two–site immunoassay for carcinoembryonic antigen (CEA) by using a human/mouse chimeric antibody to CEA as the tracer", Journal of Immunological Methods, vol. 180, pp. 81–91, 1995.

Jin et al., Molecular Immunology, vol. 30, No. 18, pp. 1647–1654, 1993.

Li et al., Molecular Immunology, vol. 27, No. 3, pp. 303–311, 1990.

Major et al., Hum. Antibod. Hybridomas, vol. 5, 1 and 2, pp. 9–17, 1994.

*Primary Examiner*—Donna C. Wortman
*Assistant Examiner*—Brenda G. Brumback
*Attorney, Agent, or Firm*—Cheryl L. Becker

[57] ABSTRACT

The present invention relates to the use of a reagent that binds specifically to a predetermined ligand, contains one or more antibody constant region epitopes, and is uniform in specificity and affinity. The reagent can be produced continually, in the manufacture of calibrators (standards) and/or controls for diagnostic kits designed to qualitatively or quantitatively measure antibodies specific for a desired ligand. For example, the present invention encompasses recombinant mouse-human chimeric antibodies which may be used as calibrators (standards) and/or positive controls in assays and kits which measure human antibodies. Any species may be used in creating the chimeric antibodies, and the presence of any corresponding species of antibody may be detected.

55 Claims, 16 Drawing Sheets

Xho I
[CTCGAG]ACTC CAACCATGGG ATGGAGCTGG ATCTTTCTCT TTCTCCTGTC    50
            M  G  W  S  W   I  F  L  F   L  L  S

AGTAACTGCA GGTGTTCACT CCCAGGTCCA TCTGCAGCAG TCTGGAGCTG    100
 V  T  A   G  V  H  S   Q  V  H   L  Q  Q   S  G  A  E
                                  +1
AGCTGGTAAG GCCTGGGACT TCAGTGAAGG TGTCCTGCAA GGCTTCTGGA    150
 L  V  R   P  G  T     S  V  K  V   S  C  K   A  S  G
                 CDR1
TACGCCTTCA CTAATTACTT GATAGAGTGG GTGACACAGA GGCCTGGACA    200
 Y  A  F  T   N  Y  L   I  E  W   V  T  Q  R   P  G  Q
                                              CDR2
GGGCCTTGAG TGGATTGGAG TGATTAATCC TGGAAGTGAT TTTACTTACT    250
 G  L  E   W  I  G  V   I  N  P   G  S  D   F  T  Y  Y

ACAATGAGAA ATTCAAGGGC AGGGCAACAC TGACTGCAGA CAAATCCTCC    300
 N  E  K   F  K  G   R  A  T  L   T  A  D   K  S  S

AGCACTGCCT ACATGCAGCT CACCAGCCTG ACATCTGATG ACTCTGCGGT    350
 S  T  A  Y   M  Q  L   T  S  L   T  S  D  D   S  A  V
                                  CDR3
CTATTTCTGT GCAAGAACTA TTGTGACTAC GGACTACTTT GACTACTGGG    400
 Y  F  C   A  R  T   I  V  T  T   D  Y  F   D  Y  W  G
                              ↓
GCCAAGGCAC CCCTCTCACA GTCTCCTCAG GTAAGTGTGT C[AAGCTT]    447
 Q  G  T   P  L  T   V  S  S              Hind III

FIG.6

Xba I

| | | | | | |
|---|---|---|---|---|---|
| TCTAGAGCTC | TCAGAGATGG | AGTCAGACAC | ACTCCTGCTA | TGGGTGCTAC | 50 |
| | M E | S D T | L L L | W V L L | |
| TGCTCTGGGT | TCCAGGCTCC | ACTGGTGACA | TTGTGCTGAC | CCAATCTCCA | 100 |
| L W V | P G S | T G D | I V L T | Q S P | |
| | | +1 | | | |
| GCTTCTTTGG | CTGTGTCTCT | GGGGCAGAGG | GCCACCATCT | CCTGCAGAGC | 150 |
| A S L | V S L | G Q R | A T I S | C R A | |
| | | CDR1 | | | |
| CAGCGAAAGT | GTCAGTATTC | GTGGTGCTGG | TTTAATGCAC | TGGTATCAAC | 200 |
| S E S | V S I | R G A G | L M H | W Y Q Q | |
| | | | | CDR2 | |
| AGAAACCAGG | ATATCCACCC | AAACTCCTCA | TCTATGCTGC | ATCCAACCTA | 250 |
| K P G | Y P P | K L L I | Y A A | S N L | |
| GAATCTGGGG | TGCCTGCCAG | GTTTAGTGGC | AGAGGGTCTG | GGACAGACTT | 300 |
| E S G V | P A R | F S G | R G S G | T D F | |
| CACCCTCAAC | ATTCATCCTG | TGGAGGAAGC | TGATGCTGCA | ACCTATTTCT | 350 |
| T L N | I H P V | E E A | D A A | T Y F C | |
| | | CDR3 | | | |
| GTCAGCAAAG | TAGGAGATAT | CCGTATACGT | TCGGATCGGG | GACCAAGCTG | 400 |
| Q Q S | R R Y | P Y T F | G S G | T K L | |
| GAAATAAAAC | GTAAGTGTGT | CAGGATCC | | | 428 |
| E I K | | Bam HI | | | |

FIG.7

Xho I
CTCGAG ACAT CATGGCTTGG GTGTGGACCT TGCTATTCCT GATGGCAGCT      50
         M   A  W   V  W  T  L   L  F  L   M  A  A

GCCCAAAGTA TCCAAGCACA GATCCAGTTG GTGCAGTCTG GACCTGAGCT       100
 A  Q  S  I  Q  A  Q   I  Q  L   V  Q  S  G   P  E  L
                    +1
GAAGAAGCCT GGAGAGACAG TCAAGATCTC CTGCAAGGCT TCTGGGTATA       150
 K  K  P   G  E  T  V   K  I  S   C  K  A   S  G  Y  T
              CDR1
CCTTCACACA CTATCCAATG CACTGGGTGA AGCAGGCTCC AGGAAAGAGT       200
 F  T  H   Y  P  M   H  W  V  K   Q  A  P   G  K  S
                                    CDR2
TTAAAGTGGA TGGGCTGGAT AAACACCAAG TCTGGAGTGC CAACATATGC       250
 L  K  W  M  G  W  I   N  T  K   S  G  V  P   T  Y  A

AGATGACTTC AAGGGACGGT TTGCCTTCTC TTTGGAAACC  TCTGCCAGCA      300
 D  D  F   K  G  R  F   A  F  S   L  E  T   S  A  S  T

CTGCATGTTT GCAGATCACC AACCTCAAAA ATGAGGACAT GGCTACATAT       350
 A  C  L   Q  I  T   N  L  K  N   E  D  M   A  T  Y
                                    CDR3
TTCTGTGTAA GAGGAGGGCT CTACTATGAT TATTTCTATG GTGTGGACTA       400
 F  C  V  R  G  G  L   Y  Y  D   Y  F  Y  G   V  D  Y
                                     ↓
CTGGGGTCAA GGAACCTCAG TCACCGTCTC CTCAGGTAAG TGTGTC AAGCTT    452
 W  G  Q   G  T  S  V   T  V  S   S                Hind III

FIG.8

Xba I
```
TCTAGACCTC AAATGAAGTT GCCTGTTAGG CTGTTGGTGC TGATGTTCTG    50
         M  K  L  P  V  R  L  L  V  L  M  F  W

GATTCCTGCT TCCAGCAGTG ATGTGGTGAT GACCCAGACT CCACTCTCCC   100
 I  P  A  S  S  S  D  V  V  M  T  Q  T  P  L  S  L
                +1
TGCCTGTCAG TCCTGGAGAT CAAGCCTCGA TCTCTTGCAG ATCTAGTCAG   150
 P  V  S  P  G  D  Q  A  S  I  S  C  R  S  S  Q
            CDR1
AGCCTTGTAC ACAGTTATGG AAACACCTAT TTACATTGGT ATCTGCAGAA   200
 S  L  V  H  S  Y  G  N  T  Y  L  H  W  Y  L  Q  K
                                             CDR2
GCCAGGCCAG TCTCCAAAAC TCCTGATCTA CAAAGTTTCC AACCGATTTT   250
 P  G  Q  S  P  K  L  L  I  Y  K  V  S  N  R  F  S

CTGGGGTCCC AGACAGGTTC AGTGGCAGTG GATCAGGGAC AGATTTCACA   300
 G  V  P  D  R  F  S  G  S  G  S  G  T  D  F  T

CTCAAGATCA GCAGAGTGGA GGCTGAGGAT CTGGGAGTTT ATTTCTGCTC   350
 L  K  I  S  R  V  E  A  E  D  L  G  V  Y  F  C  S
           CDR3
TCAAAGTACA CATGTTCCGT GGACGTTCGG TGGAGGCACC AAGCTGGAAA   400
 Q  S  T  H  V  P  W  T  F  G  G  T  K  L  E  I
      ↓
TCAAACGTAA GTGTGTCAGG ATCC                              424
 K                    Bam HI
```

FIG.9

REAGENTS FOR USE AS CALIBRATORS AND CONTROLS

BACKGROUND OF THE INVENTION

1. Field of the Invention

The present invention relates to a method of using reagents as calibrators (standards) and/or controls in diagnostic assays and kits. More specifically, one or more of these reagents may be used in place of seropositive plasma or serum in the production of calibrators and/or controls for diagnostic assays and kits designed to qualitatively or quantitatively measure antibodies specific for a desired ligand. The reagents themselves bind specifically to a predetermined ligand, contain one or more antibody constant region epitopes, and are homogeneous in specificity and affinity. The reagents may be produced by the use of hybridoma and/or recombinant DNA technology.

2. Background Information

Antibodies are multidomain proteins composed of two identical light (L) and two identical heavy (H) polypeptide chains, linked together by disulfide bonds (FIG. 1). The amino terminal domain of both the L and H chains exhibits considerable diversity in amino acid sequence and conformation and is referred to as the variable (V) region. Residing within each V region are three segments of exceptional variability, referred to as hypervariable regions or complementarity-determining regions (CDRs), that form the ligand binding pocket. The other domains of both the L and H chains constitute the constant regions. The constant regions are not involved in ligand binding and exhibit more limited variation. Constant regions are species specific and can be divided into various classes and subclasses based on differences in the heavy chain constant region including size, charge, amino acid composition, glycosylation and biological function (Carayannopoulos, L. and Capra, J. D. Structure and Function of Immunoglobulins, In Fundamental Immunology, 3rd edition, Paul W. E. ed., Raven Press Ltd., New York, pgs. 283–314 (1993)).

The immune system generates a remarkably diverse repertoire of antibody molecules capable of recognizing virtually any substance. The primary antibody response induced by challenge with antigen (i.e., any substance capable of eliciting an immune response, for example, proteins, carbohydrates, nucleic acids, lipids, or hapten conjugated to a carrier) results in the production of antibodies predominantly of the IgM class. This response is polyclonal in nature, as a heterogeneous mixture of antibodies against different epitopes of the antigen is produced. Subsequent or prolonged challenge with the same antigen leads to a secondary response characterized by significantly greater titers of antibody than that seen in the primary response that are generally higher in affinity (measure of the binding strength between an epitope and the antibody combining site) and composed almost entirely of the IgG class. The specific IgM titer generally wanes more rapidly than the specific IgG titer. As a result, monitoring the class of specific antibody present in serum or other biological fluids provides an indicator of the individual's immune status to a specific antigen (e.g., infectious agents). Antibody class can also be of clinical relevance in cases of autoimmunity and for monitoring Type I hypersensitivity (allergic responses) associated with production of IgE class antibodies (Roitt, I. ed., Immunology, Gower Medical Publishing Ltd., London, England (1985); Paul W. E. ed., Fundamental Immunology, 3rd edition, Raven Press Ltd., New York (1993)).

Irrespective of class, antibody molecules bind to ligands with high affinity and specificity (the ability to discriminate between the epitope to which it is directed and any other epitope) making them ideal immunodiagnostic reagents. Immunoassays provide a rapid and sensitive method to monitor for infectious agents, physiological function, allergy, autoimmunity, cancer, pharmaceuticals, and drugs of abuse. Manual and automated immunoassays have been designed to measure the antibody response in general, antibody to a specific antigen, and diagnostically relevant antigens or haptens. Heterologous immunoassays generally consist of multiple reaction steps and ultimately require separation of the immune complexed reactant from the free reactants to obtain the test result. In contrast, homogeneous immunoassays, are solution-phase systems that do not require the separation of complexed reactant from free reactants. Immunoassays have been developed with many different formats, but can be divided into two main classes: (1) competitive assays, and (2) non-competitive assays (e.g. immunometric, sandwich). For heterologous immunoassays of both classes, solid-phase biochemistry for separation of bound and free reactants has proven revolutionary. Antibody or antigen reagents can be covalently or non-covalently (e.g. ionic, hydrophobic) attached to the solid phase. Linking agents for covalent attachment are known and may be part of the solid phase or derivatized to it prior to coating. Examples of solid phases used in immunoassays are, porous and non-porous materials, latex particles, magnetic particles, microparticles, beads, membranes, microtiter wells and plastic tubes. The choice of solid phase material and method of labeling the antigen or antibody reagent is determined based on desired assay format performance characteristics. For some immunoassays, no label is required. For example, if the antigen is on a detectable particle such as a red blood cell, reactivity can be established based on agglutination. Alternatively, antigen-antibody reaction may result in a visible change (e.g., radial immunodiffusion). In most cases, one of the antibody or antigen reagents used in an immunoassay is attached to a signal generating compound or "label". This signal generating compound or "label" is in itself detectable or may be reacted with one or more additional compounds to generate a detectable product. Examples of signal generating compounds include chromogens, radioisotopes (e.g. $^{125}$I, $^{131}$I, $^{32}$P, $^{3}$H, $^{35}$S, and $^{14}$C), fluorescent compounds (e.g. fluorescein, rhodamine), chemiluminescent compounds, particles (visible or fluorescent), nucleic acids, complexing agents, or catalysts such as enzymes (e.g. alkaline phosphatase, acid phoshatase, horseradish peroxidase, beta-galactosidase, and ribonuclease). In the case of enzyme use, addition of chromo-, fluoro- or lumo-genic substrate results in generation of a detectable signal. Other detection systems such as time-resolved fluorescence, internal-reflection fluorescence, amplification (e.g. polymerase chain reaction) and Raman spectroscopy are also useful.

Immunoassays have been developed to monitor biological fluids (e.g., plasma, serum, cerebrospinal fluid, saliva, tears, nasal washes, or aqueous extracts of tissues and cells) for the presence of antibody specific for an antigen of interest (e.g. infectious agent, autoantigen, allergen). In many cases, these specific antibody immunoassays have been designed to be antibody class or subclass specific. There are two general formats commonly utilized to monitor specific antibody in humans: (1) antigen is presented on a solid phase, the human biological fluid containing specific antibodies is allowed to react with the antigen, and then antibody bound to antigen is detected with an anti-human antibody coupled to a signal generating compound and (2) an anti-human antibody is bound to the solid phase, the human biological fluid containing specific antibodies is allowed to react with the antibody, and then antigen attached to a signal generating compound is added to detect specific antibody. In both formats, the anti-human antibody reagent can be polyclonal or monoclonal. Moreover, the anti-human antibody reagent may recognize all antibody classes, or alternatively, be specific for a particular class or subclass of antibody, depending upon the intended purpose of the assay. The reactivity of this reagent reflects the spectrum of antibodies of which it is composed and the particular antibody constant region epitopes to which they bind. Constant region epitopes are antigenic determinants to which an antibody response can be generated. Examples of constant region epitopes include: species invariant epitopes (class or subclass specific epitopes), and allotypic epitopes (present on some, but not all members of a species). Methods for manufacturing and testing of anti-human antibody reagents that bind to constant region epitopes are well known to the art. Assays for monitoring of specific antibody response in other species could be designed in an analogous manner by one skilled in the art.

Immunoassays designed to detect specific antibody provide a measure of antibody activity. This may be referred to as antibody titer, e.g. mid-point or end-point titer, or expressed in units (activity or gravimetric) relative to a reference standard. Immunoassays and kits typically include one or more components containing the specific antibody being measured that function as calibrators (standards) and/or positive control. Calibrators (standards) are used to establish calibration (standard) curves for interpolation of antibody concentration, or alternatively, a single calibrator may be used near the positive/negative cutoff. The positive control is used to establish assay performance characteristics and is a useful indicator of the integrity of the reagents. In addition, immunoassays and kits to detect specific antibody generally include a negative control, such as serum or plasma, that contains no antibody reactive with the antigen of interest. Preferably, the calibrators and positive controls are prepared with the specific antibody being measured or a material chemically similar to it. Ideally the calibrator(s) and controls are manufactured to interact with the other assay components in a manner analogous to the test analyte (specific antibody). Calibrators and positive controls are generally manufactured by spiking known quantities of specific antibody derived from seropositive plasma or serum (polyclonal antibody) into the negative control reagent. Often times multiple calibrators are included that contain varying concentrations of specific antibody that span the range of concentrations the assay is designed to measure. Quantitative immunoassays may include up to 8 calibrators (standards) to establish a calibration (standard) curve from which results can be interpolated. The quantity of specific antibody assigned to the calibrator(s) and control(s) is standardized against primary reference standards. In the case of antibody activity, the reference standard is often established using individual or pooled sera that has been characterized empirically for characteristics such as quantity, quality, and specificity. The reference standard may be assigned relative units of activity or be a gravimetric quantity of antibody. For qualitative immunoassays, a single calibrator (standard) may be used that is set near the positive/negative cutoff. Some manufacturer's refer to the single calibrator (standard) as an index calibrator (Voller, A. et. al., Immunoassays for the 80s, University Park Press, Baltimore (1981); Albertini, A. and Ekins, R., eds., Monoclonal Antibodies and Developments in Immunoassay, Elsevier/North-Holland Biomedical Press, New York (1981); Butler, J., ed., Immunochemistry of Solid-Phase Immunoassay, CRC Press, Boca Raton (1991)).

Two examples of an immunometric antibody-capture based immunoassay are the IMx Toxo IgM and Toxo IgG (FIG. 2) antibody assays manufactured by Abbott Laboratories. Both assays are automated Microparticle Enzyme Immunoassay (MEIA) which measure antibodies to *Toxoplasma gondii* (*T. gondii*) in human serum or plasma (Safford, J. W. et. al., J. Clin. Pathol. 44:238–242 (1991)). One assay qualitatively measures IgM antibodies, indicative of recent exposure or acute infection, and the other assay quantitatively measures IgG, indicative of chronic or past infection. *T. gondii*, an obligate intracellular parasite infecting adults often asymptomatically, can lead to serious consequences for the fetus due to transplacental transmission which occurs during acute acquired maternal infection (Remington, J. S. and Krahenbuhl J. L., Comprehensive Immunology (A. J. Nahmias and O'Reilly. Eds.) pgs. 327–371. Plenum, New York/London (1982); Remington, J. S., Intrauterine Infections: Birth defects Origin. Ser 4:47–56. The National Foundation of the March of Dimes, New York (1968)). Determination of maternal immune status by testing for the presence of T. gondii specific IgM or IgG antibodies can aid in the determination of pregnancies at risk and in the case of seronegative individuals allows one to monitor for seroconversion that would be indicative of acute infection (Desmonts, G. and Couvreur J., New Engl. J. Med. 290:1110–1116 (1974); McCabe, R. and Remington J. S., New Engl. J. Med. 318:313–317 (1988); Sibalic, D. et. al., Gynecol. Obstet. Invest. 36:91–95 (1993)). These assays use microparticles coated with *T. gondii* antigens as the solid phase. Specimen is added to the coated microparticles to allow antibodies specific for *T. gondii* to bind. Subsequently, an alkaline phosphatase conjugated anti-human IgM (or anti-human IgG) is added that binds specifically to IgM (or IgG) class antibodies complexed to the *T. gondii* antigens. Following addition of a suitable substrate, the rate of enzyme-catalyzed turnover is monitored based on fluorescence.

The calibrators and positive controls for the IgM and IgG anti-*T. gondii* assays are prepared from plasma collected from human donors reactive to *T. gondii*. High titer plasma or serum has traditionally served as a source of controls and/or calibrators (standards) in diagnostic assays and kits designed to monitor for the presence of human antibodies specific for a given antigen. These include tests to detect antibodies to human immunodeficiency virus-1, human immunodeficiency virus-2, human T-cell leukemia virus-1, human T-cell leukemia virus-2, cytomegalovirus, hepatitis A virus, hepatitis B virus, hepatitis C virus, hepatitis D virus, hepatitis E virus, respiratory syncytial virus, Rubella virus, *Toxoplasma gondii, Trypanosoma cruzi, Cryptococcus neoformans, Histoplasma capsulatum, Helicobacter pylon*, and *Streptococcus pyogenes*. Use of human seropositive plasma or serum for the manufacture of calibrators (standards) and/or controls has several significant drawbacks, including: (1) the increasing difficulty of sourcing large volumes of plasma or serum with high titer, high specificity, and that lack antibodies to other infectious agents, (2) considerable lot-to-lot variability over time with respect to titer and specificity which impacts the performance of the assay, (3) inherent limitations with respect to characterization of an antisera due to its polyclonal nature (heterogeneous in antibody class, specificity and affinity), and (4) cost. In fact, it is conceivable that, in some cases, it may be impossible to maintain production of calibrators and/or controls that are based on seropositive human plasma due to sourcing issues. It can be especially difficult to find high titer sources of IgM antibody as these are generally obtained from acutely infected individuals. For example, sourcing of IgM reactive to Rubella in the U.S. is difficult due to the successful vaccination program. As sourcing of suitable seropositive plasma or serum becomes more difficult, the costs related to manufacturing of calibrators and controls increase, and this economic burden is ultimately passed on to the patient. An alternative method for manufacture of calibrators (standards) and/or positive controls for diagnostic assays and kits designed to monitor levels of specific antibody would represent a significant advance.

Genetically engineered antibodies, such as mouse:human chimeric antibodies, can be used as quality control reagents for specificity testing of anti-human antibody conjugates and for quality control of human total immunoglobulin immunoassays. It was further proposed that these chimeric antibodies may be useful reagents for quantitation of specific antibody in reference standards. The chimeric antibodies would be used to establish a heterologous dose-response curve to interpolate the amount of antibody in a reference standard specific for a different antigen (Hamilton, R. G., Ann. Biol. Clin. 48:473–477 (1990); Butler, J. E. and Hamilton, R. G., In Immunochemistry of Solid-phase Immunoassay, Butler, J. E. ed., CRC Press, Boca Raton, pgs. 173–198 (1991)). The term "heterologous" indicates that the antigen for which the chimeric antibodies are specific is defined, but unrelated to the antigen to which specific antibody is being monitored.

The present invention differs from the aforementioned in two important ways: (1) the proposed reagents are intended to be used, as a substitute for seropositive plasma or serum, in the manufacture of calibrators (standards) and/or positive controls for immunoassays and kits designed to monitor antigen specific antibody responses, and (2) the proposed reagents bind to the same or "homologous" antigen to that which the specific antibody being measured binds. Use of reagents which bind to the homologous antigen is preferable in that the calibrator, positive control, and test specimen are reacted to the same antigen under identical conditions, providing a more realistic measure of specific antibody activity, and has the added advantage of allowing one to monitor the integrity of the test antigen at the time the assay is run.

One alternative source of material for the manufacture of positive controls in immunoassays designed to detect specific human antibody is non-human immune antibody that reacts with an anti-human antibody (U.S. Pat. No. 5,008, 183). Use of non-human immune (polyclonal) sera has several drawbacks including: (a) lot-to-lot variability over time with respect to antibody class composition, titer, specificity and affinity that can impact assay performance; (b) difficulty in characterization due to its polyclonal composition (e.g. heterogeneous affinity and specificity); (c) limited supply; and (d) in the case of infectious agents, potential biohazard if live organisms are used to immunize.

An alternative source of material for the manufacture of calibrators and controls for IgM assays is a composite antibody of a nonspecific IgM immunoglobulin moiety covalently linked to a specific non-IgM antibody moiety (U.S. Pat. No. 5,478,753). Use of immune sera to produce the composite antibody has all of the inherent drawbacks outlined above. In addition, one must source and purify both the immune and non-immune moieties used to construct the composite antibody. Moreover, the chemically crosslinked products would be heterogeneous with respect to the number and location of the attached non-immune antibody moieties. In fact, attachment near the binding site may result in steric interference of antigen binding by the specific antibody.

Use of the reagents described in the present invention, that bind to ligand, contain one or more constant region epitopes, and are homogeneous in specificity and affinity (i.e., all molecules are uniform with respect to the properties of specificity and affinity), circumvent all of the problems associated with using an immune sera in manufacture of calibrators and positive controls. Furthermore, since the constant region epitopes are an integral part of the reagent (i.e., directly fused to the ligand binding domain) a more uniform composition is obtained. Moreover, the present reagents can be readily and reproducibly generated in virtually unlimited quantities and are also useful for quantitating, and monitoring the integrity of, antigen used in the assay.

SUMMARY OF THE INVENTION

Traditionally, diagnostic assays and kits designed to detect the presence of human antibodies specific for a given antigen (e.g., human immunodeficiency virus-1, human immunodeficiency virus-2, human T-cell leukemia virus-1, human T-cell leukemia virus-2, cytomegalovirus, hepatitis A virus, hepatitis B virus, hepatitis C virus, hepatitis D virus, hepatitis E virus, hepatitis GB virus, respiratory syncytial virus, Rubella virus, *Toxoplasma gondii, Trypanosoma cruzi, Cryptococcus neoformans, Histoplasma capsulatum, Helicobacter pylori*, and *Streptococcus pyogenes*) have used seropositive human plasma (polyclonal antibody) or serum to manufacture calibrators (standards) and controls. In contrast, the present invention relates to a method of using reagents as calibrators (standards) and/or controls in such diagnostic assays and kits in place of such plasma or serum. More specifically, one or more of these reagents may be used in the place of seropositive plasma or serum as calibrators (standards) and/or controls for diagnostic assays and kits designed to qualitatively or quantitatively measure antibodies specific for a desired ligand. The reagents themselves bind specifically to a predetermined ligand, contain one or more antibody constant region epitopes, and are homogeneous or uniform in specificity and affinity. The agents may be produced by the use of hybridoma and/or recombinant DNA technology.

More specifically, the present invention encompasses a method for detecting the presence of antibody which may be present in a test sample wherein this method comprises (a) contacting the test sample suspected of containing the antibody with antigen specific for the antibody for a time and under conditions sufficient to allow the formation of antigen/antibody complexes, (b) detecting the presence of the antibody which may be present in the test sample, and (c) employing, as a control or calibrator, a reagent which binds to the antigen, wherein the improvement comprises employing, as the control or calibrator, a reagent comprising one or more antibody constant region epitopes, wherein the reagent binds to the antigen and is homogeneous with respect to specificity and affinity.

The invention also includes a method for detecting the presence of antibody which may be present in a test sample wherein the method comprises (a) contacting the test sample suspected of containing the antibody with antigen specific for the antibody for a time and under conditions sufficient to allow the formation of antigen/antibody complexes, (b) detecting the presence of the antibody which may be present in the test sample, and (c) employing, as a control or calibrator, two or more reagents which bind to the antigen, wherein the improvement comprises employing, as the control or calibrator, two or more reagents each comprising one or more antibody constant region epitopes, wherein each of the two or more reagents binds to different epitopes on said antigen and is homogeneous with respect to specificity and affinity.

Furthermore, the invention encompasses a method for detecting the presence of antibody which may be present in a test sample wherein the method comprises (a) contacting the test sample suspected of containing the antibody with antigen specific for the antibody for a time and under conditions sufficient to allow the formation of antigen/antibody complexes, (b) adding a direct or indirect conjugate to the resulting antigen/antibody complexes for a time and under conditions sufficient to allow the conjugate to bind to the bound antibody, wherein the conjugate comprises an antibody attached to a signal generating compound capable of generating a detectable signal, (c) detecting the presence of the antibody which may be present in the test sample by detecting the signal generated by the signal generating compound, and (d) employing, as a control or calibrator, a reagent which binds to the antigen, wherein the improvement comprises employing, as said control or calibrator, a reagent comprising one or more antibody constant region epitopes, wherein the reagent binds to the antigen and is homogeneous with respect to specifity and affinity.

The present invention additionally includes a method for detecting the presence of antibody which may be present in a test sample wherein the method comprises (a) contacting the test sample suspected of containing the antibody with antigen specific for the antibody for a time and under conditions sufficient to allow the formation of antigen/antibody complexes, (b) adding a direct or indirect conjugate to the resulting antigen/antibody complexes for a time and under conditions sufficient to allow the conjugate to bind to the bound antibody, wherein said conjugate comprises an antibody attached to a signal generating compound capable of generating a detectable signal, (c) detecting the presence of the antibody which may be present in said test sample by detecting the signal generated by the signal generating compound, and (d) employing, as a control or calibrator, two or more reagents which bind to the antigen, wherein the improvement comprises employing, as the control or calibrator, two or more reagents each comprising one or more antibody constant region epitopes, wherein each of the two or more reagents binds to different epitopes on the antigen and is homogeneous with respect to specificity and affinity.

In all of the above methods, the reagent may be selected from the group consisting of a chimeric monoclonal antibody comprising H and L chain variable regions from one host species fused to constant region genes derived from the same host species as the antibody being measured, a monoclonal antibody derived from the same host species as the antibody being measured, a monoclonal antibody derived from a species related on the basis of immunologic cross-reactivity to that being assayed, and a polypeptide fused to an antibody constant region or a fragment thereof derived from the same host species as the antibody being measured or related to the host species on the basis of immunologic cross-reactivity. The chimeric monoclonal antibody may comprise H and L chain variable regions derived from a rodent and H and L chain constant region genes derived from a human. Additionally, the chimeric monoclonal antibody may bind specifically to *Toxoplasma gondii* and more specifically to proteins P30 or P66 thereof.

In the methods involving one reagent, the H chain variable region of the chimeric monoclonal antibody, if such is the reagent, may be encoded by the nucleotide sequence shown in FIG. 6 or allelic variations thereof, and the L chain variable region of the chimeric monoclonal antibody may be encoded by the nucleotide sequence shown in FIG. 7 or allelic variations thereof. The H chain variable region of the chimeric monoclonal antibody may have the amino acid sequence shown in FIG. 6, and the L chain variable region of the chimeric monoclonal antibody may have the amino acid sequence shown in FIG. 7.

Alternatively, the H chain variable region of the chimeric monoclonal antibody may be encoded by the nucleotide sequence shown in FIG. 8 or allelic variations thereof, and the L chain variable region of the chimeric monoclonal antibody may be encoded by the nucleotide sequence shown in FIG. 9 or allelic variations thereof. The H chain variable region of the chimeric monoclonal antibody may have the amino acid sequence shown in FIG. 8, and the L chain variable region of the chimeric monoclonal antibody may have the amino acid sequence shown in FIG. 9.

In the methods above involving more than one reagent, wherein each is a chimeric monoclonal antibody, the H chain variable region representing one of the two or more reagents may be encoded by the nucleotide sequence shown in FIG. 6 or allelic variations thereof, and the L chain variable region of the chimeric monoclonal antibody representing the same one of the two or more reagents may be encoded by the nucleotide sequence shown in FIG. 7 or allelic variations thereof, and the H chain variable region of the chimeric monoclonal antibody representing another of the two or more reagents may be encoded by the nucleotide sequence shown in FIG. 8 or allelic variations thereof and the L chain variable region of this other of the two or more reagents may be encoded by the nucleotide sequence shown in FIG. 9 or allelic variations thereof.

The H chain variable region of the chimeric monoclonal antibody representing one of the two or more reagents has the amino acid sequence shown in FIG. 6 and the L chain variable region of the chimeric monoclonal antibody representing the one of the two or more reagents may have the amino acid sequence shown in FIG. 7, and the H chain variable region of the chimeric monoclonal antibody representing another of this two or more reagents may have the amino acid sequence shown in FIG. 8 and the L chain variable region of this other of the two or more reagents may have the amino acid sequence shown in FIG. 9.

In the above methods, the antibody to be detected in the test sample is selected from the group consisting of IgA, IgD, IgE, IgG, and IgM. The antigen may be selected from the group consisting of an infectious agent, an autoantigen, an allergen, and a pharmaceutical compound. The infectious agent may be selected from the group consisting of a parasite, a bacterium, a fungus, a yeast and a virus. More specifically, the virus may be selected from the group consisting of: human immunodeficiency virus-1, human immunodeficiency virus-2, human T-cell leukemia virus-1, human T-cell leukemia virus-2, cytomegalovirus, hepatitis A virus, hepatitis B virus, hepatitis C virus, hepatitis D virus, hepatitis E virus, hepatitis GB virus, respiratory syncytial virus, and Rubella virus. The parasite may be selected from the group consisting of *Toxoplasma gondii* and *Trypanosoma cruzi*. The fungus may be selected from the group consisting of *Histoplasma capsulatum* and *Cryptococcus neoformans*, and the bacterium may be selected from the group consisting of *Helicobacter pylori* and *Streptococcus pyogenes*.

The present invention also encompasses a kit for determining the presence of antibody in a test sample comprising:

a) an antigen specific for the antibody; and b) a control or calibrator comprising a reagent wherein the reagent comprises one or more antibody constant region epitopes, binds to the antigen, and is homogeneous with respect to specifity and affinity.

The invention also includes a kit for determining the presence of antibody in a test sample comprising: a) an antigen specific for the antibody; and b) a control or calibrator comprising two or more reagents wherein each of the two or more reagents comprises one or more antibody constant region epitopes, binds to different epitopes on said antigen, and is homogeneous with respect to specifity and affinity.

Additionally, the invention includes a kit for determining the presence of antibody in a test sample comprising: a) an antigen specific for the antibody; b) a direct or indirect conjugate comprising an antibody attached to a signal generating compound capable of generating a detectable signal; and c) a control or calibrator comprising a reagent wherein the reagent comprises one or more antibody constant region epitopes, binds to the antigen, and is homogeneous with respect to specifity and affinity.

Furthermore, the invention includes a kit for determining the presence of antibody in a test sample comprising: a) an antigen specific for the antibody; b) a direct or indirect conjugate comprising an antibody attached to a signal generating compound capable of generating a detectable signal; and c) a control or calibrator comprising two or more reagents wherein each of the two or more reagents comprises one or more antibody constant region epitopes, binds to different epitopes on the antigen, and is homogeneous with respect to specificity and affinity.

In all of the above kits, the reagent may be selected from the group consisting of a chimeric monoclonal antibody comprising H and L chain variable regions from one host species fused to constant region genes derived from the same host species as the antibody being measured, a monoclonal antibody derived from the same host species as the antibody being measured, a monoclonal antibody derived from a species related on the basis of immunologic cross-reactivity to that being assayed, and a polypeptide fused to an antibody constant region or a fragment thereof derived from the same host species as the antibody being measured or related to the host species on the basis of immunologic cross-reactivity.

When the reagent is a chimeric monoclonal antibody, it comprises H and L chain variable regions derived from a rodent and H and L chain constant region genes derived from a human.

Furthermore, the antibody to be detected may be selected from the group consisting of IgA, IgD, IgE, IgG, and IgM. The antigen of the kits may be selected from the group consisting of an infectious agent, an autoantigen, an allergen, and a pharmaceutical compound. The infectious agent may be selected from the group consisting of a parasite, a bacterium, a fungus, a yeast and a virus. More specifically, the virus may be selected from the group consisting of: human immunodeficiency virus-1, human immunodeficiency virus-2, human T-cell leukemia virus-1, human T-cell leukemia virus-2, cytomegalovirus, hepatitis A virus, hepatitis B virus, hepatitis C virus, hepatitis D virus, hepatitis E virus, hepatitis GB virus, respiratory syncytial virus and Rubella virus. The parasite may be selected from the group consisting of *Toxoplasma gondii* and *Trypanosoma cruzi*. The fungus may be selected from the group consisting *Histoplasma capsulatum* and *Cryptococcus neoformans*, and the bacterium may be selected from the group consisting of *Helicobacter pylori* and *Streptococcus pyogenes*.

Additionally, the present invention includes a method for detecting the presence of antibody which may be present in a test sample wherein the method comprises (a) contacting the test sample suspected of containing the antibody with anti-antibody specific for the antibody for a time and under conditions sufficient to allow the formation of anti-antibody/antibody complexes, (b) detecting the presence of the antibody which may be present in the test sample, and (c) employing, as a control or calibrator, a reagent which binds to the anti-antibody, wherein the improvement comprises employing, as the control or calibrator, a reagent comprising one or more antibody constant region epitopes, wherein the reagent binds to said antigen and is homogeneous with respect to specifity and affinity.

The invention also includes a method for detecting the presence of antibody which may be present in a test sample wherein the method comprises (a) contacting the test sample suspected of containing the antibody with anti-antibody specific for the antibody for a time and under conditions sufficient to allow the formation of anti-antibody/antibody complexes, (b) detecting the presence of the antibody which may be present in the test sample, and (c) employing, as a control or calibrator, two or more reagents which bind to the anti-antibody, wherein the improvement comprises employing, as the control or calibrator, two or more reagents each comprising one or more antibody constant region epitopes, wherein each of the two or more reagents binds to different epitopes on the antigen and is homogeneous with respect to specificity and affinity.

Additionally, the present invention includes a method for detecting the presence of antibody which may be present in a test sample wherein the method comprises (a) contacting the test sample suspected of containing the antibody with anti-antibody specific for the antibody for a time and under conditions sufficient to allow the formation of anti-antibody/antibody complexes, (b) adding a conjugate to the resulting anti-antibody/antibody complexes for a time and under conditions sufficient to allow the conjugate to bind to the bound antibody, wherein the conjugate comprises an antigen attached to a signal generating compound capable of generating a detectable signal, (c) detecting the presence of the antibody which may be present in the test sample by detecting the signal generated by the signal generating compound, and (d) employing, as a control or calibrator, a reagent which comprises antibody to the anti-antibody, wherein the improvement comprises employing, as the control or calibrator, a reagent comprising one or more antibody constant region epitopes, wherein the reagent binds to the antigen and is homogeneous with respect to specifity and affinity.

Furthermore, another method of the invention for detecting the presence of antibody which may be present in a test sample comprises (a) contacting the test sample suspected of containing the antibody with anti-antibody specific for the antibody for a time and under conditions sufficient to allow the formation of anti-antibody/antibody complexes, (b) adding a conjugate to the resulting anti-antibody/antibody complexes for a time and under conditions sufficient to allow the conjugate to bind to the bound antibody, wherein the conjugate comprises an antigen attached to a signal generating compound capable of generating a detectable signal, (c) detecting the presence of the antibody which may be present in the test sample by detecting the signal generated by the signal generating compound, and (d) employing, as a control or calibrator, two or more reagents which bind to the anti-antibody, wherein the improvement comprises employing, as the control or calibrator, two or more reagents each comprising one or more antibody constant region epitopes, wherein each of the two or more reagents binds to different epitopes on the antigen and has a unique specificity and affinity.

In the methods presented directly above, the reagent may be selected from the group consisting of a chimeric monoclonal antibody comprising H and L chain variable regions from one host species fused to constant region genes derived from the same host species as the antibody being measured, a monoclonal antibody derived from the same host species as the antibody being measured, a monoclonal antibody derived from a species related on the basis of immunologic cross-reactivity to that being assayed, and a polypeptide fused to an antibody constant region or a fragment thereof derived from the same host species as the antibody being measured or related to the host species on the basis of immunologic cross-reactivity.

If the reagent is a chimeric monoclonal antibody, it comprises H and L chain variable regions derived from a rodent and H and L chain constant region genes derived from a human. The chimeric monoclonal antibody may bind specifically to *Toxoplasma gondii*. More specifically, the chimeric monoclonal antibody may bind to protein P30 or protein P66 of *Toxoplasma gondii*.

In the methods involving one reagent, where the reagent is a chimeric monoclonal antibody, the H chain variable region of the chimeric monoclonal antibody may be encoded by the nucleotide sequence shown in FIG. 6 or allelic variations thereof, and the L chain variable region of the chimeric monoclonal antibody may be encoded by the nucleotide sequence shown in FIG. 7 or allelic varaitions thereof. The H chain variable region of the chimeric monoclonal antibody may have the amino acid sequence shown in FIG. 6, and the L chain variable region of the chimeric monoclonal antibody may have the amino acid sequence shown in FIG. 7.

Alternatively, the H chain variable region of the chimeric monoclonal antibody may be encoded by the nucleotide sequence shown in FIG. 8 or allelic variations thereof, and the L chain variable region of the chimeric monoclonal antibody may encoded by the nucleotide sequence shown in FIG. 9 or allelic variations thereof. The H chain variable region of the chimeric monoclonal antibody may have the amino acid sequence nucleotide shown in FIG. 8, and the L chain variable region of the chimeric monoclonal antibody may have the amino acid sequence shown in FIG. 9.

In the methods where more than one reagent is involved, the H chain variable region of the chimeric monoclonal antibody representing one of the two or more reagents may be encoded by the nucleotide sequence shown in FIG. 6 or allelic variations thereof and the L chain variable region of the chimeric monoclonal antibody representing that one of the two or more reagents may be encoded by the nucleotide sequence shown in FIG. 7 or allelic variations thereof, and the H chain variable region of the chimeric monoclonal antibody representing another of the two or more reagents may be encoded by the nucleotide sequence shown in FIG. 8 or allelic variations thereof and the L chain variable region of this other of the two or more reagents may be encoded by the nucleotide sequence shown in FIG. 9 or allelic variations thereof. The H chain variable region of the chimeric monoclonal antibody representing one of the two or more reagents may have the amino acid sequence shown in FIG. 6 and the L chain variable region of the chimeric monoclonal antibody representing this one of the two or more reagents may have the amino acid sequence shown in FIG. 7, and the H chain variable region of the chimeric monoclonal antibody representing another of the two or more reagents may have the amino acid sequence shown in FIG. 8 and the L chain variable region of this other of the two or more reagents may have the amino acid sequence shown in FIG. 9.

The antibody to be detected in said test sample may be selected from the group consisting of IgA, IgD, IgE, IgG, and IgM. The antigen may be selected from the group consisting of an infectious agent, an autoantigen, an allergen, and a pharmaceutical compound. The infectious agent may be selected from the group consisting of a parasite, a bacterium, a fungus, a yeast and a virus. More specifically, the virus may be selected from the group consisting of: human immunodeficiency virus-1, human immunodeficiency virus-2, human T-cell leukemia virus-1, human T-cell leukemia virus-2, cytomegalovirus, hepatitis A virus, hepatitis B virus, hepatitis C virus, hepatitis D virus, hepatitis E virus, hepatitis GB virus, respiratory syncytial virus, and Rubella virus. The parasite may be selected from the group consisting of *Toxoplasma gondii* and *Trypanosoma cruzi*. The fungus may be selected from the group consisting of *Histoplasma capsulatum* and *Cryptococcus neoformans*, and the bacterium may selected from the group consisting of *Helicobacter pylori* and *Streptococcus pyogenes*.

The invention also includes a kit for determining the presence of antibody in a test sample comprising: a) an anti-antibody specific for the antibody; b) an antigen specific for the antibody; and c) a control or calibrator comprising a reagent wherein the reagent comprises one or more antibody constant region epitopes, binds to the antigen, and is homogeneous with respect to specifity and affinity.

Additionally, the invention includes a kit for determining the presence of antibody in a test sample comprising: a) an anti-antibody specific for the antibody; b) an antigen specific for the antibody; and c) a control or calibrator comprising two or more reagents wherein each of the two or more reagents comprises one or more antibody constant region epitopes, binds to different epitopes on said antigen, and is homogeneous with respect to specifity and affinity.

Furthermore, the invention encompasses a kit for determining the presence of antibody in a test sample comprising: a) an anti-antibody specific for the antibody; b) a direct or indirect conjugate comprising an antigen attached to a signal generating compound capable of generating a detectable signal; and c) a control or calibrator comprising a reagent wherein the reagent comprises one or more antibody constant region epitopes, binds to the antigen, and is homogeneous with respect to specifity and affinity.

The invention also includes a kit for determining the presence of antibody in a test sample comprising: a) an anti-antibody specific for the antibody; b) a direct or indirect conjugate comprising an antigen attached to a signal generating compound capable of generating a detectable signal; and c) a control or calibrator comprising two or more reagents wherein each of the two or more reagents comprises one or more antibody constant region epitopes, binds to different epitopes on said antigen, and is homogeneous with respect to specificity and affinity.

In the kits directly above, the reagent may be selected from the group consisting of a chimeric monoclonal antibody comprising H and L chain variable regions from one host species fused to constant region genes derived from the same host species as the antibody being measured, a monoclonal antibody derived from the same host species as the antibody being measured, a monoclonal antibody derived from a species related on the basis of immunologic cross-reactivity to that being assayed, and a polypeptide fused to an antibody constant region or a fragment thereof derived from the same host species as the antibody being measured or related to the host species on the basis of immunologic cross-reactivity.

If a chimeric monoclonal antibody is the reagent in each of the kits, it comprises H and L chain variable regions derived from a rodent and H and L chain constant region genes derived from a human.

The antibody to be detected in test sample may be selected from the group consisting of IgA, IgD, IgE, IgG and IgM. The antigen is selected from the group consisting of an infectious agent, an autoantigen, an allergen, and a pharmaceutical compound. The infectious agent may be selected from the group consisting of a parasite, a bacterium, a fungus, a yeast and a virus. More specifically, the virus may be selected from the group consisting of: human immunodeficiency virus-1, human immunodeficiency virus-2, human T-cell leukemia virus-1, human T-cell leukemia virus-2, cytomegalovirus, hepatitis A virus, hepatitis B virus, hepatitis C virus, hepatitis D virus, hepatitis E virus, hepatitis GB virus, respiratory syncytial virus and Rubella virus. The parasite may be selected from the group consisting of *Toxoplasma gondii* and *Trypanosoma cruzi*. The fungus may be selected from the group consisting of *Histoplasma capsulatum* and *Cryptococcus neoformans*, and the bacterium may be selected from the group consisting of *Helicobacter pylori*, and *Streptococcus pyogenes*.

The invention also encompasses a method for detecting the presence of antibodies, developed against more than one antigen, which may be present in a test sample wherein the method comprises (a) contacting the test sample suspected of containing the antibodies with antigens specific for the antibodies, respectively, for a time and under conditions sufficient to allow the formation of antigen/antibody complexes, (b) adding direct or indirect conjugates to the antigen/antibody complexes for a time and under conditions sufficient to allow the conjugates to bind to the bound antibodies, wherein the conjugates comprise an antibody attached to a signal generating compound capable of generating a detectable signal, (c) detecting the presence of the antibodies which may be present in the test sample by detecting the signal generated by the signal generating compound, and (d) employing, as controls or calibrators, reagents which bind to the antigens, wherein the improvement comprises employing, as the controls or calibrators, reagents, each comprising one or more antibody constant region epitopes, wherein each of the reagents bind to said antigens, respectively, and is homogeneous with respect to specificity and affinity.

Each of the reagents may be selected from the group consisting of a chimeric monoclonal antibody comprising H and L chain variable regions from one host species fused to constant region genes derived from the same host species as the antibody being measured, a monoclonal antibody derived from the same host species as the antibody being measured, a monoclonal antibody derived from a species related on the basis of immunologic cross-reactivity to that being assayed, and a polypeptide fused to an antibody constant region or a fragment thereof derived from the same host species as the antibody being measured or related to the host species on the basis of immunologic cross-reactivity.

The features noted above with respect to all of the other methods apply to this method as well.

The invention also includes a kit for determining the presence of antibodies, developed against more than one antigen, which may be present in a test sample, comprising: a) antigens specific for the antibodies, respectively; b) direct or indirect conjugates each comprising an antibody attached to a signal generating compound capable of generating a detectable signal; and c) controls or calibrators comprising reagents wherein each of the reagents comprises one or more antibody constant region epitopes, bind to the respective antigens, and is homogeneous with respect to specificity and affinity.

In this kit, each of the reagents may be selected from the group consisting of a chimeric monoclonal antibody comprising H and L chain variable regions from one host species fused to constant region genes derived from the same host species as the antibody being measured, a monoclonal antibody derived from the same host species as the antibody being measured, a monoclonal antibody derived from a species related on the basis of immunologic cross-reactivity to that being assayed, and a polypeptide fused to an antibody constant region or a fragment thereof derived from the same host species as the antibody being measured or related to the host species on the basis of immunologic cross-reactivity.

The features noted above with respect to the other kits apply to this kit as well.

BRIEF DESCRIPTION OF THE DRAWINGS

FIG. 6 illustrates the nucleotide sequence of the $V_H$ cassette containing the $V_H$ cDNA cloned from hybridoma 5-465-210 (see SEQ ID NO:2). The educed amino acid sequence is indicated by a single letter symbol below (see SEQ ID NO:1). The first amino acid of the mature protein is designated (+1), the splice point of $J_H2$ to the constant region is indicated by the arrow, and the complementarity determining regions (CDRs) as defined by Kabat E. A. et.al., (Sequences of Proteins of Immunological Interest, 5th edition, U.S. Department of Health and Human Services, Bethesda, Md. (1991)) are indicated. The degenerate sense primer used to PCR amplify this $V_H$ fragment from cDNA extended to nucleotide 41. Other features of note: (1–39), sense transfer primer with cloning site (Xho I); (16–72), leader sequence; (73–366), H chain V-gene; (367–384), H chain D segment; (385–429), H chain $J_H2$-minigene; (430–447), splice site sequence and Hind III cloning site derived from the antisense transfer primer.

FIG. 7 represents the nucleotide sequence of the $V_L$ cassette containing the Vκ cDNA cloned from hybridoma 5-465-210 (see SEQ ID NO:4). The deduced amino acid sequence is indicated by a single letter symbol (see SEQ ID NO:3). The first amino acid of the mature protein is designated (+1), the splice point of Jκ2 and the Cκ gene is indicated by the arrow, and CDRs designated as in FIG. 6 are indicated. The sense primer used to PCR amplify the Vκ region from cDNA extended to position 45. Additional sequences of note: (1–40), sense transfer primer sequences including the Xba I cloning site; (17–76), leader sequence; (77–373), κ chain V-gene; (374–409), Jκ-minigene; (410–428), splice site sequence and Bam HI cloning site incorporated into the antisense transfer primer.

FIG. 8 shows the nucleotide sequence of the $V_H$ cassette containing the $V_H$ cDNA cloned from the hybridoma 1-706-139 (see SEQ ID NO:6). The deduced amino acid sequence is shown by a single letter symbol (see SEQ ID NO:5). The first amino acid of the mature protein is designated (+1), the splice junction between $J_H4$ and the constant region is marked with an arrow, and CDRs determined as in FIG. 6 are indicated. The degenerate primer (sense) used to PCR amplify the $V_H$ cDNA extended to position 41. Additional noteworthy features include: (1–35), sense transfer primer including the Xho I cloning site and the 5' end of the leader sequence, (12–68) leader sequence; (69–362), H chain V-gene; (363–380), presumed D-minigene sequence*; (381–434), $J_H4$-minigene; (434–452) splice and Hind III cloning sites incorporated into the antisense transfer primer. *The exact boundary between the D and J-minigenes could not be determined.

FIG. 9 represents the nucleotide sequence of the $V_L$ cassette containing the Vκ region cloned from hybridoma 1-706-139 (see SEQ ID NO:8). The deduced amino acid sequence is given in the single letter format (see SEQ ID NO:7). The first amino acid of the mature protein is indicated (+1), the splice point between the Jκ1-minigene and the CK gene is identified with an arrow, and CDRs determined as in FIG. 6 are designated. The 3' terminus of the degenerate sense primer used for PCR amplification of the Vκ region from cDNA is at position 42. Other features include: (1–39), sense transfer primer sequence incorporating the Xba I cloning site and 5' leader sequences; (13–69) leader sequences; (70–368), κ V-gene; (369–405), Jκ1-minigene; (406–424), splice and Bam HI cloning sites incorporated into the antisense transfer primer.

DETAILED DESCRIPTION OF THE INVENTION

Figure 1:
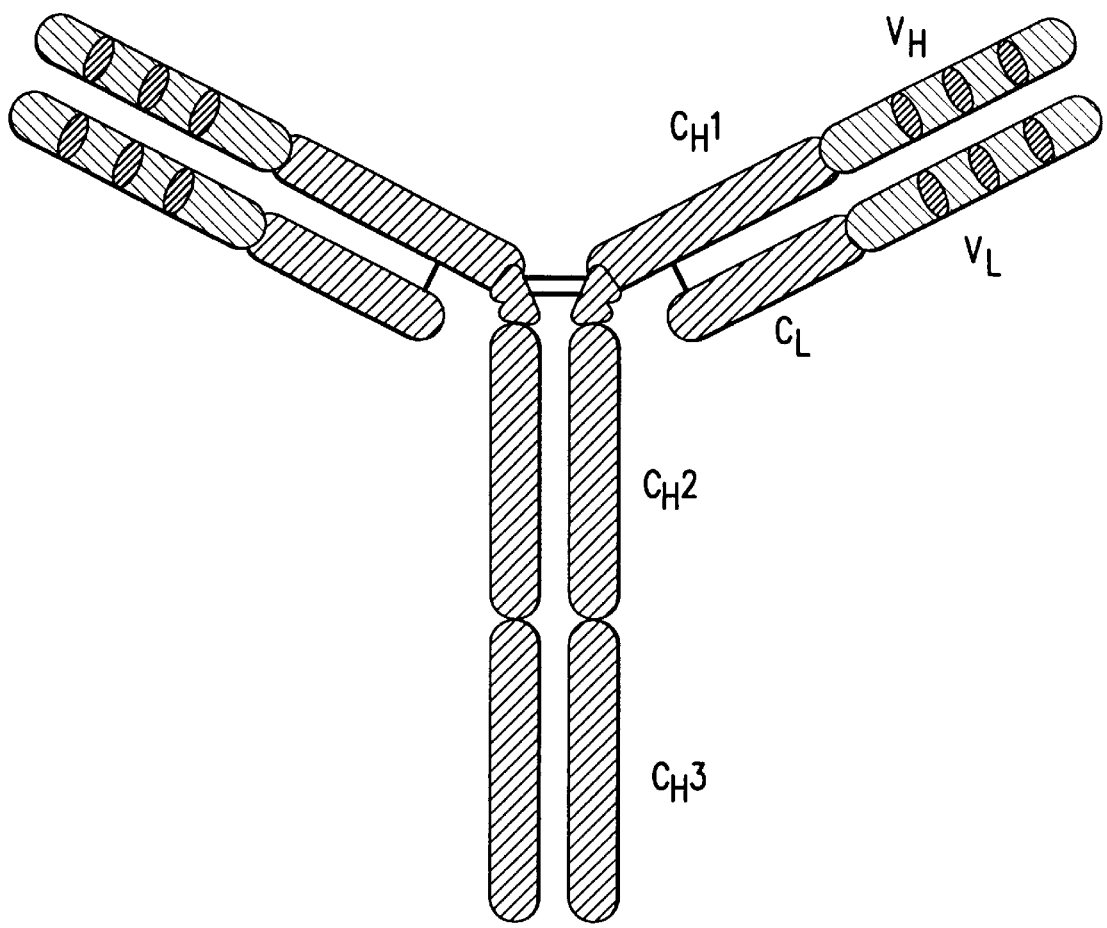
FIG. 1 illustrates the basic structure of an antibody molecule. The two identical heavy (H) chains are composed of either four or five domains (depending on the class of the antibody) and a hinge region, while the light (L) chains are composed of two domains. The amino terminal domain of the H and L chains is referred to as the variable (V) region and is responsible for antigen binding activity. The other domains present in the H and L chain constitute the constant region. This is a depiction of a mouse-human chimeric antibody as mouse V regions are joined to human constant regions.

The present invention relates to a method of using reagents as calibrators (standards) and/or controls in diagnostic kits and assays. More specifically, one or more of these reagents may be used in place of plasma or serum in the production of calibrators and controls for diagnostic kits and assays designed to qualitatively or quantitatively measure antibodies specific for a desired ligand. The reagents themselves bind specifically to a predetermined ligand, contain one or more antibody constant region epitopes, and are uniform in specificity and affinity. The reagents may be produced continually by the use of hybridoma and/or recombinant DNA technology.

There are several embodiments of the above-identified reagent. These embodiments are, for example, as follows:

1) a chimeric monoclonal antibody comprising H and L chain variable regions from one host species fused to the constant region genes derived from the same host species as the antibody being measured;
2) a monoclonal antibody derived from the same host species as the antibody being measured;
3) a monoclonal antibody derived from a species related on the basis of immunologic cross-reactivity to that being assayed; and
4) a polypeptide which binds specifically to a predetermined ligand fused to an antibody constant region or some part of a constant region of the desired host species.

The above-listed embodiments are described in detail below:

1) Chimeric Monoclonal Antibodies:

In this embodiment of the invention, the reagent(s) used as a calibrator or control in the diagnostic assay or kit is a chimeric monoclonal antibody molecule comprising H and L chain V regions from one host species fused to H and L chain constant region genes from another host species. The H and L chain V regions may be derived from any vertebrate that produces antibody, including but not limited to: rodent (e.g., mouse, hamster, rat), chicken, rabbit, canine, feline, bovine, equine, porcine, ape (e.g. chimpanzee), and human. The source of the antibody V regions, and method by which they are derived is based primarily on convenience and technology known to those of ordinary skill in the art. For example, the H and L chain V regions (comprising the part of the antibody molecule responsible for ligand binding activity) may be isolated from: single B cells, B cell hybridomas, B cells propagated in vitro, or B cells propagated in vivo, for example, human B cells in SCID mice (Simonsson, A. C. et. al., Bio/Techniques 18(5):862–869 (1995); Banchereau, J. et. al., Science 251:70–72 (1991); Amoroso, K. and Lipsky, P. E., J. Immunol. 145:3155–3161 (1990); Duchosal, M. A. et. al., Nature 355:258–262 (1992)). Antibody V regions may be cloned by standard procedures known in the art, or modifications of these procedures. For instance, the V regions may be cloned according to the process described in Example III below.

Alternatively, antibody H and L chain V region sets with desired binding activity may be screened for by expression as, for example, Fab fragments (heterodimers of $V_H$ and the first domain of the heavy chain constant region, and the complete light chain), Fv fragments (heterodimers of the H and L chain V region domains), or single-chain Fv (heterodimers of $V_H$ and $V_L$ domains connected by a peptide linker), in bacteria, e.g. *E. coli*, or selected through the use of combinatorial libraries expressed in lambda phage, on the surface of bacteriophage, on the surface of bacteria, or screened by display on any other biological (e.g. retrovirus or polysome) or non-biological system (Better, M. et. al., Science, 240:1041–1043 (1988); Skerra, A. and Pluckthun, A., Science, 240:1038–1041 (1988); Huse, W. D. et. al., Science 246:1275–1281 (1989); McCafferty, J. et. al., Nature 348:552–554 (1990); Kang, A. S. et. al., Proc. Natl. Acad. Sci. USA 88: 4363–4366 (1991); Fuchs P. et. al., Bio/Technology 9:1369–1372 (1991); Francisco, J. et. al., Proc. Natl. Acad. Sci. USA 90:10444–10448 (1993); Mattheakis, L. C. et. al., Proc. Natl. Acad. Sci. USA 91:9022–9026 (1994)). The libraries may be composed of: native V regions isolated from an immunized or unimmunized host, synthetic or semi-synthetic V regions, or modified V regions (Marks, J. D. et. al., J. Mol. Biol. 222:581–597 (1991); Barbas, C. F. III et. al., Proc. Natl. Acad. Sci. USA 89:4457–4461 (1992)). Examples of the latter include fine-tuning of specificity and/or affinity by in vitro mutagenesis.

The most critical property of the antibody V region combination (H and L) is that it forms a binding site with the desired properties of specificity and affinity for the ligand. Required specificity and affinity will be dictated by the intended use, and dependent upon such characteristics as assay format and desired performance characteristics (e.g. sensitivity, specificity, precision, and parallelism). For example, if one requires a calibrator or control antibody specific for one particular immunodominant epitope (ligand) on an antigen, to mimic the serologic response in vivo, the H and L chain V region set used to generate the chimeric antibody can be chosen on this basis.

Antibody constant region genes may be derived from any vertebrate species including but not limited to rodent (e.g., mouse, hamster, rat), chicken, rabbit, canine, feline, bovine, equine, porcine, ape (e.g. chimpanzee), and human. The choice of host species is dictated by the intended purpose. The antibody constant region is derived from the same host species, or one that is closely related, to the antibody being measured.

Chimeric monoclonal antibodies can be produced through the use of recombinant DNA techniques. For example, chimeric antibodies can be generated by targeted homologous recombination (Pell, H. P. et. al., Proc. Natl. Acad. Sci. USA 86:8507–8511 (1989)). Alternatively, antibody H and L chain V region genes may be cloned into a mammalian expression vector(s) containing antibody H and L chain constant region genes derived from a different host species. Introduction of the expression construct(s) into appropriate host cells results in production of complete chimeric antibodies of a defined specificity (Morrison, S. L. etal., Proc. Natl. Acad. Sci. USA 81: 6851–6855 (1984)). Many eukaryotic antibody expression vectors that are either stably integrated or exist as extrachromosomal elements have been described and are known to those of ordinary skill in the art. The H and L chain transcription units can be introduced into the host cell individually on separate plasmids or together on the same vector.

One example of an antibody expression vector is the plasmid, pdHL2 (FIG. 3), which contains human IgG1 (hu Cγ1) and human kappa constant region (hu Cκ) genes in their genomic configuration (Gillies, S. D. et al., J. Immunol. Methods 125:191–202 (1989)). Both transcription units contain an upstream immunoglobulin H chain enhancer element ($E_H$) and mouse metallothionein I promoter. Insertion of Vκ region and $V_H$ region cassettes results in expression of complete antibody. Each V gene cassette includes a 5' immunoglobulin leader sequence and a splice donor site 3' of the V gene. The vector also contains a bacterial origin of replication and β-lactamase gene derived from the plasmid pBR322 and an altered mouse dihydrofolate reductase (DHFR) gene under the control of the SV40 early region enhancer, promoter and polyadenylation signal sequences. The DHFR marker gene allows for selection and amplification in mammalian cells with methotrexate.

Expression vectors used to produce chimeric antibodies may be modified to contain any constant region gene(s) (for example in humans: κ, λ, IgM, IgD, IgG1, IgG2, IgG3, IgG4, IgA1, IgA2, IgE) isolated from any vertebrate species that makes antibodies, including but not limited to: rodent (e.g., mouse, hamster, rat), chicken, rabbit, canine, feline, bovine, equine, porcine, ape (e.g. chimpanzee), and human. By definition, the host species from which the H and L chain V regions are derived will be different than that from which the antibody constant regions are derived.

Depending on the vector system utilized, many different immortalized cell lines may serve as suitable hosts, these include but are not limited to: myeloma (e.g. X63-Ag8.653), hybridoma (Sp2/0-Ag14), lymphoma and Chinese Hamster Ovary (CHO) cells. Expression constructs can be introduced using a variety of 20 techniques, including but not limited to, calcium phosphate precipitation, protoplast fusion, lipofection, retrovirus-derived shuttle vectors, and electroporation. Proper expression leads to secretion of the recombinant antibody into the medium. Alternatively, cells may be lysed and antibody subsequently purified.

Chimeric antibody molecules or fragments thereof could also be produced in other systems, including but not limited to: baculovirus, yeast, bacteria such as *E. coli*, and in vitro in cell-free systems such as rabbit reticulocyte lysate (Hasemann, C. and Capra, J. D. Proc. Natl. Acad. Sci. USA 87:3942–3946 (1990); Horwitz, A. H. et. al., Proc. Natl. Acad. Sci. USA 85:8678–8682 (1988); Pluckthun, A., Bio/Technology 9:545–551 (1991); Nicholls et. al., J. Biol. Chem. 268(7):5302–5308 (1993)).

In summary, a chimeric monoclonal antibody comprises at least two (e.g., IgG) and up to 10 (e.g. pentameric IgM) identical binding sites derived from the H and L chain V regions of one host species joined to the H and L chain antibody 35 constant regions of another host species. The H and L chain V regions are responsible for the specificity and affinity of binding to the desired ligand. The source of the H and L chain constant regions is determined by the host species of antibody to be measured, in that it is preferably identical to it. The constant regions have no ligand-binding activity, but provide serologically identifiable epitopes (ligands) specific to the particular constant region, thus providing a means to discriminate it from other constant regions. Expression of the H and L chain genes encoding the chimeric antibodies in, for example, an immortalized host cell such as Sp2/0-Ag14, results in production of monoclonal chimeric antibody of predetermined and uniform specificity and affinity. Thus, a continuous source of chimeric antibody with V regions of a single defined binding specificity, and H and L chain constant region epitopes, is provided. One or more of these reagents would be useful as calibrators and/or controls in diagnostic assays and kits designed to qualitatively or quantitatively measure levels of specific antibody.

One particular example of this embodiment is a recombinant chimeric antibody containing murine H and L chain V regions fused to human H and L chain constant regions for use as a calibrator and/or control. This embodiment of the invention is illustrated in detail in the examples which follow the description of embodiment (4).

2) Monoclonal Antibodies Derived from the Same Host Species as the Antibodies Being Measured:

In this embodiment of the invention, the monoclonal antibodies may be derived from any vertebrate, mammalian species or otherwise that makes antibodies such as: rodent (i.e., mouse, hamster, rat), chicken, rabbit, canine, feline, bovine, equine, porcine, ape, and human. The host species chosen is in accordance with the intended purpose of the assay or kit.

For example, if human antibodies are being measured, the monoclonal antibodies may be established from human B cells by traditional hybridoma technology as mouse:human heterohybridomas, human:human hybridomas, or by some other means of immortalization such as by Epstein-Barr Virus infection (Nowinski, R. et. al., Science 210:537–539 (1980); Olsson, L. and Kaplan, H. S., Proc. Natl. Acad. Sci. USA 77:5429–5431 (1988); Rosen, A. M. et. al., Nature 267:52–54 (1977)). The recent creation of transgenic mice carrying genomic clones of part of the human H and L chain immunoglobulin loci provides the pportunity to also establish mouse:mouse hybridomas secreting monoclonal uman antibodies of desired specificities (Lonberg, N. et. al., Nature 368:856–859 1994); Green, L. L. et. al., Nature Genetics 7:13–21 (1994)).

Human antibodies may also be created through the use of recombinant DNA technology. For example, the H and L chain V regions (comprising the part of the antibody molecule responsible for ligand binding activity) may be isolated from single human B cells, human B cells propagated in vitro, or human B cells propagated in SCID mice (Simonsson, A. C. et. al., Bio/Techniques 18(5):862–869 (1995); (Banchereau, J. et. al., Science 251:70–72 (1991); Amoroso, K. and Lipsky, P. E., J. Immunol. 145:3155–3161 (1990); Duchosal, M. A. et. al., Nature 355:258–262 (1992)). Antibody V regions may be cloned by standard procedures known in the art, or modifications of these procedures. For instance, the V regions may be cloned according to the process described in Example III below.

Alternatively, human H and L chain V region sets with desired binding activity may be screened for as, for example, Fab fragments, Fv fragments, or single-chain Fv, by expression in bacteria, e.g. *E. coli*, or selected through the use of combinatorial libraries expressed in lambda phage, on the surface of bacteriophage, on the surface of bacteria, or screened by display on any other biological (e.g. retrovirus or polysome) or non-biological system (Better, M. et. al., Science, 240:1041–1043 (1988); Skerra, A. and Pluckthun, A., Science, 240:1038–1041 (1988); Huse, W. D. et. al., Science 246:1275–1281 (1989); McCafferty, J. et. al., Nature 348:552–554 (1990); Kang, A. S. et. al., Proc. Natl. Acad. Sci. USA 88: 4363–4366 (1991); Fuchs P. et. al., Bio/Technology 9:1369–1372 (1991); Francisco, J. et. al., Proc. Natl. Acad. Sci. USA 90:10444–10448 (1993); Mattheakis, L. C. et. al., Proc. Natl. Acad. Sci. USA 91:9022–9026 (1994)). The antibody libraries may consist of: native V regions from an immunized or unimmunized human, synthetic or semi-synthetic V regions, or modified V regions (Marks, J. D. et. al., J. Mol. Biol. 222:581–597 (1991); Barbas, C. F. III et. al., Proc. Natl. Acad. Sci. USA 89:4457–4461 (1992)). Examples of the latter include fine-tuning of specificity and/or affinity by in vitro mutagenesis. The primary basis for selecting the V regions is on the basis of their ligand-binding characteristics.

If human antibodies are being measured, the human H and L chain V region genes are cloned into a mammalian expression vector containing human H and L chain constant region genes. Introduction of the expression construct(s) into suitable host cells results in production of complete human antibodies of a defined specificity (Dorai, H. et. al., Hybridoma 11(5):667–675 (1992)). Many eukaryotic expression vectors for antibody have been described that are either stably integrated or exist as extrachromosomal elements, and these are known to those of ordinary skill in the art. The H and L chain transcription units can be introduced into the host cell individually on separate plasmids or together on the same vector.

One example of a suitable expression vector is the plasmid, pdHL2 (FIG. 3), that contains human IgG1 (hu Cγ1) and human kappa constant region (hu Cκ) genes in their genomic configuration (Gillies, S. D. et al., J. Immunol. Methods 125:191–202 (1989)). Both transcription units contain an upstream immunoglobulin H chain enhancer element (EH) and mouse metallothionein I promoter. Insertion of Vκ region and $V_H$ region cassettes results in expression of complete antibody. Each V gene cassette includes a 5' immunoglobulin leader sequence and a splice donor site 3' of the V gene. The vector also contains a bacterial origin of replication and β-lactamase gene derived from the plasmid pBR322 and an altered mouse dihydrofolate reductase (DHFR) gene under the control of the SV40 early region enhancer, promoter and polyadenylation signal sequences. The DHFR marker gene allows for selection and amplification in mammalian cells with methotrexate.

Antibody expression vectors may be modified to contain any of the constant region genes (in the case of humans: κ, λ, IgM, IgD, IgG1, IgG2, IgG3, IgG4, IgA1, IgA2, IgE) isolated from any vertebrate species that makes antibodies, including but not limited to: rodent (e.g., mouse, hamster, rat), chicken, rabbit, canine, feline, bovine, equine, porcine, ape (e.g. chimpanzee), and human. Similarly, antibody H and L chain V regions can be isolated from any vertebrate species that makes antibodies, including but not limited to: rodent (e.g., mouse, hamster, rat), chicken, rabbit, canine, feline, bovine, equine, porcine, ape (e.g. chimpanzee), and human. Introduction of H and L chain V regions into an antibody expression vector containing H and L chain constant regions derived from the same host species, results in formation of recombinant monoclonal antibody. Thus, monoclonal antibodies of any class or subclass can be produced from any vertebrate species that makes antibodies through the use of recombinant DNA, hybridoma, or a combination of these technologies. The host species chosen is in accordance with the intended purpose of the assay.

Depending on the expression vector(s), many different immortalized cell lines may serve as suitable hosts, these include but are not limited to: myeloma (e.g. X63-Ag8.653), hybridoma (Sp2/0-Ag14), lymphoma and Chinese Hamster Ovary (CHO) cells. Expression constructs can be introduced using a variety of techniques, including but not limited to, calcium phosphate precipitation, protoplast fusion, lipofection, retrovirus-derived shuttle vectors, and electroporation. Proper expression leads to secretion of the recombinant antibody into the medium. Alternatively, cells may be lysed and antibody subsequently purified.

Antibody molecules or fragments thereof could also be produced in other systems, including but not limited to: baculovirus, yeast, bacteria such as E. coli, and in vitro in cell-free systems such as rabbit reticulocyte lysate (Hasemann, C. and Capra, J. D. Proc. Natl. Acad. Sci. USA 87:3942–3946 (1990); Horwitz, A. H. et. al., Proc. Natl. Acad. Sci. USA 85:8678–8682 (1988); Pluckthun, A. Bio/Technology 9:545–551 (1991); Nicholls et. al., J. Biol. Chem. 268(7):5302–5308 (1993)).

Monoclonal antibodies produced by hybridoma, recombinant DNA, or a combination of these technologies may contain at least two (e.g. IgG) and up to 10 (e.g. pentameric IgM) identical binding sites with specificity and affinity to the desired ligand determined by the H and L chain V regions. The complete antibodies contain the entire H and L chain constant regions and thus all of the associated antigenic epitopes. Moreover, the antibodies are monoclonal thus are of a single-defined specificity and affinity and can be produced in unlimited quantities. One or more of these reagents may be used as calibrators and/or controls in diagnostic assays and kits designed to qualitatively or quantitatively measure levels of specific antibody.

3) A Monoclonal Antibody Derived from a Species Related, On the Basis of Immunologic Cross-Reactivity, to that being Assayed:

An additional embodiment of the invention includes a monoclonal antibody derived from a closely related species to that being assayed. Species relatedness is defined on the basis of immunological cross-reactivity of constant region epitopes. 20 At least one constant region epitope is the same or substantially the same to that of the species being assayed. The shared epitope(s) may not be chemically identical, but exhibit a chemical resemblance in 3-dimensional structure. The monoclonal antibodies may be derived from any vertebrate, mammalian species or otherwise that makes antibodies such as: rodent (i.e., mouse, hamster, rat), chicken, rabbit, 25 canine, feline, bovine, equine, porcine, ape, and human. The host species chosen is in accordance with the intended purpose of the assay and on the basis of reactivity with the reagent that binds specifically to one or more constant region epitopes of the species of antibody to be assayed.

For example, if one is measuring human antibody, a monoclonal antibody generated from another primate such as the chimpanzee may suffice as a calibrator or control. The differences at a molecular level between antibody constant region sequences of chimpanzee and human are roughly equivalent to those between allotypes of human (Ehrlich, P. H. et. al., Hum. Antibod. Hybridomas 1:23–26 (1990); Ehrlich, P. H. et. al., Mol. Immunol. 28:319–322 (1991)). Monoclonal antibodies may be derived from chimpanzee through the use of hybridoma or recombinant DNA technology. In the latter case, H and L chain V regions (comprising the part of the antibody molecule responsible for ligand binding activity) may be isolated from single chimpanzee B cells, chimpanzee B cells propagated in vitro, or in vivo (e.g. in SCID mice). Antibody V regions may be cloned by standard procedures known in the art, or modifications of these procedures. For instance, the V regions may be cloned according to the process described in Example III below.

Alternatively, chimpanzee H and L chain V region sets with desired binding activity may be screened for as, for example, Fab fragments, Fv fragments, or single-chain Fv, by expression in bacteria, e.g. E. coli, or selected through the use of combinatorial libraries expressed in lambda phage, on the surface of bacteriophage, on the surface of bacteria, or screened by display on any other biological (e.g. retrovirus or polysome) or non-biological system (Better, M. et. al., Science, 240:1041–1043 (1988); Skerra, A. and Pluckthun, A., Science, 240:1038–1041 (1988); Huse, W. D. et. al., Science 246:1275–1281 (1989); McCafferty, J. et. al., Nature 348:552–554 (1990); Kang, A. S. et. al., Proc. Natl. Acad. Sci. USA 88: 4363–4366 (1991); Fuchs P. et. al., Bio/Technology 9:1369–1372 (1991); Francisco, J. et. al., Proc. Natl. Acad. Sci. USA 90:10444–10448 (1993); Mattheakis, L. C. et. al., Proc. Natl. Acad. Sci. USA 91:9022–9026 (1994)). The antibody libraries may be composed of: native V regions from an immunized or unimmunized chimpanzee, synthetic or semi-synthetic V regions, or modified chimpanzee V regions. Examples of the latter include fine-tuning of specificity and/or affinity by in vitro mutagenesis. The primary basis for selecting the V regions is on the basis of their ligand-binding characteristics.

Chimpanzee H and L chain V region genes may be cloned into a mammalian expression vector containing chimpanzee constant region genes. Introduction of the expression construct(s) into suitable host cells results in production of complete chimpanzee antibodies of a defined specificity.

Many eukaryotic expression vectors for antibody have been described that are either stably integrated or exist as extra-chromosomal elements, and these are known to those of ordinary skill in the art. The H and L chain transcription units can be introduced into the host cell individually on separate plasmids or together on the same vector.

Figure 3:
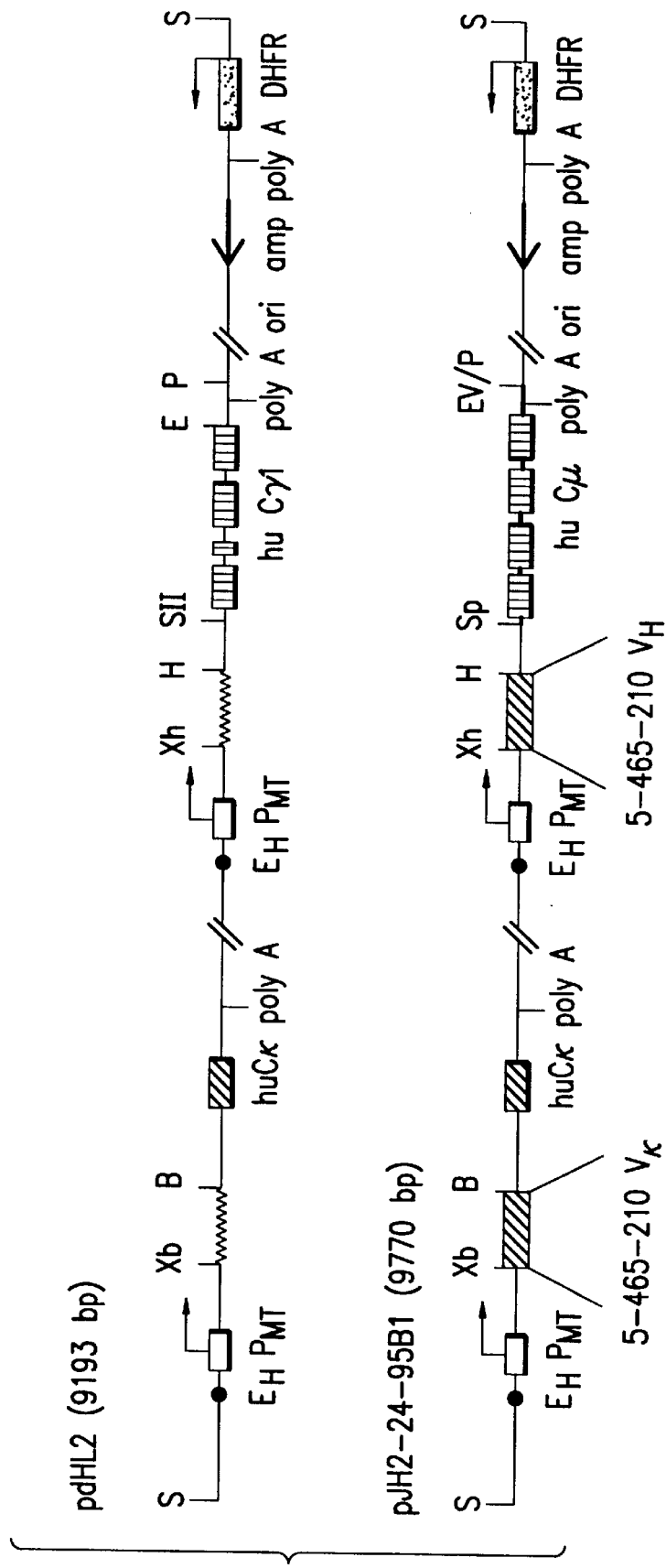
FIG. 3 represents the antibody expression vector pdHL2 which contains human IgGI (hu Cγ1) and human kappa constant region genes (hu Cκ) in their genomic configuration. Both transcription units contain an upstream immunoglobulin H chain enhancer element ($E_H$) and mouse metallothionein I promoter ($P_{MT}$). Insertion of Vκ region (Xba I-Bam HI) and VH region (Xho I-Hind III) cassettes results in expression of complete antibody. The vector also contains a bacterial origin of replication (ori) and β-lactamase (amp) gene derived from the plasmid pBR322 and an altered mouse dihydrofolate reductase (DHFR) gene under the control of the SV40 early region enhancer, promoter and polyadenylation (poly A) signal sequences. The DHFR marker gene allows for selection and amplification in mammalian cells with methotrexate. The chimeric IgM construct pJH2-24-95B1 is a modified version of pdHL2. In pJH2-24-95B1, the stuffer fragment located between the Xba I and Bam HI sites has been replaced by the 5-465-210 Vκ cassette (FIG. 7). The 5-465-210 $V_H$ cassette (FIG. 6) has been substituted for the stuffer fragment located between the Xho I and Hind III sites. In addition, the human IgGI has been replaced by a genomic clone of the human IgM constant region (hu $C_\mu$) gene. The hu $C_\mu$ clone extends from Spe I to the Eco RV/Pvu II junction. Restriction site abbreviations are: B, Bam HI; H, E, Eag I; EV, Eco RV; Hind HI; P, Pvu II; SII, Sac III; S, Sal I; Sp, Spe I; Xb, Xba I; and Xh, Xho I.

One example of an expression vector that may be modified to express chimpanzee antibodies is the plasmid, pdHL2 (FIG. 3). This vector contains human IgG1 (hu Cγ1) and human kappa constant region (hu Cκ) genes in their genomic configuration (Gillies, S. D. et al., J. Immunol. Methods 125:191–202 (1989)). Both transcription units contain an upstream immunoglobulin H chain enhancer element ($E_H$) and mouse metallothionein I promoter. Insertion of Vκ region and $V_H$ region cassettes results in expression of complete antibody. Each V gene cassette includes a 5' immunoglobulin leader sequence and a splice donor site 3' of the V gene. The vector also contains a bacterial origin of replication and β-lactamase gene derived from the plasmid pBR322 and an altered mouse dihydrofolate reductase (DHFR) gene under the control of the SV40 early region enhancer, promoter and polyadenylation signal sequences. The DHFR marker gene allows for selection and amplification in mammalian cells with methotrexate.

Antibody expression vectors may be modified to contain any of the constant region genes (in the case of humans: κ, λ, IgM, IgD, IgG1, IgG2, IgG3, IgG4, IgA1, IgA2, IgE) isolated from any vertebrate species that makes antibodies, including but not limited to: rodent (e.g., mouse, hamster, rat), chicken, rabbit, canine, feline, bovine, equine, porcine, ape (e.g. chimpanzee), and human. Similarly, antibody H and L chain V regions may be isolated from any vertebrate species that makes antibodies, including but not limited to: rodent (e.g., mouse, hamster, rat), chicken, rabbit, canine, feline, bovine, equine, porcine, ape (e.g. chimpanzee), and human. Introduction of H and L chain V regions into an antibody expression vector containing H and L chain constant regions derived from the same host species, results in formation of recombinant monoclonal antibody. Thus, monoclonal antibodies of any class or subclass can be produced from any vertebrate species that makes antibodies through the use of recombinant DNA, hybridoma, or a combination of these technologies. The host species chosen is in accordance with the intended purpose of the assay.

Depending on the vector system, many different immortalized cell lines may serve as suitable hosts. These include but are not limited: myeloma (e.g. X63-Ag8.653), hybridoma (Sp2/0-Ag14), lymphoma and Chinese Hamster Ovary (CHO) cells. Expression constructs can be introduced using a variety of techniques, including but not limited to, calcium phosphate precipitation, protoplast fusion, lipofection, retrovirus-derived shuttle vectors, and electroporation. Proper expression leads to secretion of the recombinant chimpanzee antibody into the medium. Alternatively, cells may be lysed and antibody subsequently purified.

Antibody molecules or fragments thereof could also be produced in other systems, including but not limited to: baculovirus, yeast, bacteria such as E. coli, and in vitro in cell-free systems such as rabbit reticulocyte lysate ((Hasemann, C. and Capra, J. D., Proc. Natl. Acad. Sci. USA 87:3942–3946 (1990); Horwitz, A. H. et. al., Proc. Natl. Acad. Sci. USA 85:8678–8682 (1988); Pluckthun, A. Bio/Technology 9:545–551 (1991); Nicholls et. al., J. Biol. Chem. 268(7):5302–5308 (1993)).

Monoclonal antibodies produced by hybridoma, recombinant DNA, or a combination of these technologies may contain at least two (e.g. IgG) and up to 10 (pentameric IgM) identical binding sites with specificity and affinity to the desired ligand determined by the H and L chain V regions. The complete antibodies contain the entire H and L chain constant regions and thus all of the associated antigenic epitopes. Moreover, the antibodies are monoclonal and thus are of a single-defined specificity and affinity and can be produced in unlimited quantities. One or more of these reagents may be used as calibrators and/or controls in diagnostic assays and kits designed to qualitatively or quantitatively measure levels of specific antibody.

4) A Polypeptide which Binds to a Predetermined Ligand Fused to an Antibody Constant Region of the Desired Host Species:

A fourth embodiment of the invention relates to a polypeptide capable of specifically binding to a predetermined ligand fused to an antibody constant region or some part of an antibody constant region (one or more constant region domains or one or more individual epitopes derived from the antibody constant region) of the desired host species. This includes any of the following fused to all or part of an antibody constant region of any desired species: (1) short polypeptides, such as one derived from a CDR of an antibody molecule, or those selected on the basis of ligand specificity through the use of, for example, phage display technology; (2) an antibody domain or derivative thereof such as a minibody; (3) Fv fragments; and (4) single-chain Fv fragments (Levi, M. et. al., Proc. Natl. Acad. Sci. USA 90:4374–4378 (1993); Smith, G. P. Science 228:1315–1317 (1985); Martin, F. et. al., EMBO J. 13(22):5303–5309 (1994)). This molecule may consist of one or more polypeptide chains. This embodiment may readily be produced using a wide variety of bacterial vectors well known to the art. Antibody fragments and derivatives thereof may also be produced in other host systems not limited to but including eukaryotic cells (Shu, L. et. al., Proc. Natl. Acad. Sci. USA 90:7995–7999 (1993)).

Reagents derived from this embodiment contain a polypeptide that binds to the chosen ligand with the desired specificity and affinity. This polypeptide is fused to an entire antibody constant region, one or more domains of the constant region, or one or more epitopes of the chosen constant region. The choice of antibody constant region or fragment thereof is dictated by the intended use. These reagents, whether produced in eukaryotic or prokaryotic expression systems, provide a continuous source of a reagent that binds to a predetermined ligand, is "monoclonal" in nature as it is uniform in specificity and affinity, and it contains at least one constant region epitope. One or more of these reagents may be used as calibrators and/or controls in diagnostic assays and kits designed to qualitatively or quantitatively measure levels of specific antibody.

Any of the reagents described in embodiments 1–4, may be used individually, or alternatively, more than one of these reagents may be used to produce calibrators (standard) and/or controls for an immunoassay. It is envisioned that a calibrator and/or control may be composed of a mixture of two or more reagents: (a) recognizing different epitopes on a given antigen, (b) one or more different epitopes on more than one antigen (e.g. P30 and P66 proteins of T. gondii), or one or more epitopes on antigens derived from more than one source (e.g. gp41 antigen of HIV-1 and gp36 antigen from HIV-2, to monitor for antibodies to both HIV-1 and HIV-2 in the same assay). The decision as to how many of these reagents to use to produce a calibrator (standard) and/or control is dependent upon the assay format and desired performance characteristics (e.g. specificity, sensitivity, precision, parallelism), is based on empirical observations and can be determined by methods known to the art.

Use of any of the aforementioned reagents as an alternative to sourcing high titer positive human plasma or serum for production of calibrators (standards) and/or controls in diagnostic assays and kits yields several important advantages:

(1) availability: These reagents can be produced easily and reproducibly in large quantities. The production scale can be readily tailored to demand, providing a renewable in-house supply.

(2) homogeneity: All of these reagents are "monoclonal" in nature in that they are uniform in specificity and affinity. This dramatically reduces lot-to-lot variation. This is in contrast to human plasma pools which vary in antibody concentration, titer of specific antibody, and specificity thereby affecting the immunoassay's performance.

(3) control of epitope specificity: One can readily dictate the specificity and affinity of the reagent. This provides a greater level of control over performance and manufacturability of the immunoassay.

(4) allowance for more complete characterization of the calibrators and controls, thus ensuring reagent quality, and also providing reagents potentially useful for monitoring the coating of antigen on the solid phase, thus reducing lot-to-lot variation in antigen concentration. For some assays, more than one protein antigen is coated on the solid phase. If, for example, the proteins are coated on microparticles, if one was monitoring coating with a polyclonal, it would be necessary to coat them individually and subsequently blend the microparticles. In contrast, with these reagents, beads could be co-coated with all the proteins and the density of each could be determined. These reagents also provide a tool to evaluate the stability and/or lot-to-lot consistency of specific epitopes on the antigen.

(5) reduced production costs: Unlimited availability coupled with the homogeneous nature of the reagent aids in optimization of purification methodology, both helping to reduce manufacturing, testing and regulatory-related costs, and (6) safety: Use of biological fluids (e.g. plasma, serum) to manufacture calibrators and controls is potentially biohazardous. Substituting these reagents for biological fluids in the manufacture calibrators and/or controls should significantly reduce the biohazard risk associated with these products.

In addition to use in assays and kits which detect or monitor antibodies to infectious agents (e.g., human immunodeficiency virus-1, human immunodeficiency virus-2, human T-cell leukemia virus-1, human T-cell leukemia virus-2, cytomegalovirus, hepatitis A virus, hepatitis B virus, hepatitis C virus, hepatitis D virus, hepatitis E virus, hepatitis GB virus, respiratory syncytial virus, Rubella virus, *Toxoplasma gondii, Trypanosoma cruzi, Cryptococcus neoformans, Histoplasma capsulatum, Helicobacter pylori,* and *Streptococcus pyogenes*), the reagents described in the present invention may also be used to monitor antibody responses to any other antigen. In particular, the reagents may be used in kits and assays which monitor antibodies to autoantigens, allergens, pharmaceuticals, and other environmental antigens. These assays may be designed to monitor/measure all reactive antibody, or alternatively, specific classes or subclasses of reactive antibody. The described agents are useful as calibrators and/or controls for monitoring antibody responses in man as well as any other vertebrate species capable of generating an antibody response and thus have human medical as well as veterinary applications.

The present invention may be illustrated by the use of the following non-limiting examples:

EXAMPLE I

Preparation of Cell Lines

The hybridomas 1-706-139 (IgG2b/K) and 5-465-210 (IgG2a/ic), specific for Toxoplasma proteins P66 and P30, respectively, were established by fusion of immunized Swiss Webster spleen cells to the non-secreting hybridoma Sp2/0-Ag14 at Abbott Laboratories (Abbott Park, Ill.). Hybridomas were passaged in IMDM (550 mg glucose/L) supplemented with 10% fetal bovine serum (FBS), 8 mM L-glutamine, 100 U penicillin/ml and 100 µg/ml streptomycin (complete IMDM). Sp2/0 Ag14 cells (Abbott Laboratories; American Type Culture Collection, Rockville, Md.) used for electroporation were passaged in high glucose D-MEM containing L-glutamine supplemented with 10% FBS, 1 mM sodium pyruvate, 10 mM HEPES and 10 µg/ml gentamicin (complete D-MEM). Sp2/0 Ag14 cells (Abbott Laboratories) used for transfection by protoplast fusion were passaged in D-MEM (Catalog #11995) supplemented with 20% FBS, 0.8 µg/ml 8-azaguanine (Sigma Chemical Company, St. Louis, Mo.), 50 U/ml penicillin and 50 µg/ml streptomycin.

Transfectants secreting chimeric antibody were passaged in complete IMDM supplemented with 0.1 µM methotrexate (MTX) purchased from Sigma, Adria Laboratories (Columbus, Ohio) or Lederele Laboratories (Carolina, Puerto Rico). Unless specified, all tissue culture media and supplements were purchased from BRL Life Technologies (Gaithersburg, MD). Cells were cultured at 37° C. in 5% $CO_2$.

EXAMPLE II

Cloning

Primers for cloning and sequencing were purchased from Operon Technologies, Inc (Alameda, Calif.) unless otherwise specified. Primers used for isolation of immunoglobulin variable (V) regions and for transfer of fragments were HPLC purified. Reagents from Perkin-Elmer GeneAmp Kits (Perkin-Elmer Corporation, Foster City, Calif.), including AmpliTaq DNA polymerase, were used according to the manufacturer's specifications for polymerase chain reaction (PCR) amplifications. Reverse transcription and PCR reactions were performed on a GeneAmp 9600 thermal cycler (Perkin-Elmer). Restriction enzymes were purchased from BRL Life Technologies or New England BioLabs (Beverly, Mass.) and digests were performed as recommended by the manufacturer. Unless indicated otherwise, DNA fragments used for cloning were isolated on low-melting point (LMP) agarose (FMC Corporation, Rockland, Me.). Briefly, desired fragments were excised from the gel, diced into small pieces and added to 400 µl TE [1 mM ethylenediaminetetraacetic acid (EDTA; pH 8.0; BRL Life Technologies), 10 mM tris(hydroxymethyl)aminomethane-hydrochloride (Tris-HCl: pH 8.0; BRL Life Technologies)] in an eppendorf microfuge tube. The agarose was melted at 68° C. and extracted with 800 µl of buffer-saturated phenol (BRL Life Technologies) by vortexing for one minute and centrifugation at 14,000×g in a microcentrifuge. The aqueous phase was transferred to a new tube and one tenth volume of 10M $LiCl_2$ (Sigma Chemical Co., St. Louis, Mo.) was added. The tube was centrifuged as above for 5 minutes. The aqueous phase was transferred to a new tube and precipitated with 2.5 volumes absolute ethanol (−20° C., McCormick Distilling Co., Weston, Mo.). The DNA was pelleted as above for 15 minutes and washed 2× with 70% ethanol (−20° C.). DNA was resuspended in H$_2$O or TE. Ligations were performed using a Stratagene DNA ligation kit (Stratagene Cloning Systems, La Jolla, Calif.) as recommended by the manufacturer. With the exception of protoplast fusion studies, bacterial transformations were performed using MAX EFFICIENCY DH5α (BRL Life Technologies) competent cells following the manufacturer's protocol. Screening of transformants to identify desired clones was accomplished by restriction digest analysis of miniprep DNA and/or by colony PCR. Miniprep DNA was prepared with the Magic Miniprep Purification System (Promega Corporation, Madison, Wis.) or with the EasyPrep Plasmid Prep Kit (Pharmacia Biotech, Inc., Piscataway, N.J.) following the manufacturer's specifications. For colony PCR screening, individual colonies were picked from transformation plates and transferred into a well in a sterile flat-bottom 96-well plate (Costar, Cambridge, Mass.) containing 100 µl sterile H$_2$O. One-third of the volume was transferred to a second plate and stored at 4° C. The original 96-well plate was microwaved for 5 minutes to disrupt the cells. One µl volume was then transferred to a PCR tube as template. Nine µl of a PCR master mix containing 1 µl 10X PCR buffer, 1 µl 2 mM dNTPs, 1 µl (10 pmol) sense primer, 1 µl (10 pmol) anti-sense primer, 0.08 µl AmpliTaq DNA polymerase (0.4 units), and 4.2 µl H$_2$O was added to the PCR tube. All PCR reagents were purchased from Perkin-Elmer Corporation. Reactions were generally amplified for 20–25 cycles of 94° C. for 30 seconds, 50–60° C. (depending on primer annealing temperatures) for 30 seconds and 72° C. for 60 seconds. Primers were dependent on the insert and cycle conditions were modified based on primer annealing temperatures and the length of the expected product. After cycling, approximately ⅓ of the reaction volume was loaded on an agarose gel for analysis. Colonies containing desired clones were propagated from the transfer plate.

were performed with a Perkin Elmer GeneAmp RNA PCR Kit. For specific cDNA synthesis of heavy (H) chain V regions, 90 ng of purified hybridoma mRNA and 10 pmol of the primer M-IgG2b (Table 1) or M-IgG2a, both containing a Bgl II site were used for 1-706-139 and 5-465-210, respectively. Specific cDNA priming of both kappa (K) light chain variable (V) regions was carried out with the primer MK-REV containing a Bgl II site. Reverse transcription reactions were incubated at 42° C. for 60 minutes then at 99° C. for 5 minutes. PCR reactions (100 volume; 50 pmol of each primer) were set up according to the manufacturer's specifications. For 1-706-139 VH region amplification, sense primer MHV-9 and the primer M-IgG2b were used. The 1-706-139 VK region was amplified with MKV-1 (sense) and MK-REV primers. For 5-465-210 VH region amplification, primers MHV-7 (sense) and M-IgG2a were used. Amplification of the 5-465-210 VK region was performed with MKV-2 (sense) and MK-REV primers. All sense primers contained a Sal I site. Amplifications consisted of 30 cycles of 94° C. for 30 seconds, 52° C. for 30 seconds and 72° C. for 60 seconds. PCR-derived products were isolated by the Promega Magic PCR Preps DNA Purification System (Madison, Wis.). V$_H$ and VK fragments were digested with Sal I and Bgl II and ligated into Sal I and Bam HI digested pUC 18 (BRL Life Technologies). Plasmids pJH6-20-94A1 and pJH6-14-94A5 contain V$_H$ and VK regions, respectively, cloned from hybridoma 1-706-139. Plasmids pJH6-30-94A1 and pJH7-31-94D3 contain V$_H$ and VK regions, respectively, isolated from hybridoma 5-465-210.

TABLE 1

Primers used for isolation of hybridoma V regions

| | | |
|---|---|---|
| M-IgG2b | 5'-d[ATTCGGATAGATCTAGTGGATAGACTGATGG]3' | (SEQ ID NO:9) |
| M-IgG2a | 5'd[ATTCGGATAGATCTAGTGGATAGACCGATGG]3' | (SEQ ID NO:10) |
| MK-REV | 5'd[ATTCGGATAGATCTTGGATGGTGGGAAGATG]3' | (SEQ ID NO:11) |
| MHV-9 | 5'd[ACACTAGTCGACATGGMTTGGGTGTGGAMCTTGCTATTCCTG]3' | (SEQ ID NO:12) |
| MKV-1 | 5'd[ACACTAGTCGACATGAAGTTGCCTGTTAGGCTGTTGGTGCTG]3' | (SEQ ID NO:13) |
| MHV-7 | 5'd[ACACTAGTCGACATGGRATGGAGCKGGRTCTTTMTCTT]3' | (SEQ ID NO:14) |
| MKV-2 | 5'd[ACACTAGTCGACATGGAGWCAGACACACTCCTGYTATGGGT]3' | (SEQ ID NO:15) |

EXAMPLE III

Isolation of Variable Regions from Hybridomas, Construction of Expression Vectors and Transfer of Variable Regions into Expression Vectors i) Isolation of Immunoglobulin Variable Regions:

A Pharmacia QuickPrep mRNA Purification Kit was used according to the manufacturer's specifications to isolate mRNA from 1×10$^7$ hybridoma cells. First-strand complementary DNA (cDNA) synthesis and PCR amplification ii) Human IgM Expression Vector Construction:

The immunoglobulin expression vector pdHL2 (FIG. 3; Gillies, S. D. et. al., (1989) J. Immunol. Methods 125:191–202) was modified for expression of human IgM (FIG. 4) by replacing the human IgG1 constant region (C$_{\gamma 1}$) with a genomic clone of the human IgM constant region (Cμ). The first step was to introduce a Spe I restriction site into the Sac II site 31 bp upstream of the first exon of C$_{\gamma 1}$. The coding strand oligonucleotide Spe-1, 5'd [GGAACTAGTGGAGC]3' (SEQ ID NO:18), was annealed to the oligonucleotide Spe-2, 5'd[TCCACTAGTTCCGC]3' (leaving Sac II overhangs) (SEQ ID NO:19), and ligated into Sac II digested pdHL2, yielding the vector pAG/SpeI.

The Cγ1 gene in pAG/SpeI is flanked by Spe I and Eag I (located 7 bp downstream of the termination codon) sites and was removed by a double digestion with these enzymes. A fragment containing a genomic clone of the secretory portion of C$_μ$ was generated by PCR amplification using 1 ng of the vector H+L cassette #1 (8/89) Hyland (Abbott Biotech) as template and 50 pmol of the primers 5'huM-B (Table 2), containing a Spe I site and 3'-huMEag, containing an Eag I site. Amplification consisted of 24 cycles of 94° C. for 30 seconds, 63° C. for 30 seconds, and 72° C. for 90 seconds. The 1880 bp IgM $C_\mu$ product (position 219 through 2099 in Dorai, H. and Gillies, S. D., Nucleic Acids Research 17:6412 (1989)) was gel-isolated, double digested with Spe I and Eag I, and cloned into pAG/SpeI (replacing the IgGl gene) to generate pAG/SpeI/huM.

Plasmids pAG/huM/αtoxo and pAG/huM/αtoxo 5–465 were constructed by transfer of the 1-706-139 and 5-465-210 V region sets, respectively, into pAG/SpeI/huM (see section below). Preliminary studies with these constructs revealed low levels of recombinant IgM expression so the constructs were further modified. A genomic clone of the secretory portion of the $C_\mu$ gene that contains native IgM poly A signal sequences was PCR amplified, under the conditions outlined above, using 1 ng of plasmid pN·χ-μTNP DNA (obtained from Dr. Marc Shulman, University of Toronto, Toronto, Ontario; Boulianne, G. L., et. al., Nature 312:643–646 (1984)) as template and 50 pmol each of the primers 5'huM-B and 3'amp-hoM (containing an EcoR V site). Gel-isolated Cμ (position 128 through 2278 in Word, C. J., et. al., International Immunology 1:296–309 (1989)) PCR product was ligated into the vector, pGEM-T (Promega Corporation, Madison, WI), following the manufacturer's recommended conditions. A clone containing the $C_\mu$ insert was identified and designated pGEM/IgM. The entire IgM insert was sequenced to verify its integrity.

Plasmid pGEM/IgM was modified by extending the native 5' intron sequences upstream of Cμ exon 1. The intron fragment (5' end at position 17 in Word, C. J. et. al., International Immunology 1:296-309 (1989)) was PCR amplified using 1 ng pN·χ-μTNP plasmid DNA as template and 50 pmol each of the primers 5-SPL/Spe containing a Spe I site and 3-SPL (both synthesized at Abbott). After 24 cycles of 94° C. for 30 seconds, 60° C. for 30 seconds and 72° C. for 45 seconds, the intron fragment was phenol/chloroform extracted and precipitated. Both intron product and pGEM/IgM vector were digested with Spe I and Bsu 36 I (New England Biolabs), gel isolated, and ligated to generate the human Cμ gene construct pJH2-14-95A3. The intron insert was characterized by sequencing.

Plasmid pAG/huM/αtoxo 5-465 was modified by replacing its $C_\mu$ gene segment with the human $C_\mu$ gene segment containing native 5' intron and poly A signal sequences, present in pJH2-14-95A3 (referred to as complete $C_\mu$). Plasmid pAG/huM/αtoxo 5–465 was double digested with Spe I and Pvu II (downstream of $C_{\gamma 1}$ poly A addition site; position 2137 in GenBank accession # Z17370) and the vector backbone was gel isolated. The complete $C_\mu$ gene was released from pJH2-14-95A3 by digestion with Spe I and Eco RV. Ligation of the gel isolated fragments resulted in the plasmid pJH2-24-95B 1 (FIG. 3). This expression vector contains murine $V_H$ and Vκ genes isolated from hybridoma, 5-465-210, and genomic clones of human $C_\mu$ and $C_κ$ genes.

Figure 5:
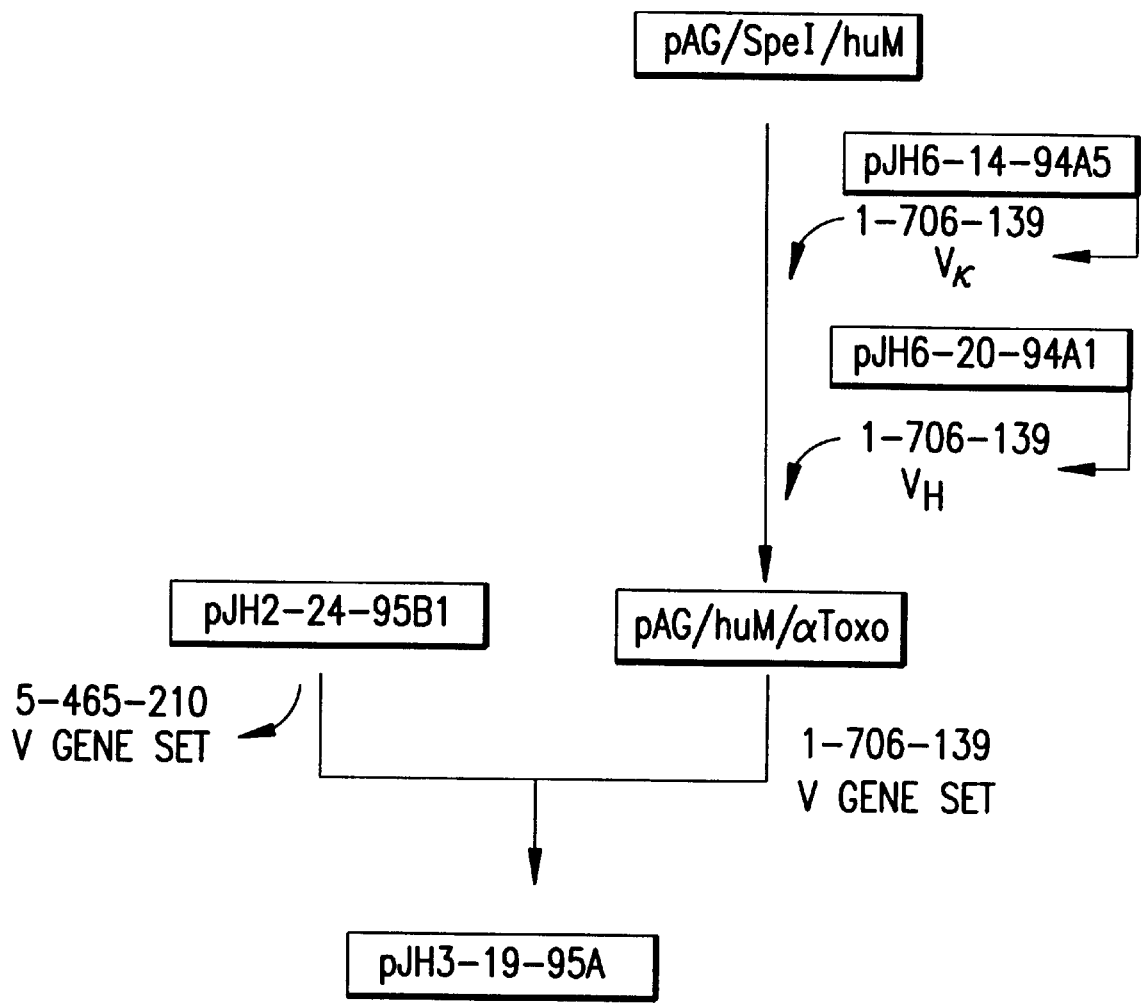
FIG. 5 represents a summary of the strategy used to construct the expression vector pJH3-19-95A. This expression construct encodes a mouse-human chimeric IgM antibody with H and L chain V regions derived from the mouse hybridoma 1-706-139 and human constant region genes. This chimeric IgM antibody binds selectively to P66 of T. gondii.

A second version of this expression vector, pJH3-19-95A, containing Vκ and $V_H$ genes cloned from hybridoma, 1-706-139, was constructed by replacing the Xba I-Hind III fragment in pJH2-24-95B 1 (containing Vκ 5-465-210, the kappa constant region and $V_H$ 5-465-210) with the analogous Xba I-Hind III fragment isolated from the plasmid pAG/huM/αtoxo (FIG. 5). The final IgM expression vectors pJH2-24-95B1 and pJH3-19-95A were both introduced into *E. coli* C60OR⁻ (American Type Culture Collection) in preparation for transfection by protoplast fusion.

iii) Transfer of Immunoglobulin V Regions into the IgM Expression Vector:

The Vκ and $V_H$ regions cloned from the hybridomas were introduced as cassettes into the immunoglobulin expression vector pAG/SpeI/huM containing transcription units for the human Cκ and human $C_\mu$. Proper expression of the Vκ and $V_H$ regions requires the addition of part of the 5' leader sequences and 3' splice donor junctions. These regions were incorporated into primers (Table 2) used for sequential PCR-mediated transfer of Vκ and $V_H$ regions into the expression vector. For transfer of the 1-706-139 VK gene, the 5' (leader) primer VK1-706-5', containing an Xba I site, and the 3' primer VK1-706-3' containing a splice junction and Bam HI site were used. For 1-706-139 $V_H$ region amplification, the 5' (leader) primer VH 1-706-5' containing a Xho I site and the 3' primer VH1-706-3' containing a Hind III site were used. For 5-465-210 Vκ gene transfer, the 5' (leader) primer VK5-465-5' containing an Xba I site and the 3' primer VK5-465-3' containing a Bam HI site were used. For 5-465-210 $V_H$ gene transfer, the 5' (leader) primer VH5-465-5' with a Xho I site and the 3' primer, VH5-465-3', containing a Hind III site were used. The 100 μl volume reactions included 50 pmol of each primer and 1 ng of plasmid template [pJH6-14-94A5 (1-706-139 Vκ); pJH6-20-94A1 (1-706-139 $V_H$); pJH7-31-94D3 (5-465-210 Vκ); or pJH6-30-94A1 (5-465-210 $V_H$). Amplification consisted of 22 cycles of 94° C. for 30 seconds, 62° C. for 30 seconds and 72° C. for 60 seconds. PCR-derived Vic products were digested with Xba I and Bam HI and cloned into vector (pAG/SpeI/huM) digested with Xba I and Bam HI. Subsequently, the $V_H$ product was introduced into the Vκ containing vector using Xho I and Hind III. The integrity of the Vκ and $V_H$ inserts was established by sequence analysis. The resulting expression vectors, pAG/huM/αtoxo and pAG/huM/toxo 5–465, contain he 1-706-139 and 5-465-210 V region sets (Vκ and $V_H$), respectively.

TABLE 2

| | Primers for construction of IgM expression vectors | |
|---|---|---|
| 5'huM-B | 5'd[TGACTGTAACTAGTCCTGCGGGTCCTCAGGGAGTGCATCCGCCCCAACCCTTTTCCCCCTC]3' | (SEQ ID NO:16) |
| 3'-huMEag | 5'd[TGATCTAGCGGCCGTCGCACTCAGTAGCAGGTGCCAGCTGTGTCGGAC]3' | (SEQ ID NO:56) |
| 3'amp-hoM | 5'd[CTGATCGAGATATCAAGCCACTGAGGCACGCAGGTGGGTG]3' | (SEQ ID NO:57) |
| 5-SPL/Spe | 5'd[TCAGGTGACTGAACTAGTCCTTGGTGGGGCAGCCACAGCG]3' | (SEQ ID NO:58) |
| 3-SPL | 5'd[CGACGGGGAATTCTCACAGGAGAC]3' | (SEQ ID NO:17) |
| VK1-706-5' | 5'd[TCACGAAGTCTAGACCTCAAATGAAGTTGCCTGTTAGGCTGTTGGTG]3' | (SEQ ID NO:59) |

TABLE 2-continued

Primers for construction of IgM expression vectors

| | | |
|---|---|---|
| VK1-706-3' | 5'd[GAATCTATGGATCCTGACACACTTACGTTTGATTTCCAGCTTGGTGCCTCC]3' | (SEQ ID NO:60) |
| VH1-706-5' | 5'd[ACACTATACTCGAGACATCATGGCTTGGGTGTGGACCTTGCTA]3' | (SEQ ID NO:61) |
| VH1-706-3' | 5'd[TTCAGATCAAGCTTGACACACTTACCTGAGGAGACGGTGACTGAGGTTCC]3' | (SEQ ID NO:62) |
| VK5-465-5' | 5'd[TCACGAAGTCTAGAGCTCTCAGAGATGGAGTCAGACACACTCCTGCTA]3' | (SEQ ID NO:63) |
| VK5-465-3' | 5'd[GAATCTATGGATCCTGACACACTTACGTTTTATTTCCAGCTTGGTCCCCG]3' | (SEQ ID NO:64) |
| VH5-465-5' | 5'd[ACACTATACTCGAGACTCCAACCATGGGATGGAGCTGGATCTTTCTC]3' | (SEQ ID NO:65) |
| VH5-465-3' | 5'd[TTCAGATCAAGCTTGACACACTTACCTGAGGAGACTGTGAGAGGGGTG]3' | (SEQ ID NO:66) | iv) Transfer of Murine V Region Sets into a Human IgG1 Expression Vector:

To generate a construct for expression of the functional Vκ and VH regions cloned from the hybridoma 1-706-139 as IgG1, the Xba I-Hind II fragment encompassing both of these regions was excised from pAG/huM/αtoxo and introduced into Xba I and Hind III digested pdHL2, yielding the expression construct designated pJH9-14-94/4.1. The same procedure was used to transfer the Vκ and $V_H$ gene set isolated from hybridoma 5465-210 from the plasmid pAG/huM/αtoxo 5-465 into pdHL2 to generate the expression construct, pdHL-2/5-465 (clone 1).

EXAMPLE IV

Sequencing of Variable Regions in Expression Vectors

Plasmid template for sequencing was prepared with Magic Miniprep or Maxiprep DNA Purification Systems (Promega), the EasyPrep Plasmid Prep Kit (Pharmacia), or by CsCl banding (Sambrook J. et. al., Molecular Cloning, 2nd edition, Cold Spring Harbor, N.Y., Cold Spring Harbor Press (1989)). The manufacturers recommended procedures were followed for preparation of plasmids with the kits. Nucleotide sequences were determined manually by Sequenase version 1.0 with a Sequenase 7-deaza-dGTP DNA Sequencing Kit (Amersham Life Science, Inc., Arlington Heights, Ill.) or by automated sequencing using the Pharmacia AutoRead Sequencing Kit and ALF DNA Sequencer. The vector primers (Table 3) ALF M13 Universal (Pharmacia) and ALF M13 Reverse (Pharmacia) were used for sequencing $V_H$ and Vκ inserts. Multiple clones of PCR-generated $V_H$ and Vκ regions were sequenced to monitor for AmpliTaq DNA polymerase-induced errors.

Primers used for sequencing of $V_H$ and Vκ fragments cloned into the mammalian expression vectors included the primers: pdHL2-4F, pdHL2-7F, pdHL2-43, pdHL2-44, pdHL2-52 and pdHL2-53. In addition, T1706H-A and T1706H-B, for 1-706-139 $V_H$; T1706K-A and T1706K-B for 1-706-139 Vκ; T5465H-A, T5465H-B, and T5465H-C for 5-465-210 $V_H$; and T5465K-A, T5465K-B, and T5465K-C for the Vκ region cloned from 5-465-210.

Primers used for sequencing of the human IgM genomic clone are listed in Table 4.

TABLE 3

Primers for sequencing variables region inserts in the expression vectors

| | | |
|---|---|---|
| ALF M13 Universal | 5'-fluorescein-d[GTAAAACGACGGCCAGT]3' | (SEQ ID NO:67) |
| ALF M13 Reverse | 5'-fluorescein-d[CAGGAAACAGCTATGAC]3' | (SEQ ID NO:68) |
| pdHL2-4F | 5'-fluorescein-d[ACGTCATCCGACCCCCTCAG]3' | (SEQ ID NO:20) |
| pdHL2-7F | 5'-fluorescein-d[CTGCCCCAAAGCCAAGGTCA]3' | (SEQ ID NO:21) |
| pdHL2-43 | 5'd[CTCCAGCTTCACCAGATCCCTCGAC]3' | (SEQ ID NO:22) |
| pdHL2-44 | 5'd[CTCCAGCTTCACCAGATCCCTCGAG]3' | (SEQ ID NO:23) |
| pdHL2-52 | 5'd[GCCACCTGCCTCACCTTAG]3' | (SEQ ID NO:24) |
| pdHL2-53 (Abbott Labs) | 5'd[AGAATGGCCACGTCATCCG]3' | (SEQ ID NO:25) |
| T1706H-A | 5'd[TCCAATGCACTGGGTGAAGC]3' | (SEQ ID NO:26) |
| T1706H-B | 5'd[GCAAACCGTCCCTTGAAGTC]3' | (SEQ ID NO:27) |
| T1706K-A | 5'd[ATTTACATTGGTATCTGCAG]3' | (SEQ ID NO:28) |
| T1706K-B | 5'd[CCAGAAAATCGGTTGGAAAC]3' | (SEQ ID NO:29) |
| T5465H-A | 5'd[CGAGACTCCAACCATGGGAT]3' | (SEQ ID NO:30) |

TABLE 3-continued

Primers for sequencing variables region inserts in the expression vectors

| | | |
|---|---|---|
| T5465H-B | 5'd[TGATAGAGTGGGTGACACAG]3' | (SEQ ID NO:31) |
| T5465H-C | 5'd[GCCCTGCCCTTGAATTTCTC]3' | (SEQ ID NO:32) |
| T5465K-A | 5'd[TAGAGCTCTCAGAGATGGAG]3' | (SEQ ID NO:33) |
| T5465K-B | 5'd[CTATGCTGCATCCAACCTAG]3' | (SEQ ID NO:34) |
| T5465K-C | 5'd[GATGAATGTTGAGGGTGAAG]3' | (SEQ ID NO:35) |

TABLE 4

Sequencing primers for genomic clone of the IgM constant region

| | | |
|---|---|---|
| HMC-1 | 5'd[ATACAAGAACAACTCTGACA]3' | (SEQ ID NO:36) |
| HMC-2 | 5'd[GTCTTCGTCCCACCCCGCG]3' | (SEQ ID NO:37) |
| HMC-3 | 5'd[CTCCATGTGTGTCCCCGGTG]3' | (SEQ ID NO:38) |
| HMC-4 | 5'd[ATCCTTTGCCAGCATCTTCC]3' | (SEQ ID NO:39) |
| HMC-5 | 5'd[ACTCTTGCCCcTCTTCCTGC]3' | (SEQ ID NO:40) |
| HMC-6 | 5'd[GACCAGCGCCCCAATGCCTG]3' | (SEQ ID NO:41) |
| HMC-7B | 5'd[TTTGCATGCACACACAGAGC]3' | (SEQ ID NO:42) |
| HMC-8 | 5'd[GCATCCACTGCACGAAGACG]3' | (SEQ ID NO:43) |
| HMC-9 | 5'd[AGGGCAGGTCTGTGTGGGTC]3' | (SEQ ID NO:44) |
| HMC-10 | 5'd[CATGGTTCCCACCCAAAGAG]3' | (SEQ ID NO:45) |
| HMC-11 | 5'd[ACTCTTTGGCCTCAGCCTGC]3' | (SEQ ID NO:46) |
| HMC-12 | 5'd[GCACACCACGTGTTCGTCTG]3' | (SEQ ID NO:47) |
| HMC-13 | 5'd[GTGCATGCAAACTAACCGTG]3' | (SEQ ID NO:48) |
| 45403 (igm1) (Abbott Laboratories) | 5'd[GCTCCTCCCATATGGTCGAC]3' | (SEQ ID NO:49) |
| 45404 (igm2) (Abbott Laboratories) | 5'd[CAGGCCCGATGTCTACTTGC]3' | (SEQ ID NO:50) |
| 45405 (igm3) (Abbott Laboratories) | 5'd[CTCATGGGCCACCACGCAGG]3' | (SEQ ID NO:51) |
| 45406 (igm4) (Abbott Laboratories) | 5'd[CTGCGAGGATGACTGGAATT]3' | (SEQ ID NO:52) |
| 45407 (igm5) (Abbott Laboratories) | 5'd[GCTGGTCACATACTTCTCCG]3' | (SEQ ID NO:53) |
| pdHL2-46 | 5'd[CGGGAGCTGCATGTGTCAG]3' | (SEQ ID NO:54) |
| pdHL2-54 Abbott Laboratories | 5'd[CAGACACTGGACGCTGAACC]3' | (SEQ ID NO:55) |
| Reverse M13 lac Z primer (Perkin-Elmer) | 5'd[GAGCGGATAACAATTTCACACAGG]3' | (SEQ ID NO:69) |
| -21 (M13) primer (Applied Biosystems, Inc) | 5'd[TGTAAAACGACGGCCAGT]3' | (SEQ ID NO:70) |

EXAMPLE V

TRANSFECTION OF EXPRESSION VECTORS INTO HOST CELLS

Plasmids used for electroporation were purified by CsCl banding (Sambrook J. et. al., Molecular Cloning, 2nd edition, Cold Spring Harbor, New York, Cold Spring Harbor Press (1989)). To transfect by electroporation, Sp2/0-Ag14 cells in log-phase growth were harvested and washed twice in 10 ml Dulbeccos phosphate buffered saline (D-PBS, BRL Life Technologies), and resuspended in D-PBS to a concentration of $1 \times 10^7$ cells/ml. Ten $\mu$g of Sal I linearized plasmid DNA was added to $1 \times 10^7$ Sp2/0-Ag14 cells in a 0.4 cm gap Bio-Rad (Melville, N.Y.) electroporation cuvette in a total of 1 ml D-PBS. DNA and cells were incubated on ice 10 minutes. The cuvette was placed into the chamber of a Bio Rad Gene Pulser set at 0.18 kv and 960 $\lambda$F capacitance. Current was applied and cuvette was mixed to eliminate the pH gradient. Cells were placed on ice for 5 minutes prior to plating. Cells were transferred to 19 ml compete D-MEM media and gently mixed. 100 µl of cell suspension was added to each well of two 96-well tissue culture clusters (flat-bottom; Costar) and incubated at 37° C0 in 5% $CO_2$. After 24 hours, 100 µl of complete D-MEM supplemented with 0.1 µM MTX (Sigma), was added to each well, and plates were incubated as above. After 48 hours, 100 µl media was removed from each well, and 100 µl of compete D-MEM with 0.1 µM MTX was added back. This process was repeated after 48 hours. Plates were subsequently incubated for 10 to 21 days until colonies began to appear. Supernatants were harvested from wells containing MTX-resistant colonies and assayed by ELISA (see below) for the presence of chimeric antibody.

A second method used to establish Sp2/0-Ag14 transfectants was a modified version of the protoplast fusion technique (Sandri-Golden, R. M. et. al., Molecular and Cellular Biology 1:743–752 (1981); Gillies, S. D. et. al., Cell 33:717–728 (1983)). Plasmids were propagated in *E. coli* $C600R^-$ to generate protoplasts. Bacteria were grown at 37° C. with vigorous aeration in 50 ml of medium containing 10 mg/ml M9 salts (BRL Life Technologies), 0.8% Casamino acids (Difco, Detroit, Mich.), 0.5% glucose (BRL Life Technologies), 0.1 mM $CaCl_2$ (Sigma), 1 mM $MgSO_4$ (Sigma), and 50 µg/ml ampicillin (Sigma) to an absorbance at 600 nm of 0.5–0.6. Chloramphenicol (Sigma) was added to 200 µg/ml, and the culture incubated as above for an additional 18–22 hours. Cells were pelleted at 1100×g for 12 minutes at 4° C. and resuspended in 2.5 ml of 20% sucrose (Sigma) in 0.05 M Tris-HCl, pH 8.0 (BRL Life Technologies) at 4° C. A solution of 5 mg/ml lysozyme (Pharmacia) in 0.25 M Tris-HCl (pH 8.0) was added and the mixture placed on ice. After a 5 minute incubation, 1.0 ml of 0.25 M EDTA (pH 8.0; BRL Life Technologies) was added and the mixture held on ice for an additional 5 minutes. One ml of 0.05 M Tris-HCl (pH 8.0) was then added slowly. The suspension was incubated at 37° C. for 10 minutes. Subsequently, 20 ml of D-MEM (Catalog #11995, BRL Life Technologies) supplemented with 10 mM $MgCl_2$ (Sigma) and 10% sucrose (Sigma) at room temperature was used to slowly dilute the protoplast solution. This mixture was held at room temperature for 2.5 hours. Approximately $5 \times 10^6$ Sp2/0 Ag14 cells harvested in log-phase growth were pelleted at 350×g for 5 minutes. Cells were gently resuspended in the protoplast suspension. This suspension was transferred to a 60 mm dish and centrifuged at 650×g for 8 minutes. The supernatant was aspirated and 1.5 ml of 50% w/v PEG (Sigma Hybri Max) in PBS prewarmed to 37° C. was added. The dish was centrifuged at 110×g until 90 seconds had elapsed from the point of PEG addition. Cells were gently resuspended by pipetting in two 5 ml and one 10 ml volumes of prewarmed wash solution (D-MEM supplemented with 1% FBS, 50 U/ml penicillin and 50 µg/ml streptomycin) which were added to a 50 ml centrifuge tube containing 15 ml of the wash solution. After centrifugation at 225×g for 7.5 minutes, cells were resuspended in plating medium (D-MEM supplemented with 10% FBS, 50 U/ml penicillin, 50 µg/ml streptomycin and 100 µg/ml kanamycin (Sigma) and plated in one 96-well dish and incubated at 37° C. After 24 hours (day 1), selective medium (D-MEM supplemented with 10% FBS and 0.1 µM MTX) was added. On day 5, 50 µl of the selective medium was added per well. After two days, 100 µl/well was removed and 100 µl of fresh selective medium added per well. MTX-resistant colonies were tested for secretion of chimeric antibody by ELISA assay.

EXAMPLE VI

Assays for the Determination of Chimeric Antibody Production by Transfectants Transfectants were assayed by ELISA for production of chimeric IgG1. EIA plates (96-well, Nunc Immulon, Naperville, Ill.) were coated with 100 µl mouse anti-human IgG (H+L chain; Jackson Immuno Research, West Grove, Pa.) at 1.5 µg/ml and incubated at 37° C. for 1 hour. Plates were washed 4 times in 1× Dulbecco's phosphate-buffered saline without Ca or Mg (D-PBS; BRL Life Technologies). Wells were blocked with 200 µl of 2.0% non-fat dry milk (Carnation Company, Los Angeles, Calif.) in 1× D-PBS for 1 hour at 37° C. Plates were washed as above. Purified human IgG (Jackson Immuno Research) or purified chimeric IgG1 antibody (Abbott Laboratories) diluted in 1× D-PBS with 2% nonfat dry milk and 0.05% Tween-20 (Bio Rad) were used as a standard. Standards and culture supernatants were added to the plate in duplicate, 100 µl/well, incubated at 37° C. for 1 hour, then washed 4 times in D-PBS with 0.1% Tween-20. To each well, 100 µl of mouse anti-human IgG (H+L chain) conjugated to horse radish peroxidase (Jackson Immuno Research) at 0.45 µg/ml was added and incubated for 1 hour at 37° C. Plates were washed as above. The assay was developed using an OPD reagent kit (Abbott Laboratories) and read on a Bio-Rad 96-well plate reader.

The ELISA was modified to assay for production of chimeric IgM. Plates were coated with 0.36 µg/ml goat anti-human IgM ($Fc_{5\mu}$-specific, Jackson ImmunoResearch) in D-PBS. ChromPure human IgM (myeloma, whole molecule, Jackson ImmunoResearch) was used as a standard. Peroxidase-labeled goat anti-human IgM ($Fc_{5\mu}$, Jackson ImmunoResearch) at 0.8 µg/ml was used as the enzyme antibody conjugate.

Antibody concentrations were determined by Radial Immunodiffusion (RID). Seven-fourteen day old cell culture supernatants were vortexed and then 5 or 10 µl samples for IgG and IgM, respectively, were applied to each well of human IgG or human IgM RID plates (The Binding Site, San Diego, Calif.). A set of standards (25, 50, 75, 100 and 150 µg/ml) were run on each plate. The standard for chimeric IgG1 was protein A-purified anti-P66 IgG1, and the IgM standard was ChromPure human IgM (Jackson ImmunoResearch). The plates were incubated inverted at 35–37° C. for 16–22 hours. The diameter of each ring was determined in millimeters using a RID Electronic plate reader (The Binding Site) which was calibrated with the calibration plate provided by the Binding Site.

EXAMPLE VII

Purification of Recombinant Antibody

To purify chimeric IgG1 antibodies, culture supernatants were initially dialyzed overnight against 0.1 M sodium phosphate (pH 8.2) and with 0.1% sodium azide, then filtered through a 0.2 µM filter. The preparation was then passed through a column containing PerSeptive Biosystems Poros 50A resin (Cambridge, Mass.) using a Bio Rad low-pressure chromatography system at 250–500 cm/hour. Antibody was eluted with 0.1M citrate, 0.15 M NaCl pH3.0 and pooled fractions were dialyzed against PBS (10 mM sodium phosphate, 150 mM NaCL) pH 7.2.

To purify chimeric IgM antibodies, culture supernatants were diluted 1:1 with $H_2O$ and the preparation was loaded on a column containing 175 ml DEAE FastFlow resin (Pharmacia) equilibrated with PBS at a flow rate of 10 ml/minute. Antibody was eluted with 10 mM sodium phosphate, 300 mM NaCl at pH 7.2.

EXAMPLE VIII

Toxoplasma GondII Assay i) Hybridoma Selection:

To establish the feasibility of using chimeric mouse-human monoclonal antibodies as controls and calibrators in immunoassays designed to measure human antibodies specific for an immunizing agent, a T. gondii assay was selected as a model system and represents one embodiment of the invention.

A panel of monoclonal antibodies was established from mice immunized with T. gondii. This panel was specific for many different T. gondii antigens. The first step was to identify monoclonal antibodies with desired characteristics of affinity and specificity. Monoclonal antibodies reacting to P66 and P30, two diagnostically useful proteins of T. gondii, were chosen. The monoclonal antibodies were screened on the basis of their ability to inhibit the binding of human positive plasma to T. gondii in an effort to identify those reacting to immunodominant epitopes. Based on this analysis (data not shown), two monoclonal antibodies were selected, 1-706-139 and 5-465-210, specific for P66 and P30 of T. gondii, respectively.

ii) Cloning and Sequencing of Antibody Variable Regions:

Hybridoma cells producing the monoclonal antibodies served as the source of mRNA for preparation of cDNA. To facilitate cloning of expressed H and L chain V regions, specific cDNA synthesis was primed with oligonucleotides hybridizing to the 5' end of the constant regions. For $V_H$ cDNA, IgG2b or IgG2a-specific primers were used with mRNA isolated from the hybridomas 1-706-139 and 5-465-210, respectively. Both $V_L$ cDNAs were initiated with a murine κ constant region primer. PCR amplification of the antibody V regions was performed with degenerate primers annealing to conserved $V_H$ and Vκ gene leader sequences (Jones, S. T. and Bendig, M. M., Bio/Technology 9:88–89 (1991)) in conjunction with the constant region primers. The amplification products were cloned into pUC18 and sequenced. Multiple clones of each PCR-product were sequenced to resolve any Taq polymerase induced errors.

The $V_H$ and $V_L$ cDNA sequences isolated from hybridoma 5-465-210 are shown in FIGS. 6 and 7 in their final cassette format. The $V_H$ cDNA encodes a complete V region gene consisting of a leader sequence, $V_H$ gene, and a D region rearranged to $J_H2$. The $V_H$ gene appears to be a member of murine subgroup IIB (Kabat E. A. et. al., Sequences of Proteins of Immunological Interest, 5th edition, U.S. Department of Health and Human Services, Bethesda, Md. (1991)). The degenerate leader-region amplification primer extended to nucleotide 41, so the authentic cDNA sequence begins at position 42 and extends to position 430. The $V_{L\ d}$ cDNA consists of a leader sequence and Vic gene rearranged to a Jκ-minigene. The Vκ gene is apparently a member of the VκIII subgroup. The Jκ segment contains four mismatches from the published germline sequence of the Jκ2-minigene isolated from the BALB/c mouse strain (Sakano, H. et. al., Nature 280:288-294 (1979); Max, E. E. et. al., Pro. Nat'l Acad. Sci. USA 76:3450-3454 (1979); Max, E. E. et. al., J. Biol. Chem. 256:5116–5120 (1981)). These mismatches may reflect somatic mutations or represent differences in the germline sequence as Swiss Webster mice were utilized in this study. The degenerate leader-region primer used to isolate the expressed Vk region extended to nucleotide 45, thus authentic cDNA sequence extends from position 46 through position 409.

The $V_H$ cDNA sequence cloned from hybridoma 1-706-139 is illustrated in FIG. 8. The degenerate leader-region PCR primer ends at residue 41, so authentic cDNA sequence extends from position 42 through 434. The expressed $V_H$ region includes leader sequences, a $V_H$ gene, apparently from subgroup IIA (Kabat E. A. et. al., Sequences of Proteins of Immunological Interest, 5th edition, U.S. Department of Health and Human Services, Bethesda, Md. (1991)), a D segment and $J_H4$-minigene. The exact boundary between the D and $J_H4$ segments could not be determined. The sequence of the $V_L$ cDNA isolated from hybridoma 1-706-139 is given in FIG. 9. The primer used to amplify the $V_L$ fragment ended at nucleotide 42 so the actual cDNA sequence extends from 43 through 405. The $V_L$ cDNA is comprised of a leader sequence and a Vκ gene, likely from subgroup VκII, rearranged to Jκ1.

iii) Expression Vector Construction:

The objective of this study was to produce chimeric mouse-human antibodies containing V regions derived from the murine hybridomas and human constant regions. To facilitate expression, the $V_H$ and $V_L$ chain cDNAs were modified so as to contain a complete 5' leader sequence, 3' splice donor site, and flanking cloning sites. The $V_H$ and $V_L$ transfer cassettes (FIGS. 6–9) were generated by PCR amplification with synthetic oligonucleotides containing the required elements at their 5' ends and 3' sequences specific for each V region. An appropriate leader sequence was determined for each V gene based on its homology to other V region sequences in the database that included their native leader sequence. In all cases, the leader-V region intron has been eliminated. A splice donor site was recreated in each V region cassette at the 3' end of the VDJ or VJ exons of the cDNAs by incorporating a synthetic intron fragment. The splice site junction between the V and constant regions serves to maintain the integrity of both coding sequences. Moreover, this enables the V cassettes to be placed upstream of any constant region, adding to the versatility of the system.

The modified cDNAs were then introduced into mammalian expression vectors downstream of regulatory sequences that provide for high level expression. The vector, pdHL2 (FIG. 3) contains transcriptional units for antibody H and L chain genes both under the control of a mouse immunoglobulin H-chain enhancer and metallothionein I promoter. Plasmid pdHL2 contains human kappa (Cκ) and IgG1 (Cγ1) constant region genes in their genomic configuration (Gillies et. al., J. of Immunol. Methods 125:191–202 (1989)). Introduction of the murine $V_H$ and Vκ region cassettes results in expression of mouse-human chimeric antibody. In addition, pdHL2 contains a mutated DHFR gene allowing for selection of transfectants based on MTX resistance (Gillies et. al., J. of Immunol. Methods 125:191–202 (1989)). The 5-465-210 $V_H$ and Vκ cDNA cassettes were introduced into pdHL2, generating the expression vector pdHL-2/5-465. This vector encodes chimeric IgG1 antibody specific for P30. Similarly, the 1-706-139 $V_H$ and Vκ region cassettes were cloned into pdHL2 yielding pJH9-14-94/4.1, encoding chimeric IgG 1 antibody specific for P66 antigen.

Figure 4:
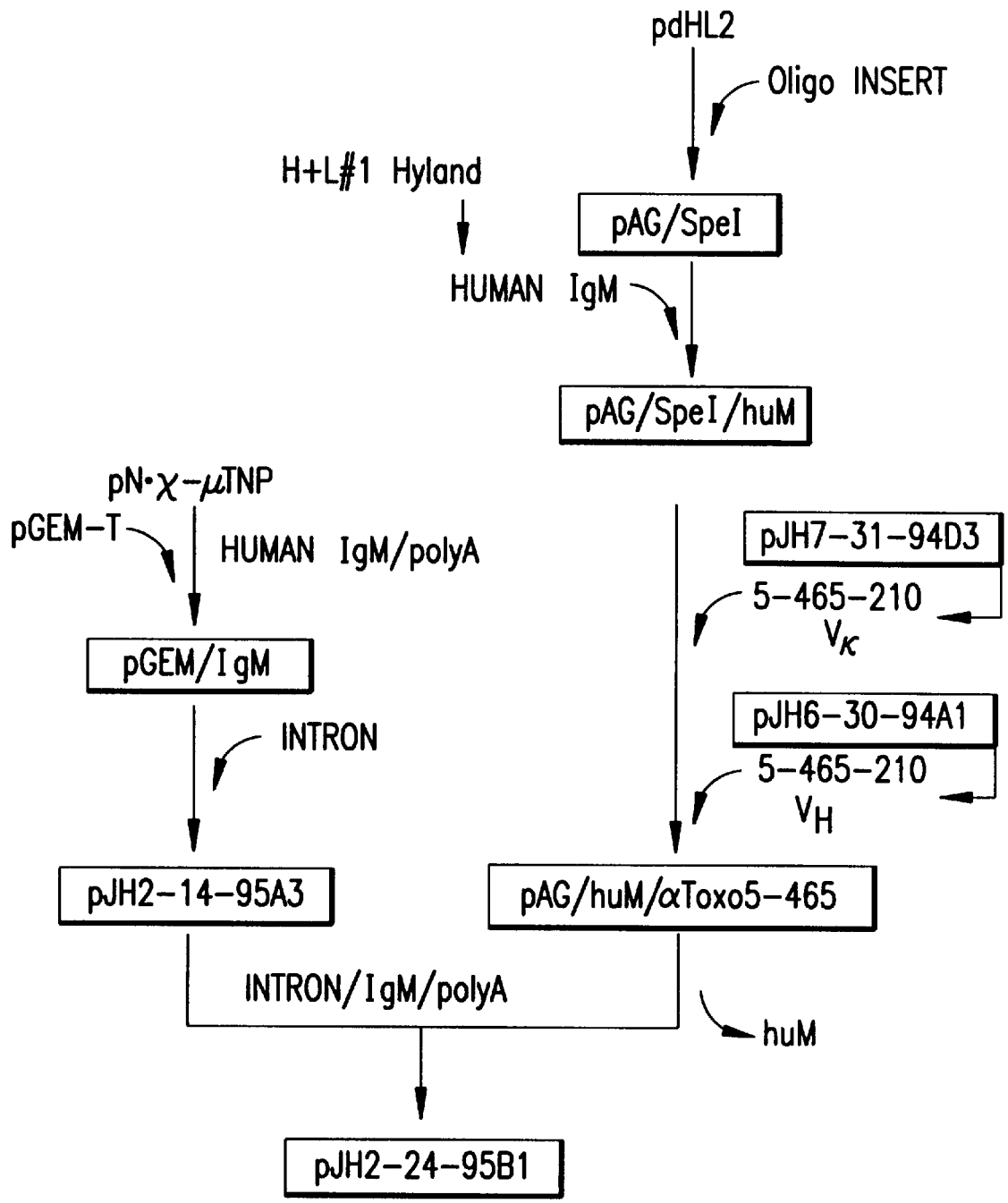
FIG. 4 shows a diagrammatic representation of the key steps involved in generating the expression construct pJH2-24-95B 1. This expression vector encodes a mouse-human chimeric IgM antibody comprised of H and L chain V regions from the mouse hybridoma 5-465-210 and human constant region genes. The chimeric antibody is specific for P30 of T. gondii.

To produce chimeric mouse-human IgM class antibodies, pdHL2 was modified by replacement of the Cγ1 gene with a genomic clone of the human IgM (Cμ) gene (FIG. 4). The expression vector containing Cμ was designated pAG/SpeI/huM. In this first generation IgM vector, 3' untranslated and poly A signal sequences originally present downstream of Cγ1 were maintained. Chimeric IgM expression constructs were generated by sequential transfer of the Vκ and $V_H$ cassettes into this vector. In preliminary experiments with these constructs, all transfectants had very low secretion levels (<1 μg/ml) of chimeric IgM (data not shown).

In an effort to enhance chimeric IgM production, new constructs were generated in which the Cμ gene and the poly A signal sequences (originally downstream of Cγ1) were replaced with a genomic clone of the secretory portion of human Cμ including native 5' intron (contains splice acceptor site), 3' untranslated, and poly A signal sequences (FIG. 4). Sequence analysis of the Cμ clone revealed only a single base change relative to the published germline sequence (Word C. J. et. al., International Immunology 1:296–309 (1989)), the insertion of a T between residues 1583 and 1584 in the Cμ3–Cμ4 intron. This alteration would not be expected to effect expression of the Cμ gene. The IgM expression construct containing the 5-465-210 $V_H$ and Vκ regions was designated pJH2-24-95B1 (FIG. 3). Replacement of the 5-465-210 V region set with a Xba I-Hind III fragment containing the 1-706-139 $V_H$ and Vκ cassettes (FIG. 5), yielded plasmid pJH3-19-95A, encoding chimeric IgM specific for P66.

iv) Expression of Chimeric Antibodies:

The chimeric antibody expression constructs were transfected into the non-producing Sp2/0-Ag14 cells. Both chimeric IgG1 constructs were introduced by electroporation whereas the chimeric IgM constructs were transfected by protoplast fusion. Transfectants were selected in the presence of 0.1 μM MTX. Multiple MTX-resistant colonies from each transfection were screened for production of chimeric antibody using an anti-human antibody ELISA. Those that tested positive were expanded and cloned. Secretion levels of the transfectomas were determined by radial immunodiffusion (Table 5). Clones secreting high levels of chimeric antibody were further subcloned. The observed production levels for the anti-P30 and anti-P60 chimeric IgG1 antibodies were 90 μg/ml or greater. A transfectant secreting anti-P30 chimeric IgM antibody at levels in excess of 100 μg/ml was obtained by protoplast fusion. Transfection of the anti-P66 chimeric IgM construct has met with more limited success. Transfectomas secreting the chimeric IgM have been obtained, but secretion levels have been rather low (<1 μg/ml). All of these transfectants have been maintained on 0.1 μM MTX. Based on previous studies, increasing the MTX concentration may further augment production of the chimeric antibodies (Gillies et. al., J. of Immunol. Methods 125:191–202 (1989); Lo, K. -M. and S. D. Gillies, Biochimica et Biophysica Acta 1088:217–224 (1991)). In three out of four cases, the expression levels of recombinant chimeric antibody produced by the transfectomas actually exceeded the antibody production levels of the hybridomas from which they were derived. Secretion levels required to allow for economical manufacturing have been achieved. Another advantage of the recombinant system is that one can readily generate different classes of antibodies (i.e. IgG1 and IgM) with identical binding specificities.

Table 5 below represents the expression levels of the chimeric antibodies produced using the above procedures:

TABLE 5

Chimeric Antibody Expression Levels

| Clone | Specificity | Isotype | Secretion level* (μg/ml) |
|---|---|---|---|
| 157-465GS | P30 | IgG1 | 94 |
| 243-465GS | P30 | IgG1 | 116 |
| 176-706G | P66 | IgG1 | 90 |
| 224-465M | P30 | IgM | 115 |
| 223-706M | P66 | IgM | 0.74 |

*Cells were seeded at a density of $0.5 \times 10^6$. Expression levels were determined at day 7 for the clones or day 14 for subclones (S) by RID assay.

v) Assay Performance of the Chimeric Antibodies:

To determine whether the chimeric antibodies had retained their native antigen-binding activity and were capable of functioning as controls/calibrators, they were tested by immunoassay. Protein A-purified chimeric IgG1 antibodies and chimeric IgM fractionated on DEAE were examined for immunoreactivity to *T. gondii* in the Abbott Laboratories IMx Toxo IgG and IgM assays (Safford, J. W. et. al., J. Clin. Pathol. 44:238–242 (1991)). These assays are automated Microparticle Enzyme Immunoassays (MEIA) designed for quantitative (IgG) and qualitative (IgM) measurement of antibodies to *T. gondii* in human serum and plasma.

Figure 2:
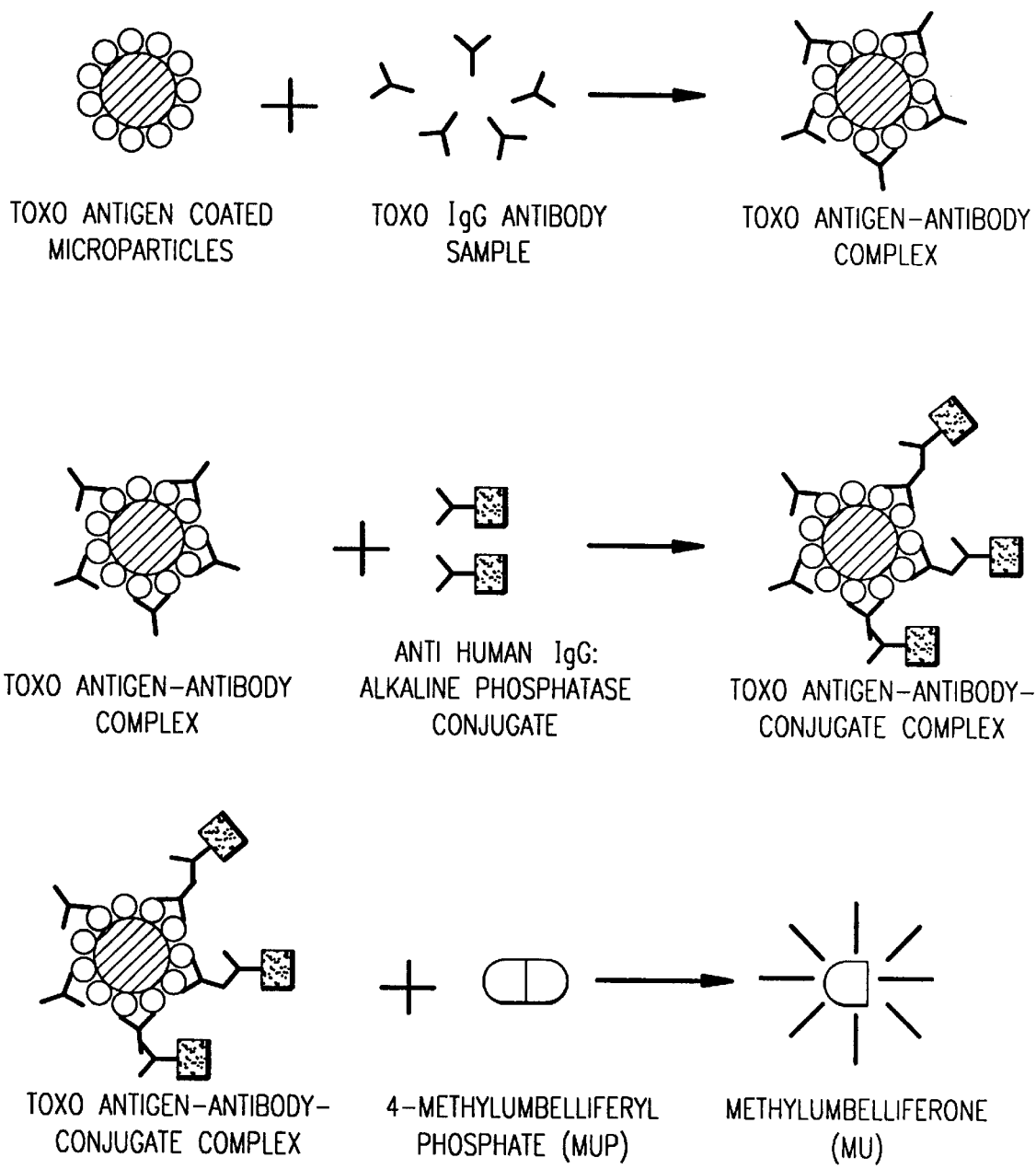
FIG. 2 depicts the steps involved in the Abbott IMx Toxo IgG automated antibody capture-type immunoassay.

The basic steps of the IMx Toxo IgG assay are depicted in FIG. 2. The assay uses microparticles coated with *T. gondii* antigens as the solid phase. Specimen is added to the coated microparticles to allow antibodies specific for *T. gondii* to bind. The microparticles are then transferred onto a glass fiber matrix and washed extensively to remove any unbound antibody. Subsequently, alkaline phosphatase conjugated goat anti-human IgG antibody is added that binds specifically to IgG class antibodies complexed to the *T. gondii* antigens on the microparticles. Unbound antibody is washed away and the antigen—patient IgG—anti-human IgG conjugate complex is detected by addition of the substrate 4-Methylumbelliferyl Phosphate (MUP). Dephosphorylation of MUP by the alkaline phosphatase can be assessed by the rate of formation of the fluorescent compound Methylumbelliferone (MU) measured on the IMx instrument (Fiore, M. et. al., Clin. Chem. 34:1726–1732 (1988)). This quantitative assay includes a set of 6 calibrators to establish a calibration curve. Calibrators are prepared with human anti-*T. gondii* IgG antibody diluted into human serum at six different concentrations 0, 10, 50, 75, 150, and 300 IU IgG antibody/ml. The calibrators are referenced to the World Health Organization International Standard for anti-*T. gondii* serum. The calibrators are run in place of the specimen and a calibration curve is plotted. Results are interpolated from the six point calibration curve to quantitate IgG levels in the specimens. For this assay, the anti-*T. gondii* IgG positive control is prepared with 20 IU/ml human anti-*T. gondii* IgG diluted into human serum.

The IMx Toxo IgM assay manufactured by Abbott Laboratories is an automated MEIA designed for qualitative measurement of IgM antibodies to *T. gondii*. The assay format is similar to the IMx Toxo IgG assay but the alkaline phosphatase conjugate is goat anti-human IgM antibody. The assay result is expressed as an index value which is the ratio of the specimen counts over the index calibrator. The index calibrator is prepared with human anti-*T. gondii* IgM antibody in human serum and is set near the positive/negative cutoff. The positive control is prepared in the same manner and set to give an index value of 1.5× the index calibrator.

Figure 10:
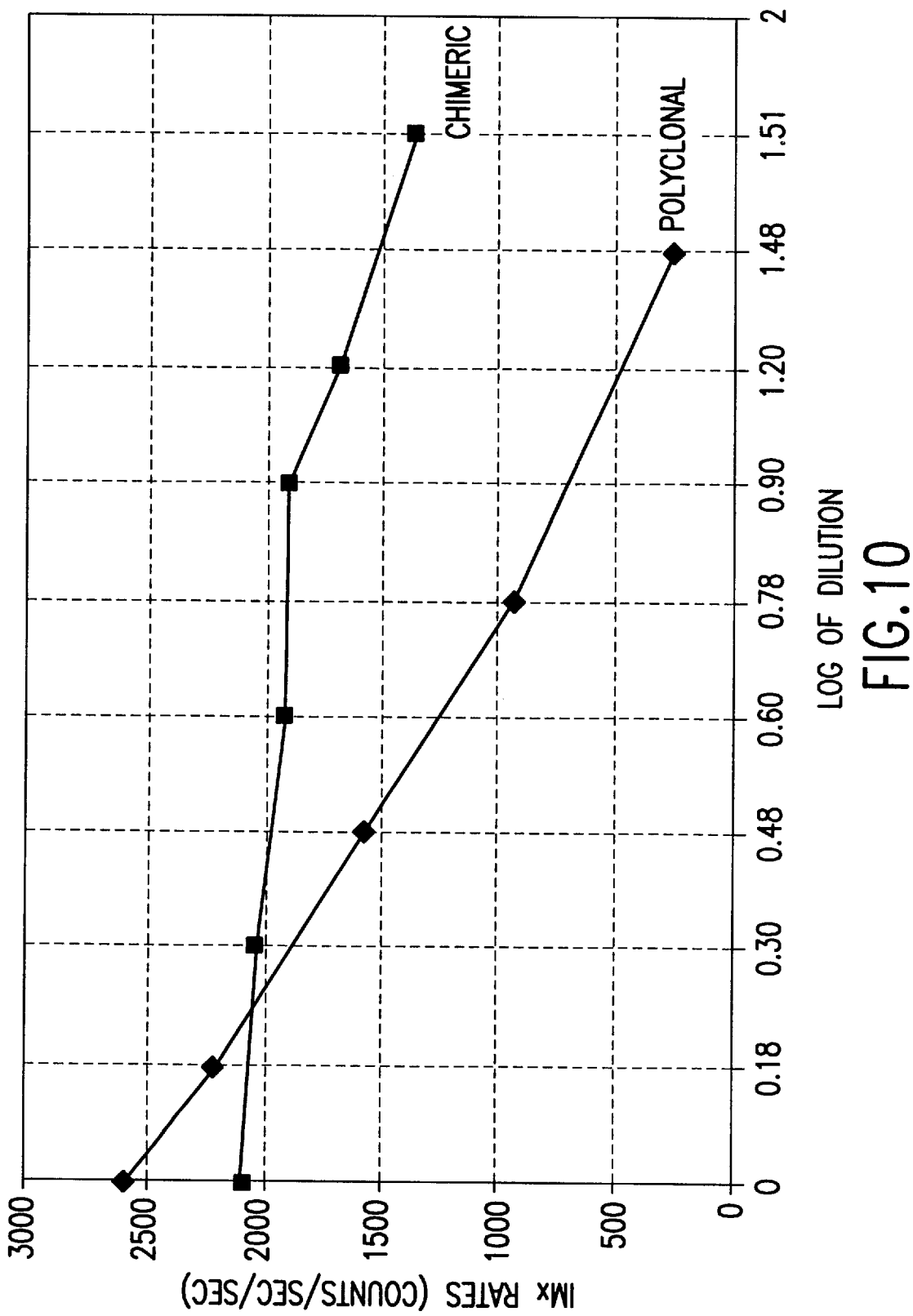
FIG. 10 shows a calibration curve for the anti-P66 chimeric IgG as compared with the positive human serum derived calibrator in the IMx Toxo IgG assay. Rate counts (counts/sec/sec) are shown on the Y-axis.

Two-fold serial dilutions of purified anti-P66 chimeric IgG1 antibody at an initial concentration of 11.59 mg/ml and IMx Toxo positive control serum were made in negative human serum (calibrator diluent). The dilutions were run in duplicate and rate counts were determined. The anti-P66 chimeric IgG1 antibody had a flattened curve at concentrations greater than 0.7 mg/ml, reaching a rate count of 2070 at 11.59 mg/ml (FIG. 10). The rate count of the 300 IU/ml calibrator (IMx calibrator F) was 2572. Flattening at the top end of the curve seen with the anti-P66 chimeric IgG1 antibody probably reflects saturation of the anti-P66 binding sites in the IMx kit.

Figure 11:
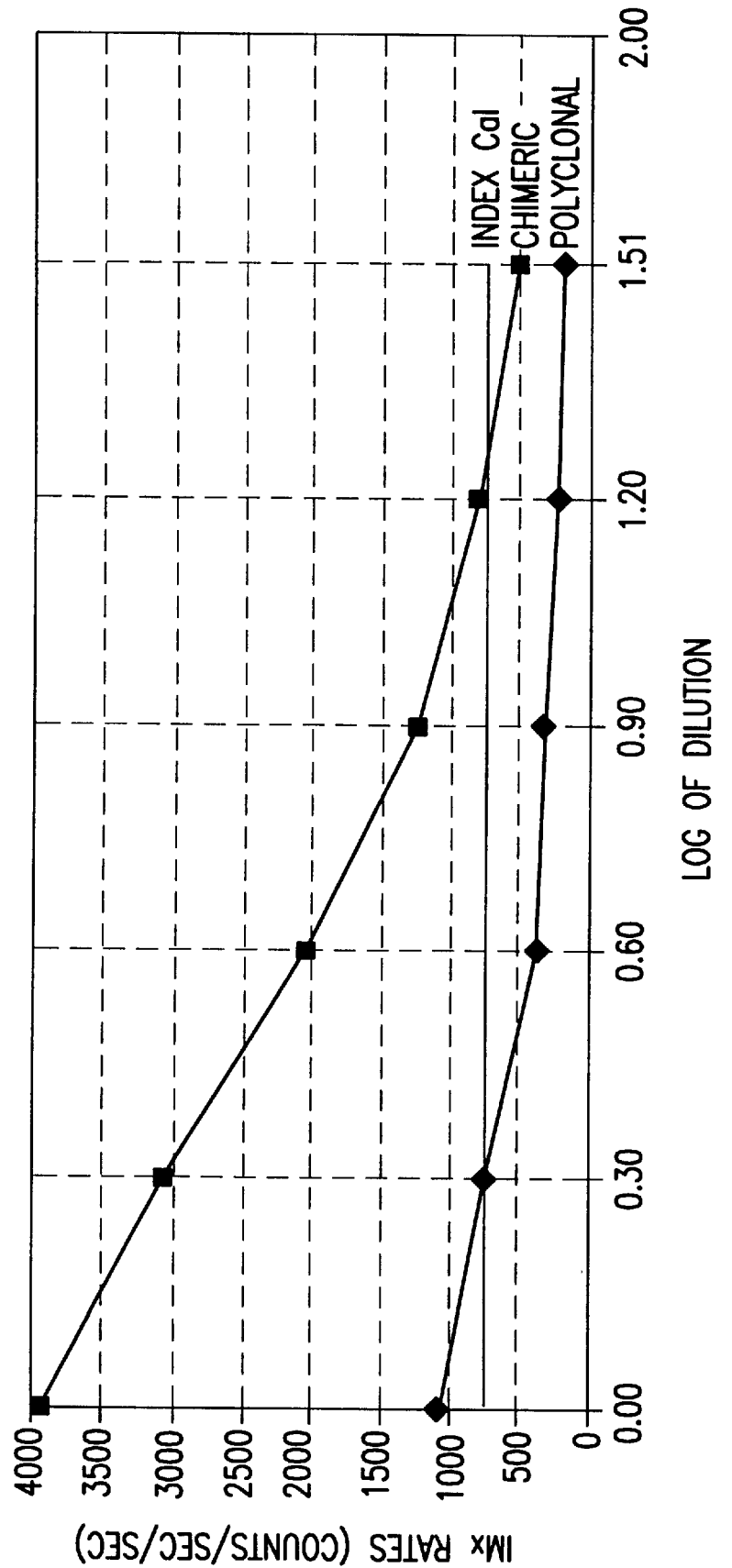
FIG. 11 illustrates a calibration curve obtained for the anti-P66 chimeric IgM antibody as compared to the positive human serum derived calibrator in the IMx Toxo IgM assay. The index calibrator of 710 rates (rate counts=counts/sec/sec) was matched by the anti-P66 chimeric IgM at a concentration of 12.3 μg/ml.

To examine the performance of a monoclonal chimeric IgM antibody, purified anti-P66 IgM at 0.210 mg/ml and the IMx Toxo IgM positive control were diluted serially two-fold in index calibrator diluent. These dilutions were run in duplicate and compared to the positive control and index calibrator (FIG. 11). Predicted values for equivalent rate counts to the positive control and index calibrator were read off the dilution curves to determine antibody concentration. The index calibrator rate of 710 and positive control rate of 1078 were achieved at 0.0123 mg/ml and 0.0209 mg/ml of chimeric IgM, respectively. These data demonstrate that the monoclonal anti-P66 chimeric IgM functions as an acceptable index calibrator and positive control in this assay. Thus, it appears that the anti-P66 chimeric antibody can substitute for positive human plasma in the manufacture of index calibrator and positive control for this assay. In contrast to the anti-P66 chimeric IgG1, the rate counts do not appear to plateau even at the highest concentration tested. This may be due to the structural differences between IgG1 and IgM, as the epitope density would be expected to be roughly equivalent in the two assays. Most IgM is secreted as a pentamer, providing a greater number of constant region epitopes, as compared to the dimeric structure of IgG1. Presumably, in the case of the Toxo IgM assay, more of the enzyme-linked secondary antibody (anti-human IgM) binds to the antigen-antibody complex, as compared to the Toxo IgG assay (anti-human IgG), leading to further amplification of the signal.

Figure 12:
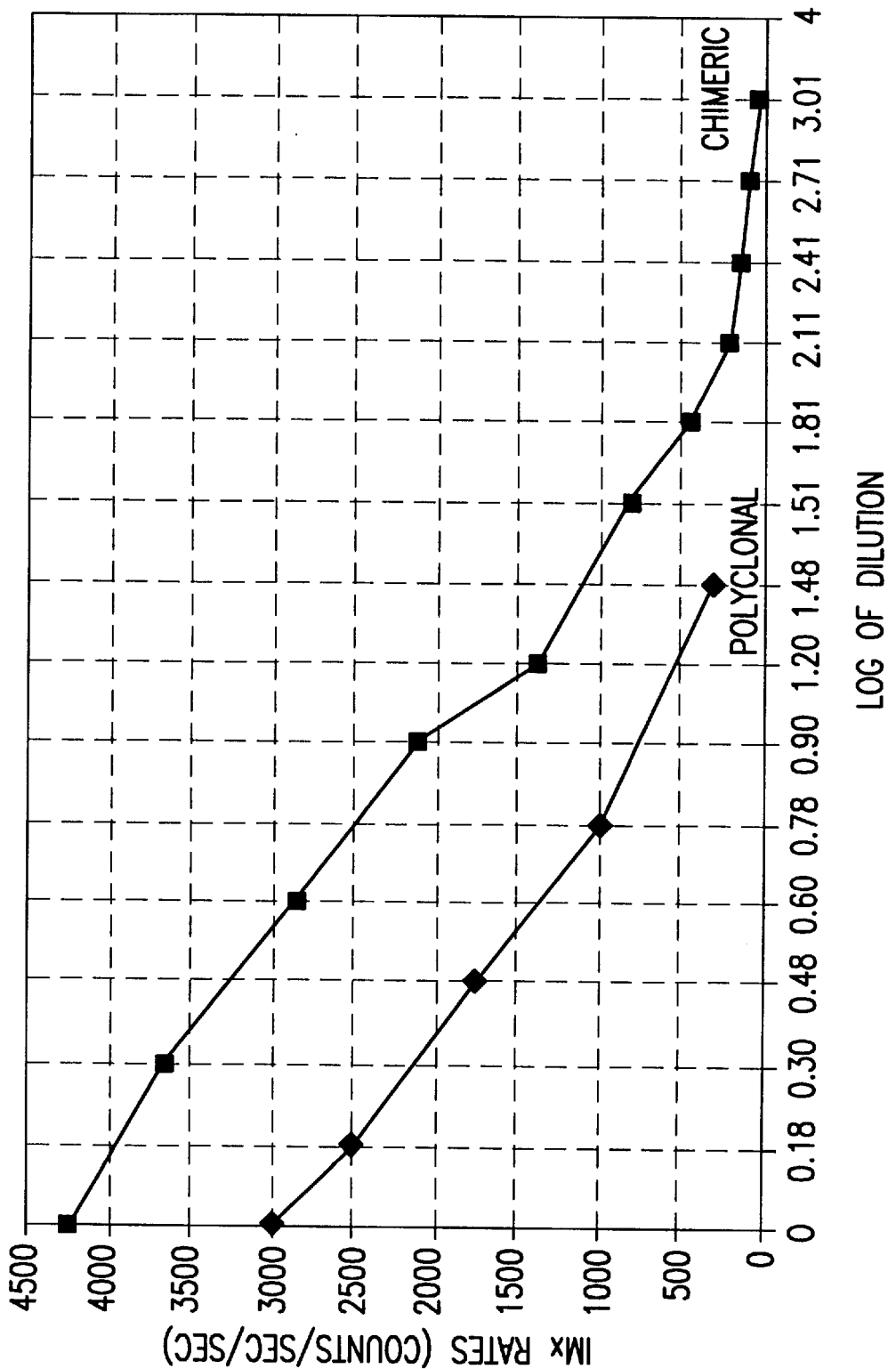
FIG. 12 represents a calibration curve for the anti-P30 chimeric IgG as compared with positive human serum currently used as the calibrator in the IMx Toxo IgG assay. Rate counts (counts/sec/sec) are shown on the Y-axis.

Purified anti-P30 chimeric IgG1 antibody at a concentration of 0.87 mg/ml and IMx Toxo positive human serum (calibrator F, 300 Iu/ml) were diluted serially two-fold in calibrator diluent to provide antibody levels across the dynamic range (0–300 IU/ml) of the assay. These dilutions were run in duplicate and rate counts (counts/sec/sec) were read off the dilution curves. The chimeric anti-P30 IgG1 antibody and positive control serum had parallel dilution curves (FIG. 12). The 300 Iu/ml human serum calibrator (F calibrator) had a rate count of 3015. The anti-P30 chimeric IgG1 reached an equivalent rate count at a concentration of 0.11 mg/ml. No flattening of the curve obtained with the anti-P30 chimeric antibody was observed up to the 4261 rate counts observed at a concentration of 0.87 mg/ml. Based on these data, the anti-P30 chimeric IgG1 achieved an acceptable signal for an IMx calibration curve. These data demonstrate that one chimeric antibody, specific for a single epitope on P30, has the potential to replace positive human serum used as calibrators and controls in this assay.

Figure 13:
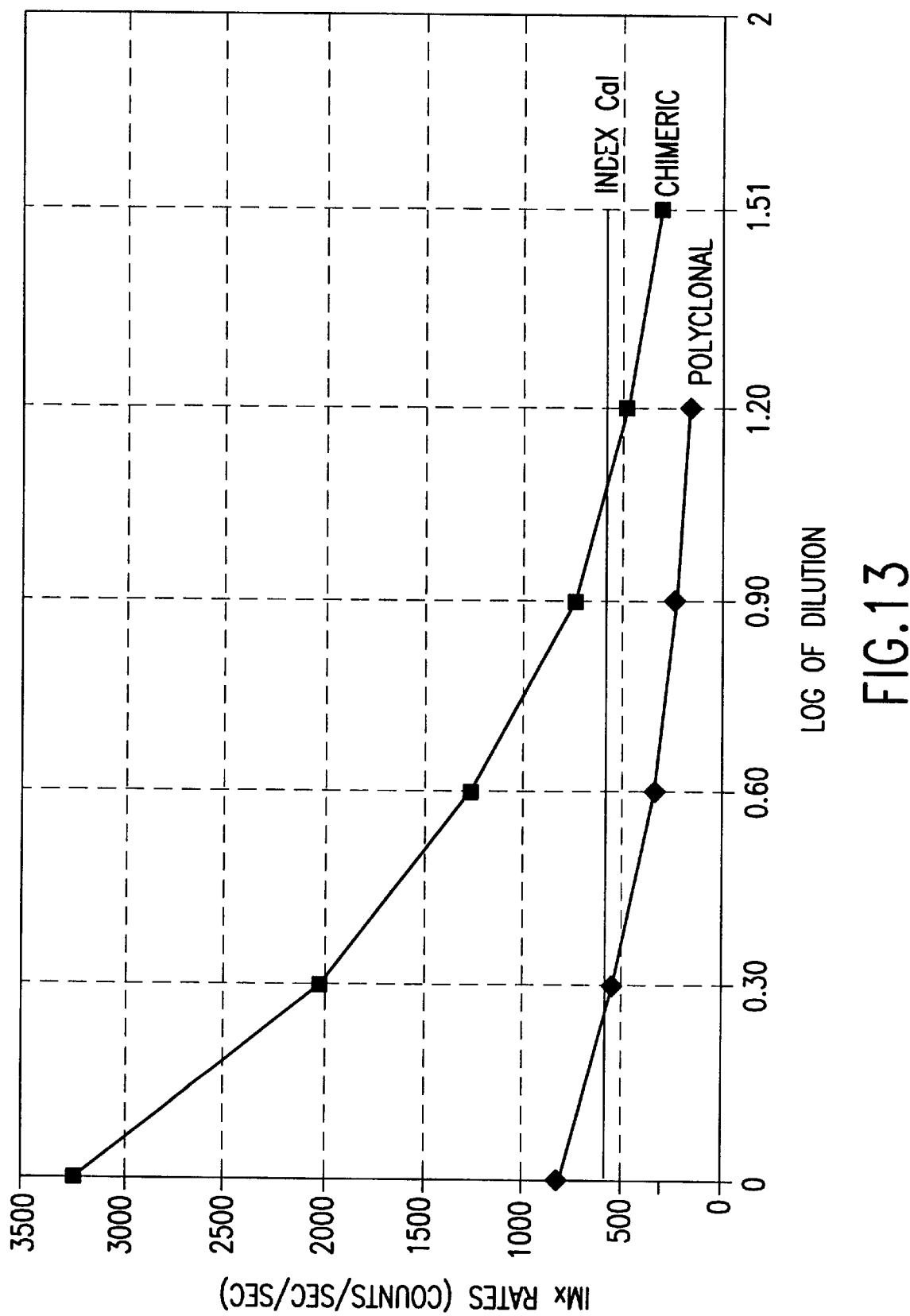
FIG. 13 illustrates a dilution curve run on the IMx for the anti-P30 chimeric IgM antibody along with positive human serum for the calibrators. The index calibrator of 560 rates (rate counts=counts/sec/sec) was successfully matched by the anti-P30 chimeric IgM at a concentration of 8.4 μg/ml.
Figure 14:
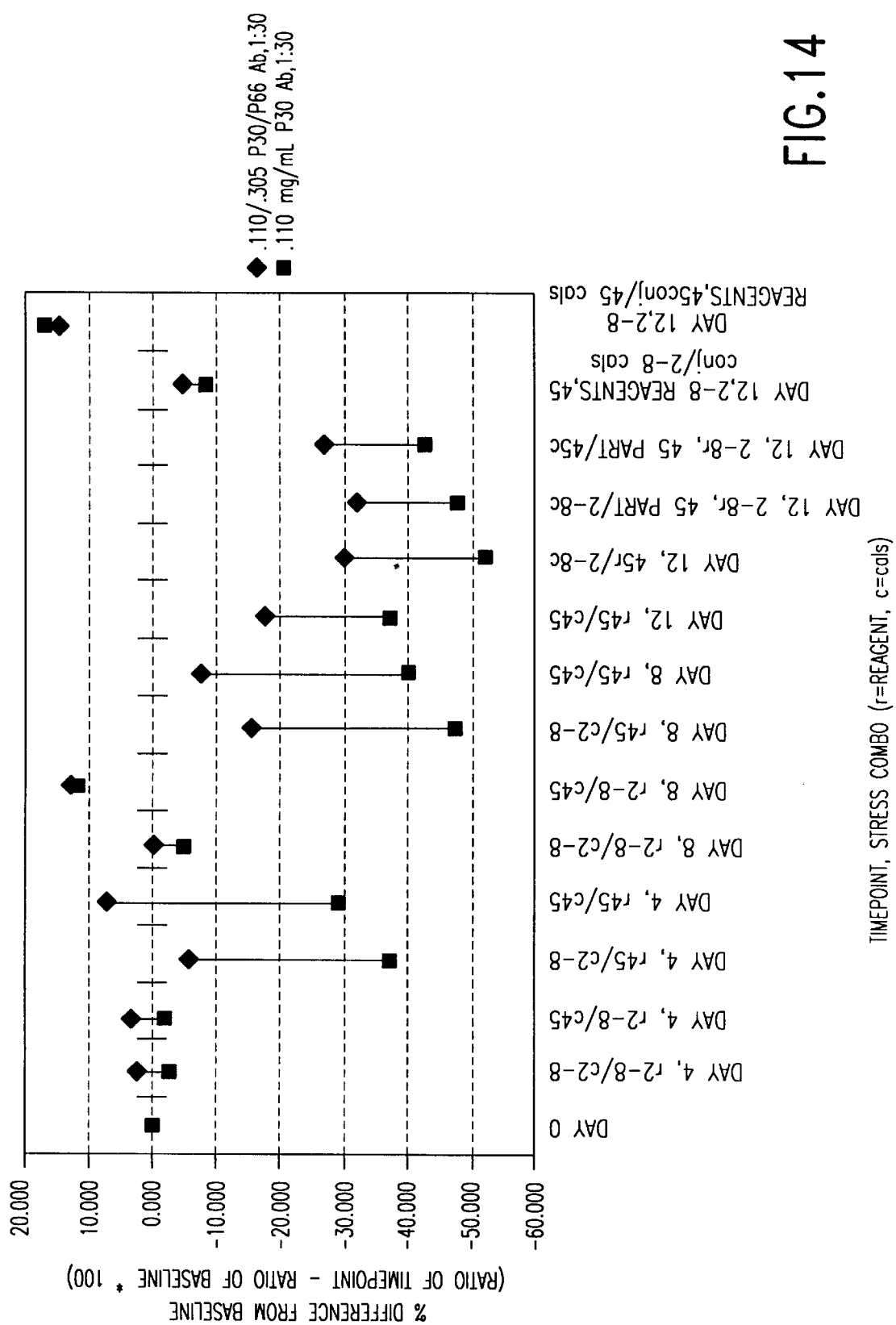
FIG. 14 represents an accelerated stability analysis run on all reagents at 45° C. at the B calibrator level (0.0036 mg/mil anti-P30+0.010 mg/ml anti-P66). No difference was observed for the chimeric IgG recombinant antibodies as compared to the human serum calibrator. However, by day 12, 40% of the P30 epitope on the microparticles is no longer recognized by the anti-P30 chimeric antibody. r=assay reagents; c=calibrator

To examine the performance of a chimeric IgM antibody, purified anti-P30 IgM at 0.104 mg/ml and the IMx Toxo IgM positive control were diluted in index calibrator diluent in two-fold serial dilutions. These dilutions were run in duplicate and compared to the positive control and index calibrator (FIG. 13). Predicted values for equivalent rate counts to the positive control and index calibrator were read off these dilution curves and concentrations of antibody determined. The index calibrator rate of 560, and positive control rate of 1050 were achieved at 0.0084 mg/ml and 0.0145 mg/ml of anti-P30 chimeric IgM, respectively. These data demonstrate that an acceptable IMx cutoff value can be obtained with the monoclonal anti-P30 chimeric IgM antibody.

vi) Examination of Accelerated Reagent Stability:

An accelerated stability analysis of the chimeric IgG antibodies in the Toxo IgG assay format was performed by heat-stressing components at 45° C. for up to 12 days. For the anti-P30 chimeric IgG1 and a mixture of the two monoclonals (anti-P30+anti-P66 IgG1), dilutions were run in duplicate against the assay calibration curve in the IMx Toxo IgG assay. A point to point curve fit was used to predict concentrations of chimeric antibodies needed to match the current human antibody calibrators. For the stability analysis, two calibrators levels were examined, the B calibrator of 10 IU/ml and F calibrator of 300 IU/ml. Rate counts equivalent to the B calibrator were achieved with 0.0036 mg/ml of anti-P30 IgG1 or with a mixture of 0.0036 mg/ml anti-P30 and 0.010 mg/ml anti-P66 IgG1. The kit reagents and calibrators were stored for up to 12 days at 2–8° C. or 45° C. On days 0, 4, 8 and 12, assays were run with the test reagents and performance was plotted against the standard human B calibrator (FIG. 14). All kit reagents and the chimeric antibodies were stable at 2–8° C. In contrast, when kit reagents were stored at 45° C., by day 4, there was a 30% reduction in rate counts observed for the anti-P30 IgG1 as compared to the standard human B calibrator. By day 12 at 45° C., the signal obtained with the anti-P30 IgG1 was reduced by approximately 50%. The loss of activity was not due to a lack of stability of the chimeric IgG1, as under these conditions, it was as stable as the standard human calibrator antibodies. The reduction in rate counts appears to be due to loss of the P30 epitope recognized by this monoclonal chimeric antibody. When the chimeric antibody mixture was examined, the performance characteristics were similar to that seen for the human antibody calibrator. It would appear the P66 epitope recognized by the monoclonal anti-P66 antibody is more stable under these conditions, and that it compensates for the heat-stress induced loss of the P30 epitope.

Figure 15:
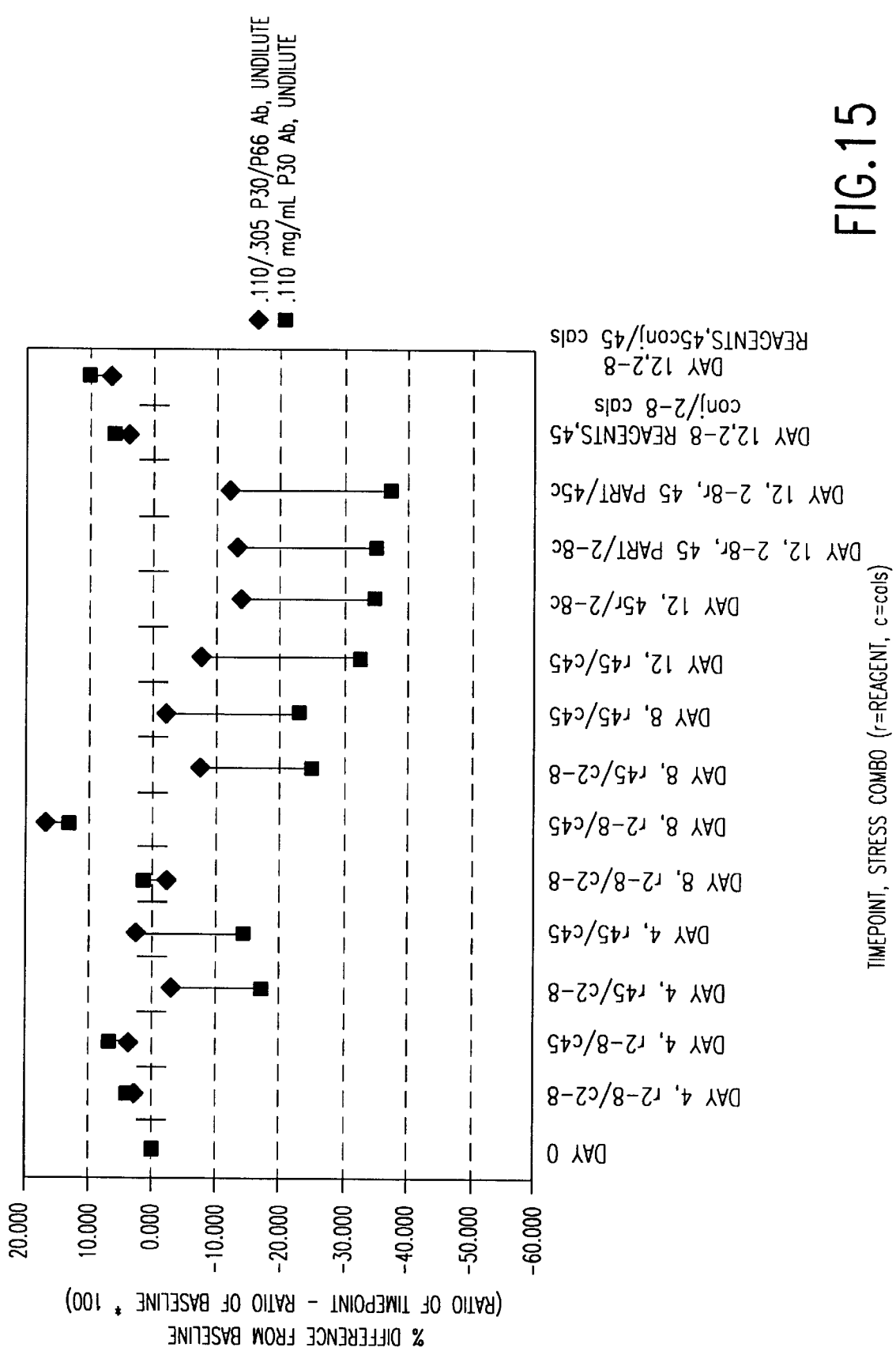
FIG. 15 shows an accelerated stability analysis of reagents stored at 45° C. using F calibrator dilutions (0.11 mg/ml anti-P30+0.305 mg/ml anti-P30). No difference was observed for the chimeric IgG recombinant antibodies as compared to the human serum calibrator. However, by day 12, 40% of the P30 epitope on the microparticles is no longer recognized by the anti-P30 chimeric antibody. r=assay reagents; c=calibrator

To achieve F calibrator levels, 0.110 mg/ml of anti-P30 IgG1 or a mixture of 0.110 anti-P30 and 0.305 mg/ml anti-P66 IgG1 were used. Assay performance with the test reagents relative to that seen with the standard human calibrator is shown in FIG. 15. All kit reagents and the chimeric antibodies were stable when stored at 2–8° C. Similar to the results observed at the B calibrator level, there was a progressive decline in rate counts observed with the anti-P30 antibody when stored at 45° C. The combination of the anti-P30 and anti-P66 monoclonals, exhibited acceptable stability characteristics as compared to the native human F calibrator even after heat-stress at 45° C. The loss of stability with the anti-P30 chimeric antibody appears to be due to loss of the P30 epitope recognized by this monoclonal, as the chimeric anti-P30 antibody showed no difference in stability relative to the human calibrator antibodies.

Figure 16:
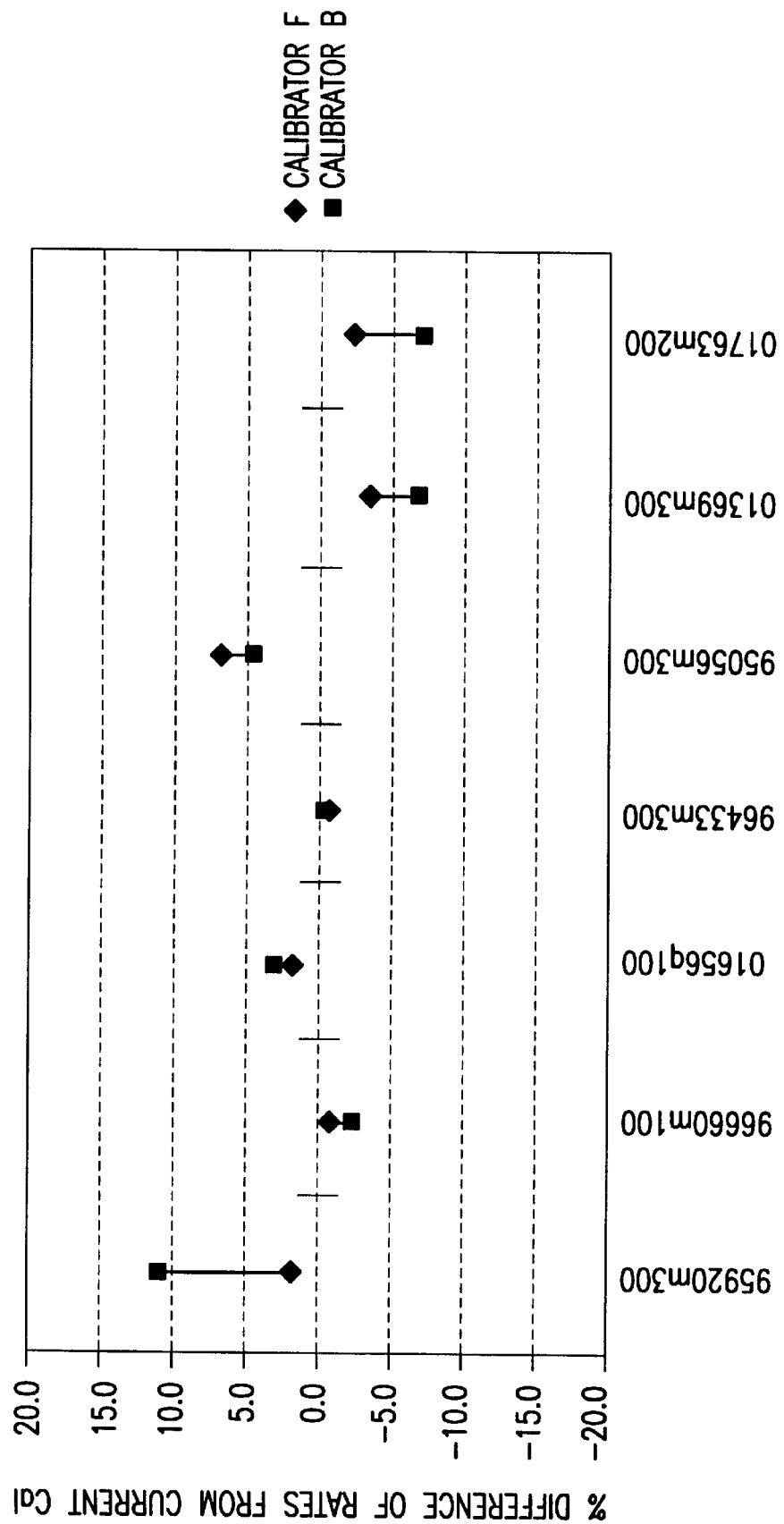
FIG. 16 illustrates a comparison of a mixture of monoclonal antibodies equivalent to the B calibrator (0.0037 mg/ml anti-P30 IgG1+0.020 mg/ml anti-P66 IgG1) or F calibrator (0.11 mg/ml anti-P30 IgG1 and 0.61 mg/ml anti-P66 chimeric IgG1) with calibrators (cals) manufactured with positive human serum versus 7 independent antigen (Ag) lots. r=assay reagents; c=calibrator

These data demonstrate that chimeric antibodies can be produced that have stability characteristics suitable for commercial manufacturing. The slow decay seen with heat-stress of the P30 epitope highlights the importance of carefully choosing the epitope recognized by the chimeric antibody. In this case, a comparison was made between the binding characteristics of a monoclonal chimeric antibody and those of a polyclonal antiserum. In the latter case, multiple epitopes on a given antigen (e.g. P30) are being recognized, and the loss of any single one may not be discernible. An advantage of this technology is that one can screen candidate murine monoclonal antibodies for desired properties prior to cloning of the V regions and producing the chimeric antibody. The properties of the chimeric antibody will reflect those of the original donor antibody. For the IMx Toxo IgG assay, by blending the anti-P30 and anti-P66 chimeric antibodies, the combined characteristics provide a performance level equivalent to the standard human antibody calibrators. This establishes that chimeric antibodies can be utilized as controls and calibrators in place of positive human serum. In some cases, a single monoclonal chimeric antibody may suffice. In other cases, it may be necessary to pool more than one chimeric antibody to reach desired assay performance characteristics.

vii) Analysis of Lot-to-Lot Antigen Variation:

To examine whether there was significant lot-to-lot variation in the expression of the P30 and P66 epitopes recognized by the chimeric antibodies, mixtures of the anti-P30 and anti-P66 chimeric antibodies at the B calibrator and F calibrator levels were tested with multiple lots of antigens. The results of this analysis with seven independent lots of antigens is shown in FIG. 16. Performance of both mixtures of anti-P66 and anti-P30 chimeric antibodies were comparable (within assay variability) to the current IMx human serum calibrator. This further validates the potential of mouse-human chimeric antibodies as a substitute for positive human antibodies.

We claim:

1. A method for detecting the presence of antibody which may be present in a test sample wherein said method comprises (A) contacting said test sample suspected of containing said antibody with antigen specific for said antibody for a time and under conditions sufficient to allow the formation of antigen/antibody complexes, (B) detecting the presence of said antibody which may be present in said test sample and employing, as a control or calibrator, a reagent which binds to said antigen, wherein the improvement comprises employing, as said control or calibrator, a chimeric antibody comprising murine heavy and light chain variable regions genetically fused to human or a species immunologically cross0reactive with human heavy and light chain constant regions, wherein said chimeric antibody binds to said antigen and is homogeneous with respect to specificity and affinity.

2. A method for detecting the presence of antibody which may be present in a test sample wherein said method comprises (A) contacting said test sample suspected of containing said antibody with at least one antigen specific for said antibody for a time and under conditions sufficient to allow the formation of antigen/antibody complexes, (B) detecting the presence of said antibody which may be present in said test sample, and employing, as a control or calibrator, two or more reagents which bind to said at least one antigen, wherein the improvement comprises employing, as said control or calibrator, in place of said test sample, two or more chimeric antibodies, wherein each is homogeneous with respect to specificity and affinity and each comprises murine heavy and light chain variable regions genetically fused to human or a species immunologically cross0reactive with human heavy and light chain constant regions, wherein 1) each of said two or more chimeric antibodies binds to an antigen comprising more than one epitope wherein:

a) said antigen and said two or more chimeric antibodies are present in a single container or b) said antigen and said two or more chimeric antibodies are present in separate containers such that said antigen is present with one of said two or more chimeric antibodies in one container; or 2) each of said two or more chimeric antibodies binds to a different antigen, said different antigen comprising one or more epitopes wherein:

a) two of said different antigen and said two or more chimeric antibodies are present in a single container or b) each of said two different antigens and said two or more chimeric antibodies are present in separate containers such that each of said two different antigens is present with one of said two or more chimeric antibodies in one container of said separate containers, wherein each of said different antigens may be from one source or from different sources.

3. A method for detecting the presence of antibody which may be present in a test sample wherein said method comprises (A) contacting said test sample suspected of containing said antibody with antigen specific for said antibody for a time and under conditions sufficient to allow the formation of antigen/antibody complexes, (B) adding a direct or indirect conjugate to said resulting antigen/antibody complexes for a time and under conditions sufficient to allow said conjugate to bind to said bound antibody, wherein said conjugate comprises an antibody attached to a signal generating compound capable of generating a detectable signal, (C) detecting the presence of said antibody which may be present in said test sample by detecting the signal generating by said signal generating compound, and employing, as a control or calibrator, a reagent which binds to said antigen, wherein the improvement comprises employing, as said control or calibrator, a chimeric antibody comprising murine heavy and light chain variable regions genetically fused to human or a species immunologically cross0reactive with human heavy and light chain constant regions, wherein said chimeric antibody binds to said antigen and is homogeneous with respect to specificity and affinity.

4. The method of claim 1 or 3 wherein said chimeric antibody is a chimeric monoclonal antibody comprising murine heavy and light chain variable regions genetically fused to constant regions derived from a species immunologically cross-reactive to human constant regions.

5. The method of claim 1 or 3 wherein said chimeric antibody binds specifically to *Toxoplasma gondii*.

6. The method of claim 5 wherein said chimeric antibody binds specifically to protein P30 or protein P66 of *Toxoplasma gondii*.

7. The method of claim 1 or 3 wherein said murine heavy chain variable region of said chimeric antibody is encoded by the nucleotide sequence of SEQ ID NO:2 and said murine light chain variable region of said chimeric antibody is encoded by the nucleotide sequence of SEQ ID NO:4.

8. The method of claim 1 or 3 wherein said murine heavy chain variable region of said chimeric antibody has the amino acid sequence of SEQ ID NO:1 and said murine light chain variable region of said chimeric antibody has the amino acid sequence of SEQ ID NO:3.

9. The method of claim 1 or 3 wherein said murine heavy chain variable region of said chimeric antibody is encoded by the nucleotide sequence of SEQ ID NO:6 and said murine light chain variable region of said chimeric antibody is encoded by the nucleotide sequence of SEQ ID NO:8.

10. The method of claim 1 or 3 wherein said murine heavy chain variable region of said chimeric monoclonal antibody has the amino acid sequence of SEQ ID NO:5 and said murine light chain variable region of said chimeric antibody has the amino acid sequence of SEQ ID NO:7.

11. A method for detecting the presence of antibody which may be present in a test sample wherein said method comprises (A) contacting said test sample suspected of containing said antibody with at least one antigen specific for said antibody for a time and under conditions sufficient to allow the formation of antigen/antibody complexes, (B) adding a direct or indirect conjugate to said resulting antigen/antibody complexes for a time and under conditions sufficient to allow said conjugate to bind to said bound antibody, wherein said conjugate comprises an antibody attached to a signal generating compound capable of detecting a detectable signal, (C) detecting the presence of said antibody which may be present in said test sample by detecting the signal generated by said signal generating compound, and employing, as a control or calibrator, two or more reagents which bind to said at least one antigen, wherein the improvement comprises employing, as said control or calibrator, in place of said test sample, two or more chimeric antibodies, wherein each is homogeneous with respect to affinity and specificity and each comprises murine heavy and light chain variable regions genetically fused to human or a species immunologically cross-reactive with human heavy and light chain constant regions, wherein 1) each of said two or more chimeric antibodies binds to an antigen comprising more than one epitope wherein:
 a) said antigen and said two or more chimeric antibodies are present in a single container or
 b) said antigen and said two or more chimeric antibodies are present in separate containers such that said antigen is present with one of said two or more chimeric antibodies in one container; or 2) each of said two or more chimeric antibodies binds to a different antigen, said different antigen comprising one or more epitopes wherein:
 a) two of said different antigen and said two or more chimeric antibodies are present in a single container or
 b) each of said two different antigens and said two or more chimeric antibodies are present in separate containers such that each of said two different antigens is present with one of said two or more chimeric antibodies in one container of said separate containers, wherein each of said different antigens may be from one source or from different sources.

12. The method of claim 2 or 11 wherein each of said two or more chimeric antibodies is a chimeric monoclonal antibody comprising murine heavy and light chain variable regions genetically fused to constant regions derived from a species immunologically cross-reactive with human constant regions.

13. The method of claims 2 or 11 wherein each of said two or more chimeric antibodies binds specifically to *Toxoplasma gondii*.

14. The method of claim 13 wherein each of said two or more chimeric antibodies binds specifically to protein P30 or protein P66 of *Toxoplasma gondii*.

15. The method of claims 2 or 11 wherein said murine heavy chain variable region of said chimeric antibody representing one of said two or more chimeric antibodies is encoded by the nucleotide sequence of SEQ ID NO:2 and said murine light chain variable region of said chimeric antibody representing said one of said two or more chimeric antibodies is encoded by the nucleotide sequence of SEQ ID NO:4, and said murine heavy chain variable region of said chimeric monoclonal antibody representing another of said two or more chimeric antibodies is encoded by the nucleotide sequence of SEQ ID NO:6 and said murine light chain variable region of said another of said two or more chimeric antibodies is encoded by the nucleotide sequence of SEQ ID NO:8.

16. The method of claim 2 or 11 wherein said murine heavy chain variable region of said chimeric antibody representing one of said two or more chimeric antibodies has the amino acid sequence of SEQ ID NO:1 and said murine light chain variable region of said chimeric antibody representing said one of said two or more chimeric antibodies has the amino acid sequence of SEQ ID NO:3, and said murine heavy chain variable region of said chimeric antibody representing another of said two or more chimeric antibodies has the amino acid sequence of SEQ ID NO:5 and said murine light chain variable region of said another of said two or more chimeric antibodies has the amino acid sequence of SEQ ID NO:7.

17. The method of claim 1, 2, 3, or 11 wherein said antibody to be detected in said test sample is selected from the group consisting of IgA, IgD, IgE, IgG, and IgM.

18. The method of claim 1, 2, 3, or 11 wherein said antigen is selected from the group consisting of an infectious agent, an autoantigen, an allergen, and a pharmaceutical compound.

19. The method of claim 18 wherein said infectious agent is selected from the group consisting of a parasite, a bacterium, a fungus, a yeast and a virus.

20. The method of claim 19 wherein said virus is selected from the group consisting of: human immunodeficiency virus-1, human immunodeficiency virus-2, human T-cell leukemia virus-1, human T-cell leukemia virus-2, cytomegalovirus, hepatitis A virus, hepatitis B virus, hepatitis C virus, hepatitis D virus, hepatitis E virus, hepatitis GB virus, respiratory syncytial virus, and Rubella virus, said parasite is selected from the group consisting of *Toxoplasma gondii* and *Trypanosoma cruzi*, said fungus is selected from the group consisting of *Histoplasma capsulatum* and *Cryptococcus neoformans*, and said bacterium is selected from the group consisting of *Helicobacter pylon* and *Streptococcus pyogenes*.

21. A method for detecting the presence of antibody which may be present in a test sample wherein said method comprises (A) contacting said test sample suspected of containing said antibody with anti-antibody specific for said antibody for a time and under conditions sufficient to allow for the formation of anti-antibody/antibody complexes, (B) detecting the presence of said antibody which may be present in said test sample, and employing, as a control or calibrator, a reagent which binds to said anti-antibody, wherein the improvement comprises employing, as said control or calibrator, a chimeric antibody comprising murine heavy and light chain variable regions genetically fused to human or a species immunologically cross-reactive with human heavy and light chain constant regions, wherein said chimeric antibody binds to said antigen and is homogeneous with respect to specificity and affinity.

22. A method for detecting the presence of antibody which may be present in a test sample wherein said method comprises (A) contacting said test sample suspected of containing said antibody with at least one anti-antibody specific for said antibody for a time and under conditions sufficient to allow the formation of anti-antibody/antibody complexes, (B) detecting the presence of said antibody which may be present in said test sample, and employing, as a control or calibrator, two or more reagents which bind to said at least one anti-antibody, wherein the improvement comprises employing, as said control or calibrator, in place of said test sample, two or more chimeric antibodies, wherein each is homogeneous with respect to specificity and affinity and each comprises murine heavy and light chain variable regions genetically fused to human or a species immunologically cross-reactive with human heavy and light chain constant regions, wherein
  1) each of said two or more chimeric antibodies binds to an anti-antibody comprising more than one epitope wherein:
    a) said anti-antibody and said two or more chimeric antibodies are present in a single container or
    b) said anti-antibody and said two or more chimeric antibodies are present in separate containers such that said anti-antibody is present with one of said two or more chimeric antibodies in one container; or
  2) each of said two or more chimeric antibodies binds to a different anti-antibody, said different antigen comprising one or more epitopes wherein:
    a) two of said different anti-antibody and said two or more chimeric antibodies are present in a single container or
    b) each of said two different anti-antibodies and said two or more chimeric antibodies are present in separate containers such that each of said two different anti-antibodies is present with one of said two or more chimeric antibodies in one container of said separate containers, wherein each of said different antigens may be from one source or from different sources.

23. A method for detecting the presence of antibody which may be present in a test sample wherein said method comprises (A) contacting said test sample suspected of containing said antibody with anti-antibody specific for said antibody for a time and under conditions sufficient to allow the formation of anti-antibody/antibody complexes, (B) adding a conjugate to said resulting anti-antibody/antibody complexes for a time and under conditions sufficient to allow said conjugate to bind to said bound antibody, wherein said conjugate comprises an antigen attached to a signal generating compound capable of generating a detectable signal, (C) detecting the presence of said antibody which may be present in said test sample by detecting the signal generating by said signal generating compound, and employing, as a control or calibrator, a reagent which comprises antibody bound by said anti-antibody, wherein the improvement comprises employing, as said control or calibrator, a chimeric antibody comprising murine heavy and light chain variable regions genetically fused to human or a species immunologically cross-reactive with human heavy and light chain constant regions, wherein said chimeric antibody binds to said antigen and is homogeneous with respect to specificity and affinity.

24. The method of claim 21 or 23 wherein said chimeric antibody is a chimeric monoclonal antibody comprising murine heavy and light chain variable regions genetically fused to constant regions derived from a species immunologically cross-reactive with to human constant regions.

25. The method of claim 21 or 23 wherein said chimeric antibody binds specifically to *Toxoplasma gondii*.

26. The method of claim 25 wherein said chimeric antibody binds specifically to protein P30 or protein P66 of *Toxoplasma gondii*.

27. The method of claim 21 or 23 wherein said murine heavy chain variable region of said chimeric antibody is encoded by the nucleotide sequence of SEQ ID NO:2 and said murine light chain variable region of said chimeric antibody is encoded by the nucleotide sequence of SEQ ID NO:4.

28. The method of claim 21 or 23 wherein said murine heavy chain variable region of said chimeric antibody has the amino acid sequence of SEQ ID NO:1 and said murine light chain variable region of said chimeric monoclonal antibody has the amino acid sequence of SEQ ID NO:3.

29. The method of claim 21 or 23 wherein said murine heavy chain variable region of said chimeric antibody is encoded by the nucleotide sequence of SEQ ID NO:6 and said murine light chain variable region of said chimeric antibody is encoded by the nucleotide sequence of SEQ ID NO:8.

30. The method of claim 21 or 23 wherein said murine heavy chain variable region of said chimeric antibody has the amino acid sequence of SEQ ID NO:5 and said murine light chain variable region of said chimeric antibody has the amino acid sequence of SEQ ID NO:7.

31. A method for detecting the presence of antibody which may be present in a test sample wherein said method comprises (A) contacting said test sample suspected of containing said antibody with at least one anti-antibody specific for said antibody for a time and under conditions sufficient to allow the formation of anti-antibody/antibody complexes, (B) adding a conjugate to said resulting anti-antibody/antibody complexes for a time and under conditions sufficient to allow said conjugate to bind to said bound antibody, wherein said conjugate comprises an antigen attached to a signal generating compound capable of generating a detectable signal, (C) detecting the presence of said antibody which may be present in said test sample by detecting the signal generated by said signal generating compound, and employing, as a control or calibrator, two or more chimeric reagents which bind to said at least one anti-antibody, wherein the improvement comprises employing, as said control or calibrator, in place of said test sample, two or more chimeric antibodies each comprising murine heavy and light chain variable regions genetically fused to human or a species immunologically cross-reactive with human heavy and light chain constant regions, wherein each of said two or more chimeric antibodies binds to different epitopes on said anti-antibody and has a unique specificity and affinity, wherein
1) each of said two or more chimeric antibodies binds to an anti-antibody comprising more than one epitope wherein:
   a) said anti-antibody and said two or more chimeric antibodies are present in a single container or
   b) said anti-antibody and said two or more chimeric antibodies are present in separate containers such that said anti-antibody is present with one of said two or more chimeric antibodies in one container; or
2) each of said two or more chimeric antibodies binds to a different anti-antibody, said different anti-antibody comprising one or more epitopes wherein:
   a) two of said different anti-antibody and said two or more chimeric antibodies are present in a single container or
   b) each of said two different anti-antibodies and said two or more chimeric antibodies are present in separate containers such that each of said two different anti-antibodies is present with one of said two or more chimeric antibodies in one container of said separate containers, wherein each of said different anti-antibodies may be from one source or from different sources.

32. The method of claim 22 or 31 wherein each of said two or more chimeric antibodies is a chimeric monoclonal antibody comprising murine heavy and light chain variable regions genetically fused to constant regions derived from a species immunologically cross-reactive with human constant regions.

33. The method of claim 22 or 31 wherein each of said two or more chimeric antibodies binds specifically to *Toxoplasma gondii*.

34. The method of claim 33 wherein each of said two or more chimeric antibodies binds specifically to protein P30 or protein P66 of *Toxoplasma gondii*.

35. The method of claim 22 or 31 wherein said murine heavy chain variable region of said chimeric monoclonal antibody representing one of said two or more chimeric antibodies is encoded by the nucleotide sequence of SEQ ID NO:2 and said murine light chain variable region of said chimeric antibody representing said one of said two or more chimeric antibodies is encoded by the nucleotide sequence of SEQ ID NO:4, and said murine heavy chain variable region of said chimeric antibody representing another of said two or more chimeric antibodies is encoded by the nucleotide sequence of SEQ ID NO:6 and said [L] murine light chain variable region of said another of said two or more chimeric antibodies is encoded by the nucleotide sequence of SEQ ID NO:8.

36. The method of claim 22 or 31 wherein said murine heavy chain variable region of said chimeric antibody representing one of said two or more chimeric antibodies has the amino acid sequence of SEQ ID NO:1 and said murine light chain variable region of said chimeric antibody representing said one of said two or more chimeric antibodies has the amino acid sequence of SEQ ID NO:3, and said murine heavy chain variable region of said chimeric antibody representing another of said two or more chimeric antibodies has the amino acid sequence of SEQ ID NO:5 and murine light chain variable region of said another of said two or more chimeric antibodies has the amino acid sequence of SEQ ID NO:7.

37. The method of claim 21, 22, 23, or 31 wherein said antibody to be detected in said test sample is selected from the group consisting of IgA, IgD, IgE, IgG, and IgM.

38. The method of claim 21, 22, 23, or 31 wherein said antigen selected from the group consisting of an infectious agent, an autoantigen, an allergen, and a pharmaceutical compound.

39. The method of claim 38 wherein said infectious agent is selected from the group consisting of a parasite, a bacterium, a fungus, a yeast and a virus.

40. The method of claim 39 wherein said virus is selected from the group consisting of: human immunodeficiency virus-1, human immunodeficiency virus-2, human T-cell leukemia virus-1, human T-cell leukemia virus-2, cytomegalovirus, hepatitis A virus, hepatitis B virus, hepatitis C virus, hepatitis D virus, hepatitis E virus, hepatitis GB virus, respiratory syncytial virus, and Rubella virus, said parasite is selected from the group consisting of *Toxoplasma gondii* and *Trypanosoma cruzi*, said fungus is selected from the group consisting of *Histoplasma capsulatum* and *Cryptococcus neoformans*, and said bacterium is selected from the group consisting of *Helicobacter pylon* and *Streptococcus pyogenes*.

41. A method for detecting the presence of antibodies, developed against more than one antigen, which may be present in a test sample, wherein said method comprises (A) contacting said test sample suspected of containing said antibodies with antigens specific for said antibodies, respectively, for a time and under conditions sufficient to allow the formation of antigen/antibody complexes, (B) adding direct or indirect conjugates to said antigen/antibody complexes for a time and under conditions sufficient to allow said conjugates to bind to said bound antibodies, wherein said conjugates comprise an antibody attached to a signal generating compound capable of generating a detectable signal, (C) detecting the presence of said antibodies which may be present in said test sample by detecting the signal generating by said signal generating compound, and employing, as controls or calibrators, reagents which bind to said antigens, wherein the improvement comprises employing, as said controls or calibrators, in place of said test sample, chimeric antibodies, wherein each is homogeneous with respect to specificity and affinity and each comprises murine heavy and light chain variable regions genetically fused to human or a species immunologically cross-reactive with human heavy and light chain constant regions, wherein
1) each of said chimeric antibodies binds to an antigen comprising more than one epitope wherein:
   a) each of said antigens and said chimeric antibodies are present in a single container or
   b) said antigens and said chimeric antibodies are present in separate containers such that one of said antigens is present with one of said chimeric antibodies in one container; or
2) each of said chimeric antibodies binds to a different antigen, said different antigen comprising one or more epitopes wherein:
   a) all of said different antigen and said chimeric antibodies are present in a single container or
   b) each of said different antigen and said chimeric antibodies are present in separate containers such that each of said different antigen is present with one of said chimeric antibodies in one container of said separate containers, wherein each of said different antigen may be from one source or from different sources.

42. The method of claim 41 wherein each of said chimeric antibodies is a chimeric monoclonal antibody comprising murine heavy and light chain variable regions genetically fused to constant regions derived from a species immunologically cross-reactive with human constant regions.

43. A kit for determining the presence of antibody in a test sample comprising:

(A) at least one antigen specific for said antibody; and (B) a control or calibrator comprising two or more chimeric antibodies wherein each of said two or more chimeric antibodies comprises murine heavy and light chain variable regions genetically fused to human or a species immunologically cross-reactive with human heavy and light chain constant regions, binds to different epitopes on said at least one antigen, and is homogeneous with respect to specificity and affinity wherein 1) each of said two or more chimeric antibodies binds to an antigen comprising more than one epitope wherein:
   a) said antigen and said two or more chimeric antibodies are present in a single container or
   b) said antigen and said two or more chimeric antibodies are present in separate containers such that said antigen is present with one of said two or more chimeric antibodies in one container; or 2) each of said two or more chimeric antibodies binds to a different antigen, said different antigen comprising one or more epitopes wherein:
   a) two of said different antigen and said two or more chimeric antibodies are present in a single container or
   b) each of said two different antigens and said two or more chimeric antibodies are present in separate containers such that each of said two different antigens is present with one of said two or more chimeric antibodies in one container of said separate containers, wherein each of said different antigens may be from one source or from different sources.

44. A kit for determining the presence of antibody in a test sample comprising:

(A) at least one antigen specific for said antibody;

(B) a direct or indirect conjugate comprising an antibody attached to a signal generating compound capable of generating a detectable signal; and (C) a control or calibrator comprising two or more chimeric antibodies wherein each of said two or more chimeric antibodies comprises murine heavy and light chain variable regions genetically fused to human or a species immunologically cross-reactive with human heavy and light chain constant regions, binds to different epitopes on said at least one antigen, and is homogeneous with respect to specificity and affinity wherein 1) each of said two or more chimeric [reagents] antibodies binds to an antigen comprising more than one epitope wherein:
   a) said antigen and said two or more chimeric antibodies are present in a single container or
   b) said antigen and said two or more chimeric are present in separate containers such that said antigen is present with one of said two or more chimeric antibodies in one container; or 2) each of said two or more chimeric antibodies binds to a different antigen, said different antigen comprising one or more epitopes wherein:
   a) two of said different antigen and said two or more chimeric antibodies are present in a single container or
   b) each of said two different antigens and said two or more chimeric antibodies are present in separate containers such that each of said two different antigens is present with one of said two or more chimeric antibodies in one container of said separate containers, wherein each of said different antigens may be from one source or from different sources.

45. The kit of claim 44 wherein each of said two or more chimeric antibodies is a chimeric monoclonal antibody comprising murine heavy and light chain variable regions genetically fused to constant regions derived from a species immunologically cross-reactive with human constant regions.

46. The kit of claim 43 or 44 wherein said antibody to be detected in said test sample is selected from the group consisting of IgA, IgD, IgE, IgG, and IgM.

47. The kit of claim 43 or 44 wherein said antigen is selected from the group consisting of an infectious agent, an autoantigen, an allergen, and a pharmaceutical compound.

48. A kit for determining the presence of antibody in a test sample comprising:

a) an antigen specific for said antibody; and b) a control or calibrator comprising a chimeric antibody, and may further comprise c) a direct or indirect conjugate comprising an antibody attached to a signal generating compound capable of generating a detectable signal, wherein said chimeric antibody is a chimeric monoclonal antibody comprising murine heavy and light chain variable regions genetically fused to human heavy and light chain constant regions, binds to said antigen, and is homogenous with respect to specifically and affinity.

49. A kit for determining the presence of antibody in a test sample comprising:

(A) at least one anti-antibody specific for said antibody;

(B) at least one antigen specific for said antibody; and (C) a control or calibrator comprising two or more chimeric antibodies wherein each of said two or more chimeric antibodies comprises murine heavy and light chain variable regions genetically fused to human or a species immunologically cross-reactive with human heavy and light chain constant regions, binds to different epitopes on said at least one antigen, and is homogeneous with respect to specificity and affinity wherein 1) each of said two or more chimeric antibodies binds to an antigen comprising more than one epitope wherein:
   a) said antigen and said two or more chimeric antibodies are present in a single container or
   b) said antigen and said two or more chimeric antibodies are present in separate containers such that said antigen is present with one of said two or more chimeric antibodies in one container; or 2) each of said two or more chimeric antibodies binds to a different antigen, said different antigen comprising one or more epitopes wherein:
   a) one or more of said different antigen and said two or more chimeric antibodies are present in a single container or
   b) each of said one or more different antigen and said two or more chimeric antibodies are present in separate containers such that each of said one or more different antigen is present with one of said two or more chimeric antibodies in one container of said separate containers, wherein each of said one or more different antigen may be from one source or from different sources.

50. The kit of claim 49 wherein each of said two or more chimeric antibodies is a chimeric monoclonal antibody comprising murine heavy and light chain variable regions genetically fused to constant regions derived from a species immunologically cross-reactive with human constant regions.

51. The kit of claim 49 wherein said antibody to be detected in said test sample is selected from the group consisting of IgA, IgD, IgE, IgG and IgM.

52. The kit of claim 49 wherein said antigen is selected from the group consisting of an infectious agent, an autoantigen, an allergen, and a pharmaceutical compound.

53. A kit for determining the presence of antibody in a test sample comprising:

a) an anti-antibody specific for said antibody;

b) an antigen specific for said antibody; and c) a control or calibrator; or a) an anti-antibody specific for said antibody;

b) a direct or indirect conjugate comprising an antigen attached to a signal generating compound capable of generating a detectable signal; and c) control or calibrator comprising a chimeric antibody wherein said chimeric antibody is a chimeric monoclonal antibody comprising murine heavy and light chain variable regions genetically fused to human heavy and light chain constant regions, binds to said antigen, and is homogeneous with respect to specificity and affinity.

54. A kit for determining the presence of antibodies, developed against more than one antigen, which may be present in a test sample, comprising:

(A) antigens specific for said antibodies, respectively;

(B) direct or indirect conjugates each comprising an antibody attached to a signal generating compound capable of generating a detectable signal; and (C) controls or calibrators comprising chimeric antibodies wherein each of said chimeric antibodies comprises murine heavy and light chain variable regions genetically fused to human or a species immunologically cross-reactive with human heavy and light chain constant regions, binds to said respective antigens, and is homogeneous with respect to specificity and affinity wherein 1) each of said chimeric antibodies binds to an antigen comprising more than one epitope wherein:

a) each of said antigens and said chimeric antibodies are present in a single container or b) said antigens and said chimeric antibodies are present in separate containers such that one of said antigens is present with one of said chimeric antibodies in one container; or 2) each of said chimeric antibodies binds to a different antigen, said different antigen comprising one or more epitopes wherein:

a) all of said different antigen and said chimeric antibodies are present in a single container or b) each of said different antigen and said chimeric antibodies are present in separate containers such that each of said different antigen is present with one of said chimeric antibodies in one container of said separate containers, wherein each of said different antigen may be from one source or from different sources.

55. The kit of claim 54 wherein each of said chimeric antibodies is a chimeric monoclonal antibody comprising murine heavy and light chain variable regions genetically fused to constant regions derived from a species immunologically cross-reactive with human constant regions.

* * * * *

UNITED STATES PATENT AND TRADEMARK OFFICE
CERTIFICATE OF CORRECTION

PATENT NO. : 6,015,662
DATED : January 18, 2000
INVENTOR(S) : John R. Hackett, Jr. et al.

It is certified that error appears in the above-identified patent and that said Letters Patent is hereby corrected as shown below:

Column 2,
Line 46, replace "phoshatase" with -- phosphatase --.

Column 4,
Line 53, replace "pylon" with -- pylori --.

Column 7,
Line 25, replace "specifity" with -- specificity --.

Column 9,
Lines 4, 12, and 22, replace "specifity" with -- specificity --.

Column 10,
Lines 17 and 52, replace "specifity" with -- specificity --.

Column 11,
Line 34, replace "varaitions" with -- variations --.
Line 44, replace "may encoded" with -- may be encoded --.

Column 12,
Lines 35, 43, and 52, replace "specifity" with -- specificity --.

Column 14,
Lines 42 and 61, replace "IgGI" with -- IgG1 --.
Line 65, replace "Hind HI" with -- Hind HIII --.

Column 15,
Line 3, replace "B 1" with -- B1 --.
Line 17, replace "educed" with -- deduced --.

Column 16,
Line 4, replace "CK" with -- Cκ --.
Line 33, replace "mil" with -- ml --.
Lines 33 and 41, replace "45°C." with -- 45°C --.

Column 18,
Line 38, replace "etal." with -- et al. --.

UNITED STATES PATENT AND TRADEMARK OFFICE
CERTIFICATE OF CORRECTION

PATENT NO. : 6,015,662
DATED : January 18, 2000
INVENTOR(S) : John R. Hackett, Jr. et al.

It is certified that error appears in the above-identified patent and that said Letters Patent is hereby corrected as shown below:

Column 19,
Line 11, replace "20" with -- --.
Line 30, replace "35" with -- --.
Line 62, replace "ape, and human" with -- ape (e.g. chimpanzee), and human --.

Column 20,
Line 9, replace "uman" with -- human --.

Column 21,
Line 4, replace "(EH)" with -- ($E_H$) --.

Column 22,
Line 8, replace "20" with -- --.
Line 15, replace "25" with -- --.
Line 16, replace "ape, and human" with -- ape (e.g. chimpanzee), and human --.

Column 23,
Line 47, replace "limited: myeloma" with -- limited to: myeloma --.

Column 26,
Line 8, replace "(IgG2b/K)" with -- (IgG2b/κ) --.
Line 9, replace "(IgG2a/ic)" with -- (IgG2a/κ) --.
Line 15, replace "100 U" with -- 100U --.
Line 33, replace "37°C" with -- 37°C --.
Line 60, replace "68°C" with -- 68°C --.

Column 27,
Line 1, replace "20°C" with -- 20° C --.
Line 3, replace "(-20 ° C.)" with -- (-20 ° C) --.
Line 49, replace "C." with -- C --.
Line 49, replace "50-60°C." with -- 50-60°C --.
Line 50, replace "72°C" with -- 72°C --.

Column 28,
Line 6, replace "(K)" with -- (κ) --.
Line 9, replace "42°C." with -- 42°C --.
Line 10, replace "C." with -- C --.
Line 10, replace "(100 volume; 50 pmol of each primer)" with -- 100 μ volume; 50 pmol of each primer) --.
Line 14, replace "VK" with -- Vκ --.
Line 15, replace "VH" with -- $V_H$ --.

UNITED STATES PATENT AND TRADEMARK OFFICE
CERTIFICATE OF CORRECTION

PATENT NO. : 6,015,662
DATED : January 18, 2000
INVENTOR(S) : John R. Hackett, Jr. et al.

It is certified that error appears in the above-identified patent and that said Letters Patent is hereby corrected as shown below:

Column 28, contd.
Line 20, replace "94°C." with -- 94°C --.
Line 20, replace "52°C." with -- 52°C --.
Line 21, replace "72°C." with -- 72°C --.
Line 25, replace "pUC 18" with -- pUC18 --.
Line 62, replace "pAG/SpeI" with -- pAG/SPeI --.

Column 29,
Line 3, replace "94°C." with -- 94°C --.
Line 4, replace "63°C." with -- 63°C --.
Line 4, replace "72°C." with -- 72°C --.
Line 9, replace "IgGI" with -- IgG1 --.
Line 12, replace "pAG/SpeI/huM" with -- pAG/SpeI/huM --.
Line 37, replace "94°C." with -- 94°C --.
Line 37, replace "60°C." with -- 60°C --.
Line 38, replace "72°C." with -- 72°C --.

Column 30,
Lines 3 and 9, replace "pJH2-24-95B 1" with -- pJH2-24-95B1 --.
Line 26, replace "VK" with -- Vκ --.
Line 30, replace "VH 1-706-3" with -- VH1-706-3 --.
Line 42, replace "94°C." with -- 94°C --.
Line 42, replace "62°C." with -- 62°C --.
Line 43, replace "72°C." with -- 72°C --.
Line 43, replace "Vic" with -- Vκ --.
Line 45, replace "(pAG/SpeI/huM)" with -- (pAG/SpeI/huM) --.
Line 50, replace "he" with -- the --.

Column 31,
Line 21, replace "Vic" with -- Vκ --.
Line 21, replace "VH" with -- $V_H$ --.
Line 22, replace "Hind II" with -- Hind III --.
Line 27, replace "5465-210" with -- 5-465-210 --.

Column 32,
Line 38, replace "Vic" with -- Vκ --.

Table 4,
Line 5, replace "HMC-5 5'd[ACTCTTGCCCcTCTTCCTGC]3'(SEQ ID NO:40)"
with -- HMC-5 5'd[ACTCTTGCCCCTCTTCCTGC]3' (SEQ ID NO:40) --.

UNITED STATES PATENT AND TRADEMARK OFFICE
CERTIFICATE OF CORRECTION

PATENT NO.     : 6,015,662
DATED          : January 18, 2000
INVENTOR(S)    : John R. Hackett, Jr. et al.

It is certified that error appears in the above-identified patent and that said Letters Patent is hereby corrected as shown below:

Column 34,
Line 66, replace "λF" with -- µF --.

Column 35,
Line 5, replace "37°C0" with -- 37°C --.
Line 22, replace "C." with -- C --.
Line 30, replace "4°C." with -- 4°C --.
Lines 38 and 49, replace "37°C." with -- 37°C --.

Column 36,
Lines 9 and 21, replace "37°C." with -- 37°C --.
Line 46, replace "35-37°C." with -- 35-37°C --.

Column 37,
Line 56, replace "$V_{L\,d}cDNA$" with -- $V_L$ cDNA --.
Line 57, replace "Vic" with -- Vκ --.

Column 38,
Line 62, replace "IgG 1" with -- IgG1 --.

Column 41,
Line 43, replace "(calibrator F, 300 Iu/ml)" with -- (calibrator F, 300 IU/ml) --.
Line 49, replace "Iu/ml" with -- IU/ml --.

Column 42,
Lines 10, 23, 27, and 30, replace "45°C." with -- 45°C --.
Line 22, replace "2-8°C." with -- 2-8°C --.

Column 73,
Lines 45 and 64, replace "cross0reactive" with -- cross-reactive --.

Column 75,
Line 3, replace "cross0reactive" with -- cross-reactive --.
Line 11, replace "to" with -- with --.

Column 76,
Line 26, replace "claims" with -- claim --.

UNITED STATES PATENT AND TRADEMARK OFFICE
CERTIFICATE OF CORRECTION

PATENT NO. : 6,015,662
DATED : January 18, 2000
INVENTOR(S) : John R. Hackett, Jr. et al.

It is certified that error appears in the above-identified patent and that said Letters Patent is hereby corrected as shown below:

Column 77,
Line 7, replace "pylon" with -- pylori --.

Column 78,
Line 25, replace "with to human" with -- with human --.

Column 80,
Line 27, replace "pylon" with -- pylori --.

Column 81,
Line 64, replace "chimeric are" with -- chimeric antibodies are --.

Column 82,
Line 13, replace "The kit of claim 44" with -- The kit of claim 43 or 44 --.
Line 37, replace "specifically" with -- specificity --.

Column 83,
Lines 13 and 16, replace "49" with -- 48 or 49 --.

Signed and Sealed this

Twelfth Day of February, 2002

Attest:

JAMES E. ROGAN
Attesting Officer  Director of the United States Patent and Trademark Office

SEQUENCE LISTING (1) GENERAL INFORMATION:

(iii) NUMBER OF SEQUENCES: 70

(2) INFORMATION FOR SEQ ID NO:1:

(i) SEQUENCE CHARACTERISTICS:
      (A) LENGTH: 138 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Met Gly Trp Ser Trp Ile Phe Leu Phe Leu Ser Val Thr Ala Gly
1               5                   10                  15

Val His Ser Gln Val His Leu Gln Gln Ser Gly Ala Glu Leu Val Arg
            20                  25                  30

Pro Gly Thr Ser Val Lys Val Ser Cys Lys Ala Ser Gly Tyr Ala Phe
        35                  40                  45

Thr Asn Tyr Leu Ile Glu Trp Val Thr Gln Arg Pro Gly Gln Gly Leu
    50                  55                  60

Glu Trp Ile Gly Val Ile Asn Pro Gly Ser Asp Phe Thr Tyr Tyr Asn
65                  70                  75                  80

Glu Lys Phe Lys Gly Arg Ala Thr Leu Thr Ala Asp Lys Ser Ser Ser
                85                  90                  95

Thr Ala Tyr Met Gln Leu Thr Ser Leu Thr Ser Asp Asp Ser Ala Val
            100                 105                 110

Tyr Phe Cys Ala Arg Thr Ile Val Thr Thr Asp Tyr Phe Asp Tyr Trp
        115                 120                 125

Gly Gln Gly Thr Pro Leu Thr Val Ser Ser
    130                 135
```

(2) INFORMATION FOR SEQ ID NO:2:

(i) SEQUENCE CHARACTERISTICS:
      (A) LENGTH: 447 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
CTCGAGACTC CAACCATGGG ATGGAGCTGG ATCTTTCTCT TTCTCCTGTC AGTAACTGCA    60

GGTGTTCACT CCCAGGTCCA TCTGCAGCAG TCTGGAGCTG AGCTGGTAAG GCCTGGGACT   120

TCAGTGAAGG TGTCCTGCAA GGCTTCTGGA TACGCCTTCA CTAATTACTT GATAGAGTGG   180

GTGACACAGA GGCCTGGACA GGGCCTTGAG TGGATTGGAG TGATTAATCC TGGAAGTGAT   240

TTTACTTACT ACAATGAGAA ATTCAAGGGC AGGGCAACAC TGACTGCAGA CAAATCCTCC   300

AGCACTGCCT ACATGCAGCT CACCAGCCTG ACATCTGATG ACTCTGCGGT CTATTTCTGT   360

GCAAGAACTA TTGTGACTAC GGACTACTTT GACTACTGGG GCCAAGGCAC CCCTCTCACA   420

GTCTCCTCAG GTAAGTGTGT CAAGCTT                                      447
```

(2) INFORMATION FOR SEQ ID NO:3:

(i) SEQUENCE CHARACTERISTICS:
        (A) LENGTH: 131 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Glu Ser Asp Thr Leu Leu Leu Trp Val Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Ser Ile Arg Gly Ala Gly Leu Met His Trp Tyr Gln Gln Lys Pro
    50                  55                  60

Gly Tyr Pro Pro Lys Leu Leu Ile Tyr Ala Ala Ser Asn Leu Glu Ser
65                  70                  75                  80

Gly Val Pro Ala Arg Phe Ser Gly Arg Gly Ser Gly Thr Asp Phe Thr
                85                  90                  95

Leu Asn Ile His Pro Val Glu Glu Ala Asp Ala Ala Thr Tyr Phe Cys
            100                 105                 110

Gln Gln Ser Arg Arg Tyr Pro Tyr Thr Phe Gly Ser Gly Thr Lys Leu
        115                 120                 125

Glu Ile Lys
    130
```

(2) INFORMATION FOR SEQ ID NO:4:

(i) SEQUENCE CHARACTERISTICS:
        (A) LENGTH: 428 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
TCTAGAGCTC TCAGAGATGG AGTCAGACAC ACTCCTGCTA TGGGTGCTAC TGCTCTGGGT    60

TCCAGGCTCC ACTGGTGACA TTGTGCTGAC CCAATCTCCA GCTTCTTTGG CTGTGTCTCT   120

GGGGCAGAGG GCCACCATCT CCTGCAGAGC CAGCGAAAGT GTCAGTATTC GTGGTGCTGG   180

TTTAATGCAC TGGTATCAAC AGAAACCAGG ATATCCACCC AAACTCCTCA TCTATGCTGC   240

ATCCAACCTA GAATCTGGGG TGCCTGCCAG GTTTAGTGGC AGAGGGTCTG GGACAGACTT   300

CACCCTCAAC ATTCATCCTG TGGAGGAAGC TGATGCTGCA ACCTATTTCT GTCAGCAAAG   360
```

```
TAGGAGATAT CCGTATACGT TCGGATCGGG GACCAAGCTG GAAATAAAAC GTAAGTGTGT        420

CAGGATCC                                                                428
```

(2) INFORMATION FOR SEQ ID NO:5:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Ala Trp Val Trp Thr Leu Leu Phe Leu Met Ala Ala Ala Gln Ser
 1               5                  10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr His Tyr Pro Met His Trp Val Lys Gln Ala Pro Gly Lys Ser Leu
    50                  55                  60

Lys Trp Met Gly Trp Ile Asn Thr Lys Ser Gly Val Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Cys Leu Gln Ile Thr Asn Leu Lys Asn Glu Asp Met Ala Thr
            100                 105                 110

Tyr Phe Cys Val Arg Gly Gly Leu Tyr Tyr Asp Tyr Phe Tyr Gly Val
        115                 120                 125

Asp Tyr Trp Gly Gln Gly Thr Ser Val Thr Val Ser Ser
    130                 135                 140
```

(2) INFORMATION FOR SEQ ID NO:6:

(i) SEQUENCE CHARACTERISTICS:
        (A) LENGTH: 452 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
CTCGAGACAT CATGGCTTGG GTGTGGACCT TGCTATTCCT GATGGCAGCT GCCCAAAGTA        60

TCCAAGCACA GATCCAGTTG GTGCAGTCTG GACCTGAGCT GAAGAAGCCT GGAGAGACAG       120

TCAAGATCTC CTGCAAGGCT TCTGGGTATA CCTTCACACA CTATCCAATG CACTGGGTGA       180

AGCAGGCTCC AGGAAAGAGT TTAAAGTGGA TGGGCTGGAT AAACACCAAG TCTGGAGTGC       240

CAACATATGC AGATGACTTC AAGGGACGGT TTGCCTTCTC TTTGGAAACC TCTGCCAGCA       300

CTGCATGTTT GCAGATCACC AACCTCAAAA ATGAGGACAT GGCTACATAT TTCTGTGTAA       360

GAGGAGGGCT CTACTATGAT TATTTCTATG GTGTGGACTA CTGGGGTCAA GGAACCTCAG       420

TCACCGTCTC CTCAGGTAAG TGTGTCAAGC TT                                     452
```

(2) INFORMATION FOR SEQ ID NO:7:

(i) SEQUENCE CHARACTERISTICS:
        (A) LENGTH: 131 amino acids
        (B) TYPE: amino acid (C) STRANDEDNESS: single
            (D) TOPOLOGY: linear (ii) MOLECULE TYPE: protein (xi) SEQUENCE DESCRIPTION: SEQ ID NO:7:

```
Met Lys Leu Pro Val Arg Leu Leu Val Leu Met Phe Trp Ile Pro Ala
1               5                  10                  15

Ser Ser Ser Asp Val Val Met Thr Gln Thr Pro Leu Ser Leu Pro Val
            20                  25                  30

Ser Pro Gly Asp Gln Ala Ser Ile Ser Cys Arg Ser Ser Gln Ser Leu
        35                  40                  45

Val His Ser Tyr Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Trp Thr Phe Gly Gly Gly Thr Lys Leu
        115                 120                 125

Glu Ile Lys
    130
```

(2) INFORMATION FOR SEQ ID NO:8:

(i) SEQUENCE CHARACTERISTICS:
        (A) LENGTH: 424 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
TCTAGACCTC AAATGAAGTT GCCTGTTAGG CTGTTGGTGC TGATGTTCTG GATTCCTGCT      60

TCCAGCAGTG ATGTGGTGAT GACCCAGACT CCACTCTCCC TGCCTGTCAG TCCTGGAGAT     120

CAAGCCTCGA TCTCTTGCAG ATCTAGTCAG AGCCTTGTAC ACAGTTATGG AAACACCTAT     180

TTACATTGGT ATCTGCAGAA GCCAGGCCAG TCTCCAAAAC TCCTGATCTA CAAAGTTTCC     240

AACCGATTTT CTGGGGTCCC AGACAGGTTC AGTGGCAGTG GATCAGGGAC AGATTTCACA     300

CTCAAGATCA GCAGAGTGGA GGCTGAGGAT CTGGGAGTTT ATTTCTGCTC TCAAAGTACA     360

CATGTTCCGT GGACGTTCGG TGGAGGCACC AAGCTGGAAA TCAAACGTAA GTGTGTCAGG     420

ATCC                                                                  424
```

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
ATTCGGATAG ATCTAGTGGA TAGACTGATG G                                     31
```

(2) INFORMATION FOR SEQ ID NO:10:

```
    (i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

ATTCGGATAG ATCTAGTGGA TAGACCGATG G                                    31

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ATTCGGATAG ATCTTGGATG GTGGGAAGAT G                                    31

(2) INFORMATION FOR SEQ ID NO:12:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

ACACTAGTCG ACATGGMTTG GGTGTGGAMC TTGCTATTCC TG                        42

(2) INFORMATION FOR SEQ ID NO:13:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

ACACTAGTCG ACATGAAGTT GCCTGTTAGG CTGTTGGTGC TG                        42

(2) INFORMATION FOR SEQ ID NO:14:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

ACACTAGTCG ACATGGRATG GAGCKGGRTC TTTMTCTT                             38

(2) INFORMATION FOR SEQ ID NO:15:

(i) SEQUENCE CHARACTERISTICS:
        (A) LENGTH: 41 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO:15:

ACACTAGTCG ACATGGAGWC AGACACACTC CTGYTATGGG T            41

(2) INFORMATION FOR SEQ ID NO:16:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

TGACTGTAAC TAGTCCTGCG GGTCCTCAGG GAGTGCATCC GCCCCAACCC TTTTCCCCCT    60
C                                                                   61

(2) INFORMATION FOR SEQ ID NO:17:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

CGACGGGGAA TTCTCACAGG AGAC                              24

(2) INFORMATION FOR SEQ ID NO:18:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

GGAACTAGTG GAGC                                         14

(2) INFORMATION FOR SEQ ID NO:19:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

TCCACTAGTT CCGC                                         14

(2) INFORMATION FOR SEQ ID NO:20:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

ACGTCATCCG ACCCCCTCAG                                                                              20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CTGCCCCAAA GCCAAGGTCA                                                                              20

(2) INFORMATION FOR SEQ ID NO:22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CTCCAGCTTC ACCAGATCCC TCGAC                                                                        25

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CTCCAGCTTC ACCAGATCCC TCGAG                                                                        25

(2) INFORMATION FOR SEQ ID NO:24:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GCCACCTGCC TCACCTTAG                                                                               19

(2) INFORMATION FOR SEQ ID NO:25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

AGAATGGCCA CGTCATCCG                                                                               19

-continued (2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

TCCAATGCAC TGGGTGAAGC                                     20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GCAAACCGTC CCTTGAAGTC                                     20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

ATTTACATTG GTATCTGCAG                                     20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CCAGAAAATC GGTTGGAAAC                                     20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CGAGACTCCA ACCATGGGAT                                     20

(2) INFORMATION FOR SEQ ID NO:31:

(i) SEQUENCE CHARACTERISTICS:
        (A) LENGTH: 20 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:31:

TGATAGAGTG GGTGACACAG                                               20

(2) INFORMATION FOR SEQ ID NO:32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:32:

GCCCTGCCCT TGAATTTCTC                                               20

(2) INFORMATION FOR SEQ ID NO:33:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:33:

TAGAGCTCTC AGAGATGGAG                                               20

(2) INFORMATION FOR SEQ ID NO:34:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:34:

CTATGCTGCA TCCAACCTAG                                               20

(2) INFORMATION FOR SEQ ID NO:35:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:35:

GATGAATGTT GAGGGTGAAG                                               20

(2) INFORMATION FOR SEQ ID NO:36:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO:36:

ATACAAGAAC AACTCTGACA                     20

(2) INFORMATION FOR SEQ ID NO:37:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

GTCTTCGTCC CACCCCGCG                      19

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

CTCCATGTGT GTCCCCGGTG                     20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

ATCCTTTGCC AGCATCTTCC                     20

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

ACTCTTGCCC CTCTTCCTGC                     20

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

GACCAGCGCC CCAATGCCTG                     20

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

TTTGCATGCA CACACAGAGC      20

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

GCATCCACTG CACGAAGACG      20

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

AGGGCAGGTC TGTGTGGGTC      20

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

CATGGTTCCC ACCCAAAGAG      20

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

ACTCTTTGGC CTCAGCCTGC      20

(2) INFORMATION FOR SEQ ID NO:47:

(i) SEQUENCE CHARACTERISTICS:
        (A) LENGTH: 20 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

GCACACCACG TGTTCGTCTG                                              20

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

GTGCATGCAA ACTAACCGTG                                              20

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

GCTCCTCCCA TATGGTCGAC                                              20

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

CAGGCCCGAT GTCTACTTGC                                              20

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

CTCATGGGCC ACCACGCAGG                                              20

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:52:

CTGCGAGGAT GACTGGAATT                                               20

(2) INFORMATION FOR SEQ ID NO:53:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:53:

GCTGGTCACA TACTTCTCCG                                               20

(2) INFORMATION FOR SEQ ID NO:54:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:54:

CGGGAGCTGC ATGTGTCAG                                                19

(2) INFORMATION FOR SEQ ID NO:55:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:55:

CAGACACTGG ACGCTGAACC                                               20

(2) INFORMATION FOR SEQ ID NO:56:

(i) SEQUENCE CHARACTERISTICS:
      (A) LENGTH: 48 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:56:

TGATCTAGCG GCCGTCGCAC TCAGTAGCAG GTGCCAGCTG TGTCGGAC                48

(2) INFORMATION FOR SEQ ID NO:57:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:57:

CTGATCGAGA TATCAAGCCA CTGAGGCACG CAGGTGGGTG                         40

(2) INFORMATION FOR SEQ ID NO:58:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

TCAGGTGACT GAACTAGTCC TTGGTGGGGC AGCCACAGCG             40

(2) INFORMATION FOR SEQ ID NO:59:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

TCACGAAGTC TAGACCTCAA ATGAAGTTGC CTGTTAGGCT GTTGGTG        47

(2) INFORMATION FOR SEQ ID NO:60:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

GAATCTATGG ATCCTGACAC ACTTACGTTT GATTTCCAGC TTGGTGCCTC C    51

(2) INFORMATION FOR SEQ ID NO:61:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

ACACTATACT CGAGACATCA TGGCTTGGGT GTGGACCTTG CTA          43

(2) INFORMATION FOR SEQ ID NO:62:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

TTCAGATCAA GCTTGACACA CTTACCTGAG GAGACGGTGA CTGAGGTTCC     50

(2) INFORMATION FOR SEQ ID NO:63:

(i) SEQUENCE CHARACTERISTICS:
        (A) LENGTH: 48 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

TCACGAAGTC TAGAGCTCTC AGAGATGGAG TCAGACACAC TCCTGCTA                48

(2) INFORMATION FOR SEQ ID NO:64:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

GAATCTATGG ATCCTGACAC ACTTACGTTT TATTTCCAGC TTGGTCCCCG              50

(2) INFORMATION FOR SEQ ID NO:65:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

ACACTATACT CGAGACTCCA ACCATGGGAT GGAGCTGGAT CTTTCTC                 47

(2) INFORMATION FOR SEQ ID NO:66:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

TTCAGATCAA GCTTGACACA CTTACCTGAG GAGACTGTGA GAGGGGTG                48

(2) INFORMATION FOR SEQ ID NO:67:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

GTAAAACGAC GGCCAGT                                                  17

(2) INFORMATION FOR SEQ ID NO:68:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO:68:

CAGGAAACAG CTATGAC                                                17

(2) INFORMATION FOR SEQ ID NO:69:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:69:

GAGCGGATAA CAATTTCACA CAGG                                        24

(2) INFORMATION FOR SEQ ID NO:70:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:70:

TGTAAAACGA CGGCCAGT                                               18